United States Patent
Dor et al.

(10) Patent No.: US 11,466,323 B2
(45) Date of Patent: Oct. 11, 2022

(54) DUAL-PROBE DIGITAL DROPLET PCR STRATEGY FOR SPECIFIC DETECTION OF TISSUE-SPECIFIC CIRCULATING DNA MOLECULES

(71) Applicants: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

(72) Inventors: Yuval Dor, Jerusalem (IL); Ruth Shemer, Mevasseret Zion (IL); Benjamin Glaser, Jerusalem (IL); Judith Magenheim, Efrat (IL)

(73) Assignees: YISSUM RESEARCH DEVELOPMENT COMPANY OF THE HEBREW UNIVERSITY OF JERUSALEM LTD., Jerusalem (IL); HADASIT MEDICAL RESEARCH SERVICES AND DEVELOPMENT LTD., Jerusalem (IL)

( * ) Notice: Subject to any disclaimer, the term of this patent is extended or adjusted under 35 U.S.C. 154(b) by 155 days.

(21) Appl. No.: 16/630,593

(22) PCT Filed: Jul. 13, 2018

(86) PCT No.: PCT/IL2018/050772
§ 371 (c)(1),
(2) Date: Jan. 13, 2020

(87) PCT Pub. No.: WO2019/012544
PCT Pub. Date: Jan. 17, 2019

(65) Prior Publication Data
US 2020/0172970 A1    Jun. 4, 2020

Related U.S. Application Data

(60) Provisional application No. 62/531,983, filed on Jul. 13, 2017.

(51) Int. Cl.
*C12Q 1/6876* (2018.01)
*C12Q 1/6827* (2018.01)
*C12Q 1/686* (2018.01)
*C12Q 1/6869* (2018.01)

(52) U.S. Cl.
CPC .......... *C12Q 1/6876* (2013.01); *C12Q 1/686* (2013.01); *C12Q 1/6827* (2013.01); *C12Q 1/6869* (2013.01); *C12Q 2523/125* (2013.01); *C12Q 2535/131* (2013.01); *C12Q 2561/101* (2013.01); *C12Q 2600/154* (2013.01)

(58) Field of Classification Search
CPC .... C12Q 1/6876; C12Q 1/6827; C12Q 1/686; C12Q 1/6869; C12Q 2523/125; C12Q 2535/131; C12Q 2561/101; C12Q 2600/154
See application file for complete search history.

(56) References Cited

U.S. PATENT DOCUMENTS

| | | | |
|---|---|---|---|
| 2008/0254447 A1* | 10/2008 | Foekens | A61P 35/00 435/6.14 |
| 2011/0217712 A1* | 9/2011 | Hiddessen | C12Q 1/6846 435/6.12 |
| 2012/0252015 A1* | 10/2012 | Hindson | C12Q 1/6883 435/6.11 |
| 2013/0295567 A1 | 11/2013 | Link et al. | |
| 2014/0287404 A1 | 9/2014 | Huang et al. | |

FOREIGN PATENT DOCUMENTS

| | | | | |
|---|---|---|---|---|
| CA | 2989573 A1 * | 12/2016 | | C12Q 1/6886 |
| WO | 2008149237 A2 | 12/2008 | | |
| WO | 201101728 A1 | 1/2011 | | |
| WO | 2013131083 A1 | 9/2013 | | |
| WO | 2014138133 A1 | 9/2014 | | |
| WO | 2015159292 A2 | 10/2015 | | |
| WO | 2015169947 A1 | 11/2015 | | |
| WO | 2017011390 A1 | 1/2017 | | |

OTHER PUBLICATIONS

Schneider et al. Evaluation of GRCh38 and de novo haploid genome assemblies demonstrates the enduring quality of the reference assembly. Genome Research, May 2017, 27, 5, pp. 849-864 (Year: 2017).*
Vaughan et al. Where in the genome are we? A cautionary tale of database use in genomics research. Frontiers in Genetics, Mar. 2003, 4, 38 (Year: 2003).*
Yibin Liu et al: "Methylation-sensitive enrichment of minor DNA alleles using a double-strand DNA-specific nuclease", Nucleic Acids Research, vol. 45, No. 6, Nov. 28, 2016 pp. e39-e39.
Nicholas Redshaw et al: "Quantification of epigenetic biomarkers: an evaluation of established and emerging methods for DNA methylation analysis" BMC Genomics, Biomed Central, vol. 15, No. 1, Dec. 23, 2014.

(Continued)

*Primary Examiner* — David C Thomas
(74) *Attorney, Agent, or Firm* — The Roy Gross Law Firm, LLC; Roy Gross

(57) ABSTRACT

A digital droplet PCR method of analyzing the methylation status of methylation sites of a double-stranded DNA molecule which comprises at least two methylation sites per single strand of the double-stranded DNA molecule is disclosed.

14 Claims, 17 Drawing Sheets
(15 of 17 Drawing Sheet(s) Filed in Color)
Specification includes a Sequence Listing.

(56) References Cited

OTHER PUBLICATIONS

Masamichi Hayashi et al: "Paired box 5 methylation detection by droplet digital PCR for ultra-sensitive deep surgical margins analysis of head and neck squamous cell carcinoma" Cancer Prevention Research, vol. 8, No. 11, Aug. 24, 2015.

Hernan G. Hernandez et al: "Optimizing methodologies for PCR-based DNA methylation analysis", Biotechniques Rapid Dispatches, vol. 55, No. 4, Oct. 1, 2013.

Ekaterina Olkhov-Mitsel et al: "Novel Multiplex MethyLight Protocol for Detection of DNA Methylation in Patient Tissues and Bodily Fluids". Scientific Reports. vol. 4. Mar. 21, 2014.

Roni Lehmann-Werman et al: "Monitoring liver damage using hepatocyte-specific methylation markers in cell-free circulating DNA". JCI Insight. vol. 3. No. 12. Jun. 21, 2018.

Ming Yu et al: "MethyLight droplet digital PCR for detection and absolute quantification of infrequently methylated alleles" Epigenetics, vol. 10, No. 9, Jul. 17, 2015.

Hai Zemmour et al: "Non-invasive detection of human cardiomyocyte death using methylation patterns of circulating DNA", Nature Communications, vol. 9, No. 1, Apr. 24, 2018.

Emily Hodges et al., "High definition profiling of mammalian DNA methylation by array capture and single molecule bisulfite sequencing", vol. 19 Issue 9 pp. 1593-1605, Sep. 2009.

Roni Lehmann-Werman et al., "Identification of tissue-specific cell death using methylation patterns of circulating DNA", Proc Natl Acad Sci USA, vol. 113 Issue 13 pp. E1826-E1834, Mar. 2016.

Jia Zhong et al., "The Role of DNA Methylation in Cardiovascular Risk and Disease Methodological Aspects, Study Design, and Data Analysis for Epidemiological Studies", vol. 118 No. 1 pp. 119-131, Jan. 2016.

Austin K. Mattox et al., "Bisulfite-converted duplexes for the strand-specific detection and quantification of rare mutations", Proceedings of the National Academy of Sciences, vol. 114 Issue 18 pp. 4733-4738, Apr. 2017.

Dustin R. Masser et al., "Bisulfite oligonucleotide-capture sequencing for targeted base- and strand-specific absolute 5-methylcytosine quantitation", vol. 38 Issue 3 p. 49, Jun. 2016.

QIAGEN: "Epigenetics Sample and Assay Technologies", Internet Citation, pp. 1-12, XP002691674, Nov. 2010.

Mohamed I. Husseiny et al: "Tissue-Specific Methylation of Human Insulin Gene and PCR Assay for Monitoring Beta Cell Death", PLOS ONE, vol. 9, No. 4, p. e94591, XP055197433, Apr. 10, 2014.

Eitan M. Akirav et al.: "Detection of β cell death in diabetes using differentially methylated circulating DNA", Proceedings of the National Academy of Sciences of the United States of America, 108, pp. 19018-19023, 2011.

Jasmin Lebastchi et al.: "Immune Therapy and β-Cell Death in Type 1 Diabetes", Diabetes, vol. 62 Issue 5 pp. 1676-1680, 2013.

Kevan C. Herold et al.: "β cell death and dysfunction during type 1 diabetes development in at-risk individuals", J Clin Invest., vol. 125 Issue 3 pp. 1163-1173, 2015.

Roza Bidshahri et al.: "Quantitative Detection and Resolution of BRAF V600 Status in Colorectal Cancer Using Droplet Digital PCR and a Novel Wild-Type Negative Assay", The Journal of Molecular Diagnostics, vol. 18 No. 2 pp. 190-204, Mar. 2016.

Sahar Usmani-Brown et al.: "Analysis of β-Cell Death in Type 1 Diabetes by Droplet Digital PCR", Endocrinology, vol. 155 Issue 9 pp. 3694-3698, 2014.

Sarah-Jane Dawson et al.: "Analysis of circulating tumor DNA to monitor metastatic breast cancer", The New England Journal of Medicine, vol. 368 Issue 13 pp. 1199-1209, 2013.

Thomas M. Snyder et al.: "Universal noninvasive detection of solid organ transplant rejection", Proc Natl Acad Sci USA, vol. 108 Issue 15 pp. 6229-6234, 2011.

Iwijn De Vlaminck et al.: "Circulating cell-free DNA enables noninvasive diagnosis of heart transplant rejection", Sci Transl Med, vol. 6 Issue 241 p. 241ra277, 2014.

Kun Sun et al.: "Plasma DNA tissue mapping by genome-wide methylation sequencing for noninvasive prenatal, cancer, and transplantation assessments", Proc Natl Acad Sci USA, vol. 112 Issue 40 pp. E5503-E5512, 2015.

Shicheng Guo et al.: "Identification of methylation haplotype blocks aids in deconvolution of heterogeneous tissue samples and tumor tissue-of-origin mapping from plasma DNA", Nat Genet, vol. 49 Issue 4 pp. 635-642, 2017.

Roadmap Epigenomics Consortium et al.: "Integrative analysis of 111 reference human epigenomes", Nature, vol. 518 Issue 317-330, 2015.

Jared T. Simpson et al.: "Detecting DNA cytosine methylation using nanopore sequencing", Nature Methods, vol. 14 Issue 4 pp. 407-410, 2017.

PCT Search Report for International Application No. PCT/IL2018/050772; dated Oct. 17, 2018; 6 pp.

PCT Written Opinion for International Application No. PCT/IL2018/050772; dated Oct. 17, 2018; 6 pp.

PCT Preliminary Report for International Application No. PCT/IL2018/050772; dated Jan. 14, 2020 ; 7 pp.

* cited by examiner

FIG. 3A
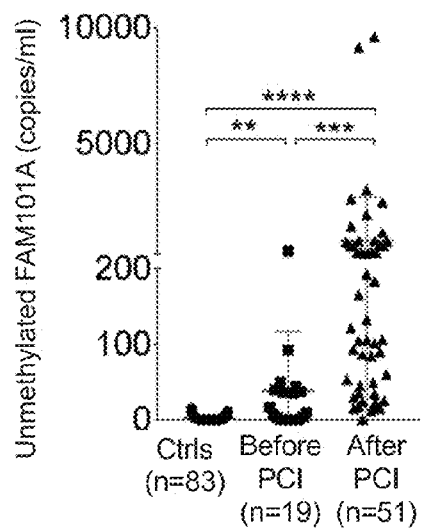
FIG. 3B
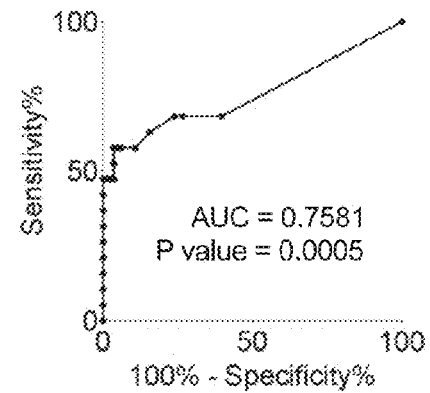
FIG. 3C
——— Cardiomyocyte-derived DNA
——— Troponin
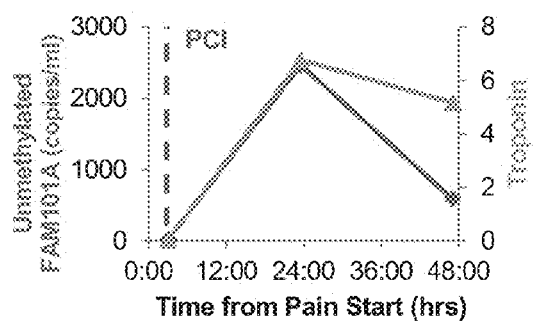
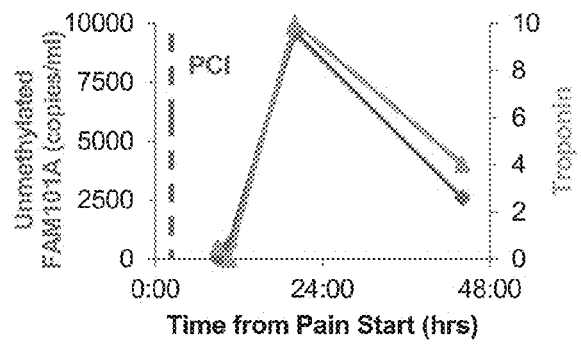
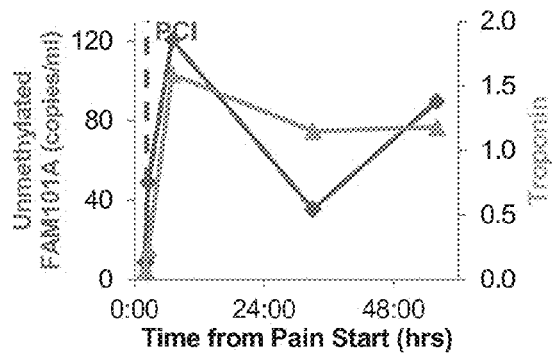
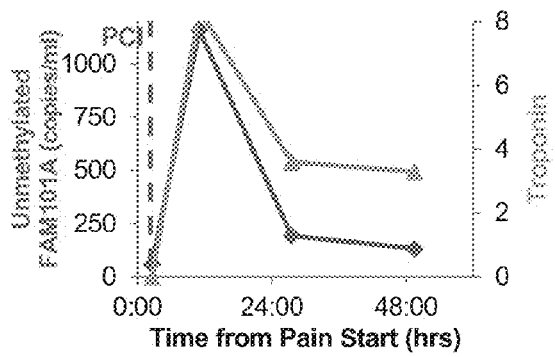

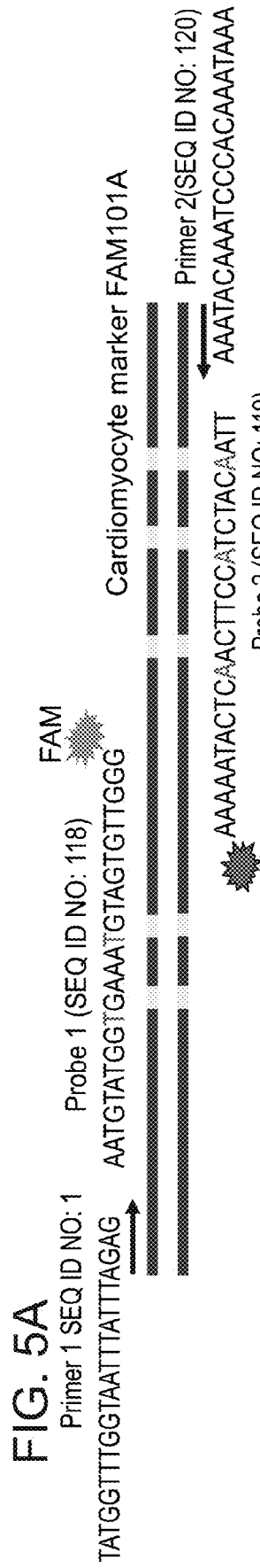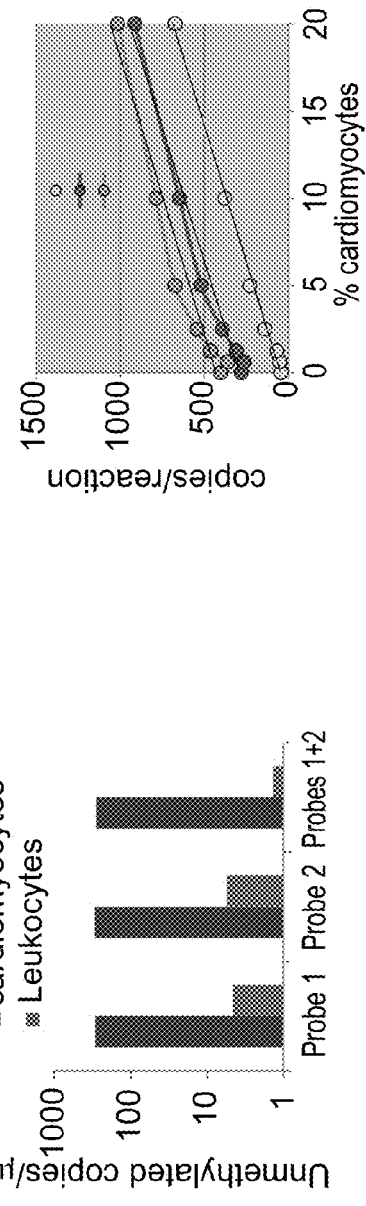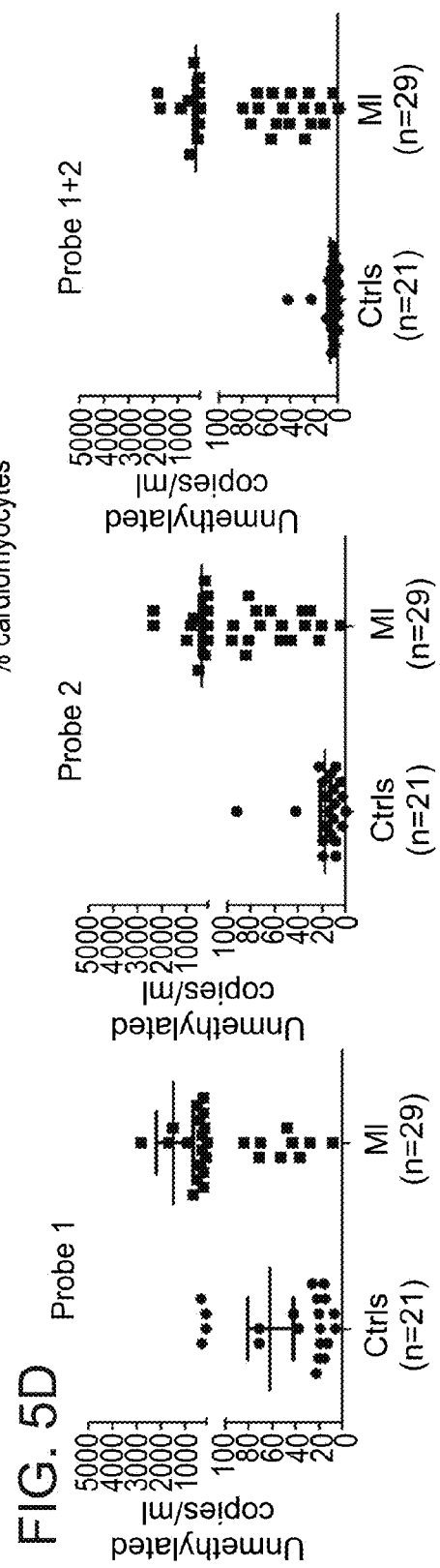

FIG. 12

| | cfDNA extraction | Bisulfite treatment | PCR | Purify product | Analysis of products | Total time |
|---|---|---|---|---|---|---|
| Analysis by Deep sequencing | ~1h (acc to number of samples) | ~3hrs | 3 hrs | 1h | By sequencing (miseq or nextseq) 29hrs | 37 hrs |
| Analysis by ddPCR | | | 2:30 hrs | - | 15 min/8 samples | 6:45 hrs |

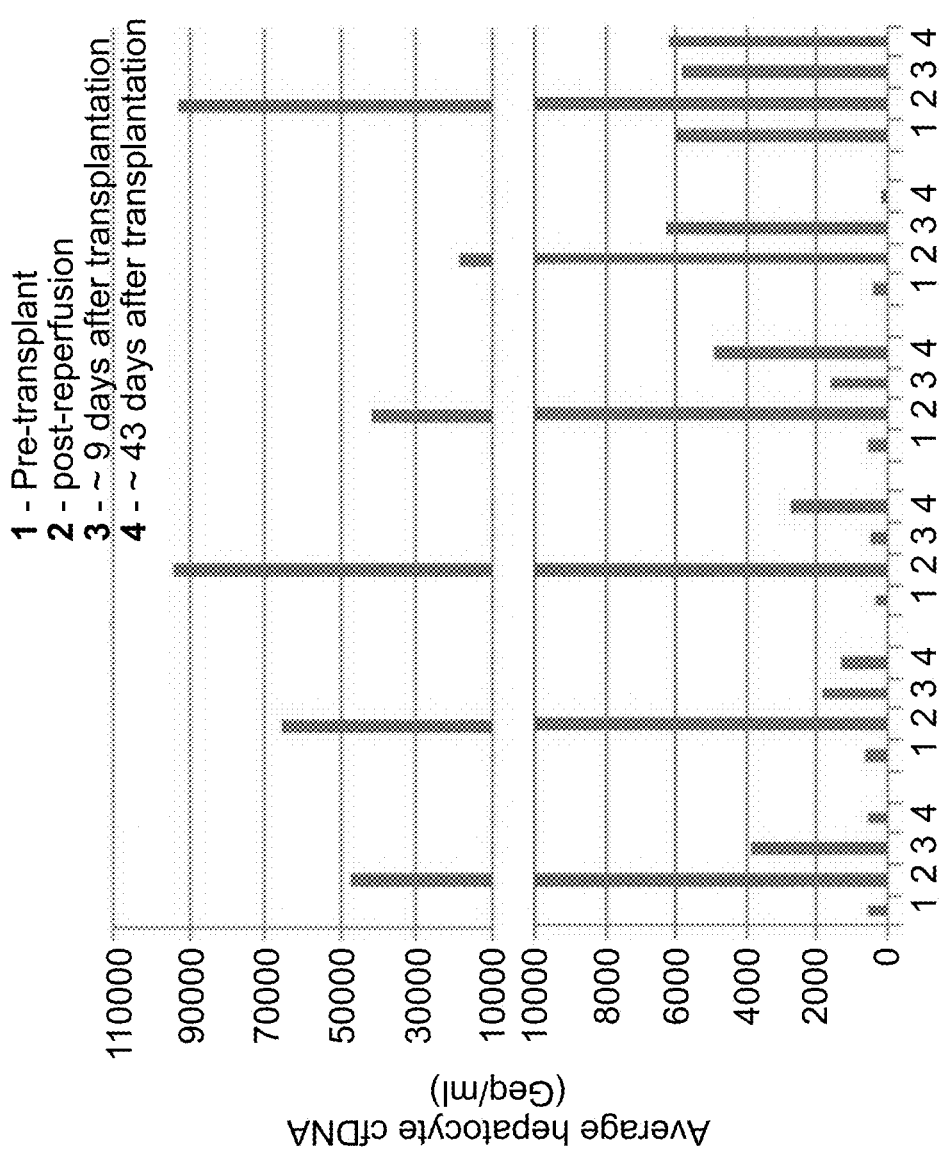
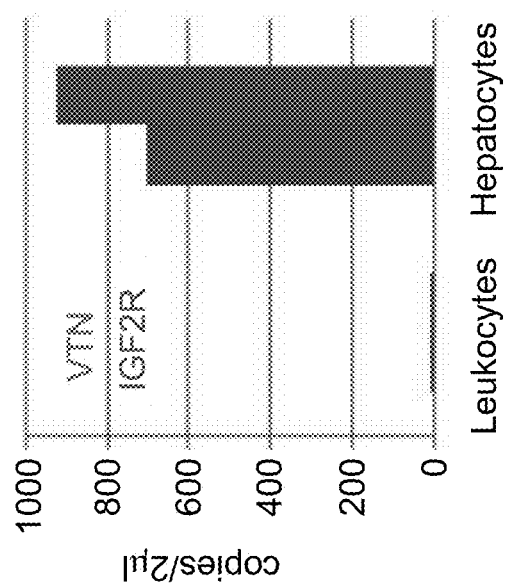

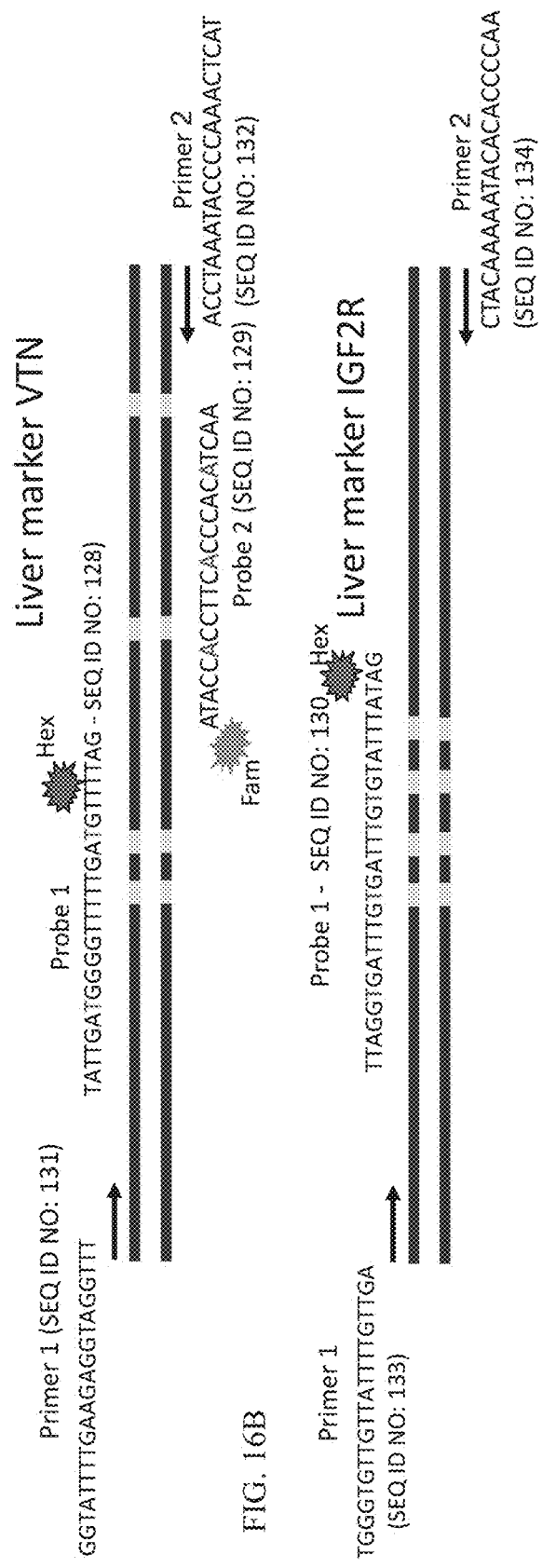

DUAL-PROBE DIGITAL DROPLET PCR STRATEGY FOR SPECIFIC DETECTION OF TISSUE-SPECIFIC CIRCULATING DNA MOLECULES

CROSS-REFERENCE TO RELATED APPLICATIONS

This application is a National Phase of PCT Patent Application No. PCT/IL2018/050772 having International filing date of Jul. 13, 2018, which claims the benefit of priority of U.S. Provisional Patent Application No. 62/531,983, filed on Jul. 13, 2017. The contents of the above applications are all incorporated by reference as if fully set forth herein in their entirety.

FIELD AND BACKGROUND OF THE INVENTION

It has been known for decades that plasma contains small fragments of cell-free circulating DNA (cfDNA) derived from dead cells (on average 1000 genome equivalents per ml). While the mechanisms underlying the release and clearance of cfDNA remain obscure, the phenomenon is rapidly being exploited for a variety of applications with clinical relevance. The recognition that fragments of fetal DNA travel briefly in maternal circulation has opened the way for next generation sequencing (NGS)-based prenatal testing to identify fetal trisomies and other genetic aberrations, potentially replacing amniocentesis. In cancer biology, tumors are known to release DNA (including tumor-specific somatic mutations) into the circulation, providing means for liquid biopsies to monitor tumor dynamics and genomic evolution. In addition, cfDNA has been used to detect graft cell death after kidney, liver or heart transplantation, based on single nucleotide polymorphisms (SNPs) distinguishing the DNA of donor from that of recipients. In all these cases, genetic differences exist between the DNA sequence of the tissue of interest (fetus, tumor or graft) and that of the host, providing the basis for highly specific assays.

Blood levels of cfDNA are known to increase under multiple additional conditions such as traumatic brain injury, cardiovascular disease, sepsis and intensive exercise. However in these cases, the source of elevated cfDNA is unknown, greatly compromising the utility of cfDNA as a diagnostic or prognostic tool. For example, cfDNA could originate from parenchymal cells of the injured tissue, but also from dying inflammatory cells.

Despite having an identical nucleotide sequence, the DNA of each cell type in the body carries unique epigenetic marks correlating with its gene expression profile. In particular, DNA methylation, serving to repress nontranscribed genes, is a fundamental aspect of tissue identity. Methylation patterns are unique to each cell type, conserved among cells of the same type in the same individual and between individuals, and are highly stable under physiologic or pathologic conditions. Therefore, it may be possible to use the DNA methylation pattern of cfDNA to determine its tissue of origin and hence to infer cell death in the source organ.

Theoretically, such an approach could identify the rate of cell death in a tissue of interest, taking into account the total amount of cfDNA, the fraction derived from a tissue of interest, and the estimated half life of cfDNA (15-120 minutes). Note that since the approach relies on normal, stable markers of cell identity, it cannot identify the nature of the pathology (e.g. distinguishing cfDNA derived from dead tumor cells or dead wild type cells due to trauma or inflammation in the same tissue). The potential uses of a highly sensitive, minimally invasive assay of tissue specific cell death include early, precise diagnosis as well as monitoring response to therapy in both a clinical and drug-development setting.

A classic example of tissue-specific DNA methylation is provided by the insulin gene promoter, which is unmethylated in insulin-producing pancreatic (3-cells and methylated elsewhere. Recent studies have identified unmethylated insulin promoter DNA in the circulation of newly diagnosed T1D patients as well as in islet graft recipients, likely reflecting both autoimmune and alloimmune destruction of β cells (Akirav E. M. et al. Proceedings of the National Academy of Sciences of the United States of America, 108, 19018-19023 (2011); Lebastchi J et al., Diabetes 62, 1676-1680 (2013); Husseiny M. I. Plos one 9 e94591 (2014; and Herold K. C. et al., J Clin Invest. Doi:10.1172/jc178142 (2015)).

Droplet Digital PCR technology is a digital PCR method utilizing a water-oil emulsion droplet system. Droplets are formed in a water-oil emulsion to form the partitions that separate the template DNA molecules. The droplets serve essentially the same function as individual test tubes or wells in a plate in which the PCR reaction takes place, albeit in a much smaller format. The massive sample partitioning is a key aspect of the ddPCR technique.

The Droplet Digital PCR System partitions nucleic acid samples into thousands of nanoliter-sized droplets, and PCR amplification is carried out within each droplet. This technique has a smaller sample requirement than other commercially available digital PCR systems, reducing cost and preserving precious samples.

Sample partitioning is the key to droplet digital PCR. In traditional PCR, a single sample offers only a single measurement, but in Droplet Digital PCR, the sample is partitioned into 20,000 nanoliter-sized droplets. This partitioning enables the measurement of thousands of independent amplification events within a single sample.

ddPCR technology uses a combination of microfluidics and proprietary surfactant chemistries to divide PCR samples into water-in-oil droplets. The droplets support PCR amplification of the template molecules they contain and use reagents and workflows similar to those used for most standard TaqMan™ probe-based assays. Following PCR, each droplet is analyzed or read in a flow cytometer to determine the fraction of PCR-positive droplets in the original sample. These data are then analyzed using Poisson statistics to determine the target DNA template concentration in the original sample.

Additional background art includes Bidshahri et al., The Journal of Molecular Diagnostics, Vol. 18, No. 2, March 2016, Usmani-Brown et al., Endocrinology 155: 3694-3698, 2014; International PCT Publication No. WO2013131083, WO 2014138133, WO201101728, WO2015/159292 and WO2015169947.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

SUMMARY OF THE INVENTION

According to an aspect of some embodiments of the present invention there is provided a method of analyzing the methylation status of methylation sites of a double-stranded DNA molecule which comprises at least two methylation sites per single strand of the double-stranded DNA molecule, the double-stranded DNA molecule being comprised in a specimen, the method comprising:
(a) contacting the double-stranded DNA with bisulfite to generate single-stranded DNA molecules of which demethylated cytosines of the single-stranded DNA molecules are converted to uracils;
(b) fractionating the specimen into a plurality of specimen fractions wherein more than 50% of the fractions contain no more than one single-stranded DNA molecule per specimen fraction; and
(c) determining the methylation status of the at least two methylation sites of the single-stranded DNA molecule in at least one of the specimen fractions, wherein a methylation status of each of the at least two methylation sites on the single-stranded DNA molecule is indicative of the methylation status of methylation sites of a double-stranded DNA molecule.

According to an aspect of some embodiments of the present invention there is provided a kit for analyzing methylation sites of a double-stranded DNA molecule, the kit comprising:
(i) a first oligonucleotide probe, wherein the 3' end of the first probe comprises a quenching moiety and the 5' end is labeled with a first detectable moiety;
(ii) a second oligonucleotide probe, wherein the 3' end of the second probe comprises a quenching moiety and the 5' end is labeled with a second detectable moiety;
wherein the sequence of the first probe is selected so as to determine a methylation status at a first methylation site of the double-stranded DNA molecule and the sequence of the second probe is selected so as determine a methylation status at a second methylation site of the same double-stranded DNA molecule, wherein the first methylation site and the second methylation site are no more than 300 base pairs apart; and
(iii) a Taqman™ polymerase.

According to an aspect of some embodiments of the present invention there is provided a kit for analyzing methylation sites of a double-stranded DNA molecule, the kit comprising:
(i) at least two oligonucleotides, wherein the sequence of the first oligonucleotide of the at least two oligonucleotides is selected so as to determine a methylation status at a first methylation site of the double-stranded DNA molecule and the sequence of the second oligonucleotide of the at least two oligonucleotides is selected so as determine a methylation status at a second methylation site of the same double-stranded DNA molecule, wherein the first methylation site and the second methylation site are no more than 300 base pairs apart; and
(ii) a droplet forming oil.

According to some embodiments of the invention, the double-stranded DNA molecule is no longer than 300 base pairs (bp).

According to some embodiments of the invention, the double-stranded DNA molecule is no longer than 150 bp.

According to some embodiments of the invention, the at least two methylation sites are not more than 300 bp apart.

According to some embodiments of the invention, the at least two methylation sites are not more than 150 bp apart.

According to some embodiments of the invention, each strand of the double-stranded DNA comprises at least four methylation sites.

According to some embodiments of the invention, the at least four methylation sites are not more than 300 bp apart.

According to some embodiments of the invention, the at least four methylation sites are not more than 150 bp apart.

According to some embodiments of the invention, the method further comprises contacting the single-stranded DNA with amplification primers under conditions that generate amplified DNA from the single-stranded DNA following step (b) and prior to step (c).

According to some embodiments of the invention, the determining is effected using at least two non-identical labels.

According to some embodiments of the invention, the determining is effected using a single label.

According to some embodiments of the invention, the determining comprises:
(a) contacting the amplified DNA with:
(i) a first probe that hybridizes to the amplified DNA at a site which comprises the first of the at least two methylation sites; and
(ii) a second probe that hybridizes to the amplified DNA at a site which comprises a second of the at least two methylation sites, wherein the first probe and the second probe are labeled with non-identical detectable moieties, wherein the first probe and the second probe comprise a quenching moiety;
wherein the contacting is effected under conditions that separate the quenching moiety from the first probe and the second probe to generate a non-quenched first probe and a non-quenched second probe; and
(b) analyzing the amount of the non-quenched first probe and the non-quenched second probe in at least one specimen fraction of the plurality of specimen fractions.

According to some embodiments of the invention, the determining comprises contacting the amplified DNA with:
(i) a first probe that hybridizes to the amplified DNA at a site which comprises the first of the at least two methylation sites; and
(ii) a second probe that hybridizes to the amplified DNA at a site which comprises a second of the at least two methylation sites, wherein the first probe and the second probe are labeled with non-identical detectable moieties.

According to some embodiments of the invention, the first probe hybridizes to the forward strand of the amplified DNA and the second probe hybridizes to the reverse strand of the amplified DNA.

According to some embodiments of the invention, the double-stranded DNA molecule is differentially methylated in a cell or tissue of interest.

According to some embodiments of the invention, the cell of interest is selected from the group consisting of a pancreatic beta cell, a pancreatic exocrine cell, a hepatocyte, a brain cell, a lung cell, a uterus cell, a kidney cell, a breast cell, an adipocyte, a colon cell, a rectum cell, a cardiomyocyte, a skeletal muscle cell, a prostate cell and a thyroid cell.

According to some embodiments of the invention, the tissue is selected from the group consisting of pancreatic tissue, liver tissue, lung tissue, brain tissue, uterus tissue, renal tissue, breast tissue, fat, colon tissue, rectum tissue, cardiac tissue, skeletal muscle tissue, prostate tissue and thyroid tissue.

According to some embodiments of the invention, the tissue is cardiac tissue.

According to some embodiments of the invention, the double-stranded DNA molecule is non-methylated in cells of cardiac tissue and methylated in leukocytes.

According to some embodiments of the invention, the double-stranded DNA molecule comprises at least a part of the sequence of human chromosome 12, between coordinates 124692462-124692551.

According to some embodiments of the invention, the double stranded DNA molecule comprises a sequence which is comprised in SEQ ID NOs: 56 or 57.

According to some embodiments of the invention, the tissue is liver tissue.

According to some embodiments of the invention, the double-stranded DNA molecule comprises a sequence which is comprised in SEQ ID NOs: 65 or 66.

According to some embodiments of the invention, the first probe comprises a sequence as set forth in SEQ ID NO: 118 and the second probe comprises a sequence as set forth in SEQ ID NO: 119.

According to some embodiments of the invention, the first probe comprises a sequence as set forth in SEQ ID NO: 128 and the second probe comprises a sequence as set forth in SEQ ID NO: 129.

According to some embodiments of the invention, the first probe comprises a sequence as set forth in SEQ ID NO: 125 and the second probe comprises a sequence as set forth in SEQ ID NO: 126.

According to some embodiments of the invention, the single label is comprised on a probe.

According to some embodiments of the invention, the probe comprises a sequence as set forth in SEQ ID NO: 130.

According to some embodiments of the invention, the sequence of the first probe is selected such that the first probe binds to the amplified DNA when the methylation site of the double-stranded DNA molecule is non-methylated.

According to some embodiments of the invention, the sequence of the second probe is selected such that the second probe binds to the amplified DNA when the methylation site of the double-stranded DNA molecule is non-methylated.

According to some embodiments of the invention, the detectable moiety is FAM or HEX.

According to some embodiments of the invention, the double-stranded DNA is cell-free DNA.

According to some embodiments of the invention, the double-stranded DNA is cellular DNA.

According to some embodiments of the invention, the method further comprises lysing the cells of the cellular DNA prior to the determining.

According to some embodiments of the invention, the specimen is a fluid specimen.

According to some embodiments of the invention, the fluid specimen is a body fluid specimen.

According to some embodiments of the invention, the body fluid is selected from the group consisting of blood, plasma, sperm, milk, urine, saliva and cerebral spinal fluid.

According to some embodiments of the invention, the specimen comprises DNA from a plurality of cell-types.

According to some embodiments of the invention, the specimen is blood.

According to some embodiments of the invention, the method further comprises quantitating the amount of DNA of the cell or tissue origin.

According to some embodiments of the invention, the kit further comprises a droplet forming oil.

BRIEF DESCRIPTION OF THE SEVERAL VIEWS OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-E: Identification of cardiomyocyte-specific DNA methylation markers.

Figure 1A:
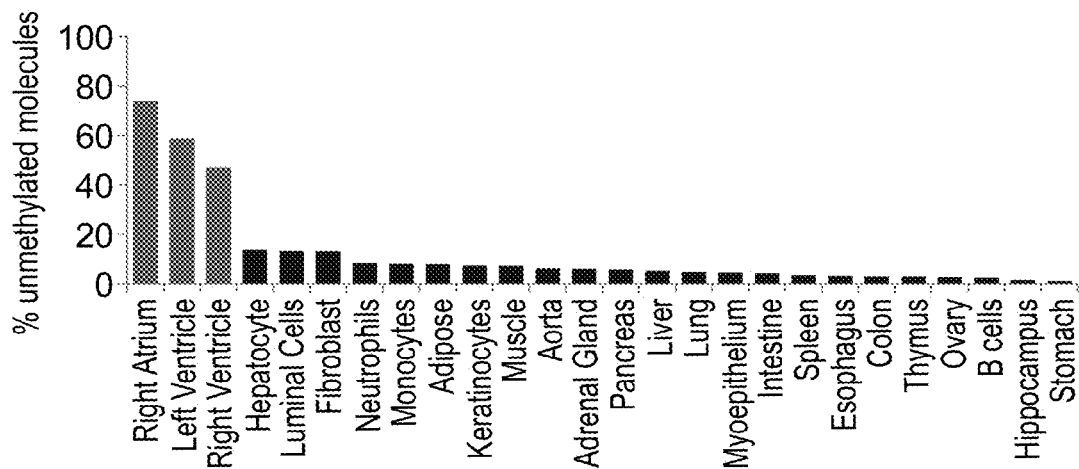

FIG. 1A. Unmethylation levels of FAM101A locus in 27 human tissues, including left ventricle, right ventricle and right atrium (red). Data was extracted from the Roadmap Epigenomics Consortium browser.

Figure 1B:
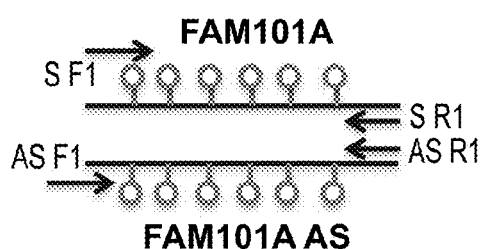

FIG. 1B. Structure of the FAM101A locus, used as two independent markers: FAM101A and FAM101A AS. Lollipops represent CpG sites; arrows mark positions of PCR primers; S, sense marker; AS, antisense marker.

Figure 1C:
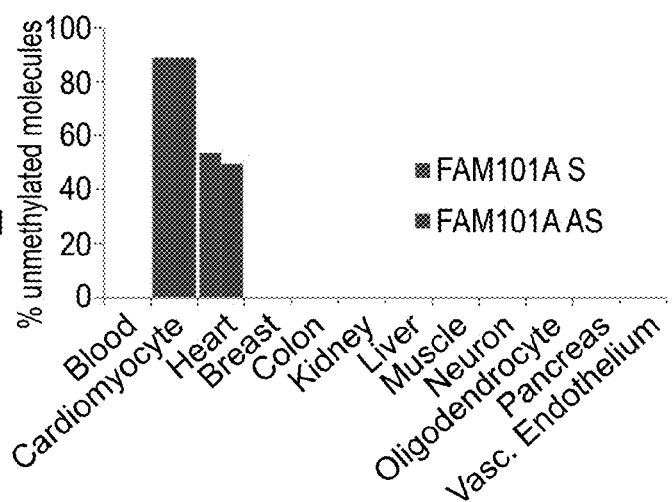

FIG. 1C. Unmethylation status of FAM101A and FAM101A AS in DNA from multiple tissues and from isolated cardiomyocytes (purchased from ScienCell Research Laboratories, San Diego, Calif.). Targeted PCR yields a lower background in non cardiac tissues compared with the Roadmap browser in panel A, since the roadmap data includes molecules that contain only some of the cytosines in the FAM101A locus (e.g. only one or two), which can occasionally be demethylated in non-cardiac tissue. In contrast, the targeted PCR by definition amplifies only molecules containing all cytosines in the locus.

Figure 1D:
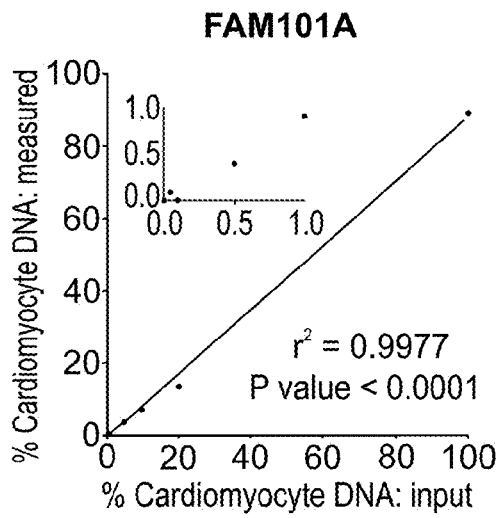
Figure 1E:
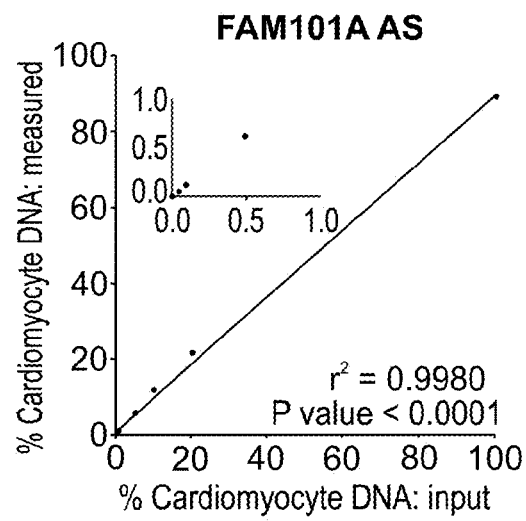

FIGS. 1D-E. Spike in experiments for FAM101A and FAM101A AS. Human cardiomyocyte DNA was mixed with human leukocyte DNA in the indicated proportions (0-100%), and the percentage of fully unmethylated FAM101A molecules (in which all five CpG sites were converted by bisulfate) was determined.

FIGS. 2A-F: Cardiomyocyte-derived cfDNA in healthy subjects and in patients with myocardial infarction.

Figure 2A:
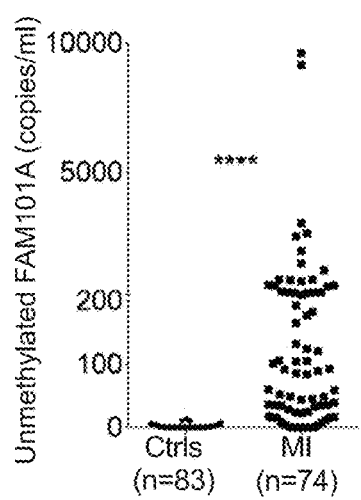

FIG. 2A. Cardiac cfDNA (copies of fully unmethylated FAM101A/ml plasma) in specimens from healthy controls (n=61) and patients during MI (n=79). Mann-Whitney test for controls vs. patients, P<0.0001

Figure 2B:
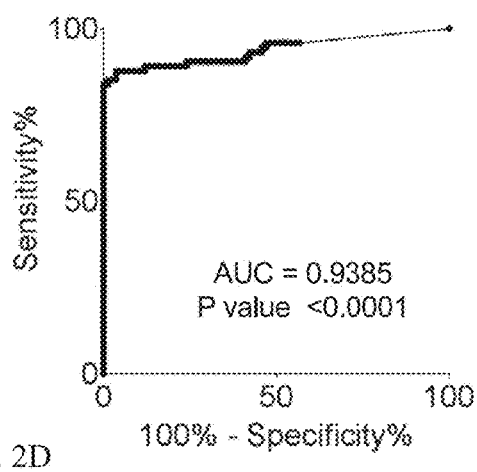

FIG. 2B. Receiver operating characteristic (ROC) curve for unmethylated FAM101A levels in healthy controls and patients with MI. Area under the curve (AUC) 0.884 (95% CI=0.8925 to 0.9766)

Figure 2C:
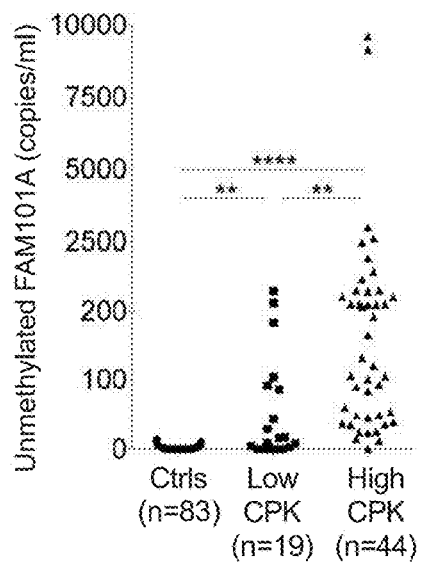

FIG. 2C. Comparison of unmethylated FAM101A levels (copies/ml) in samples from healthy controls, MI patients with low Creatine Kinase (CPK<200) and MI patients with high CK (CK>200). Kruskal-Wallis test P value<0.0001. Dunn's multiple comparisons test adjusted P Value: Ctrls vs. low CK, p<0.001; Ctrls vs. high CK, P<0.0001; low CK vs. high CK, P=0.0064.

Figure 2D:
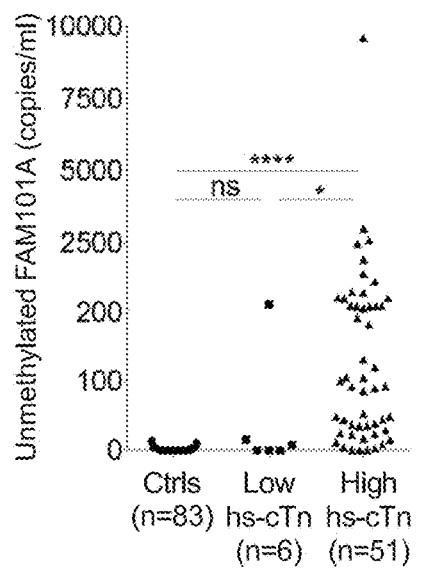

FIG. 2D. Comparison of unmethylated FAM101A levels in samples from healthy controls, MI patients with low levels of high-sensitive troponin T (hs-cTn) (<0.03), and MI patients with high levels of hs-cTn (>0.03). Dunn's multiple comparisons test adjusted P Value: Ctrls vs. low hs-cTn (<0.03), P=0.8645; Ctrls vs. high hs-cTn (>0.03), PV<0.0001; low hs-cTn (<0.03) vs. high hs-cTn (>0.03), P=0.0189.

Figure 2E:
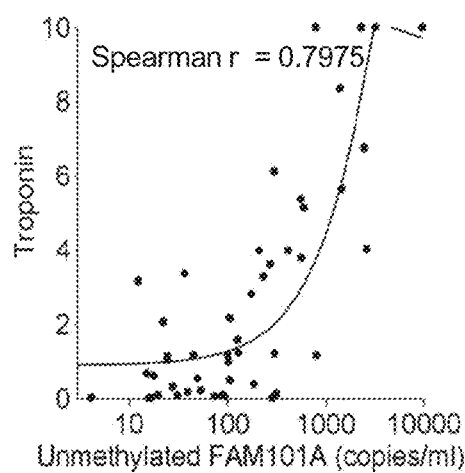

FIG. 2E. Spearman correlation between cardiac cfDNA and troponin levels in n=57 specimens.

Figure 2F:
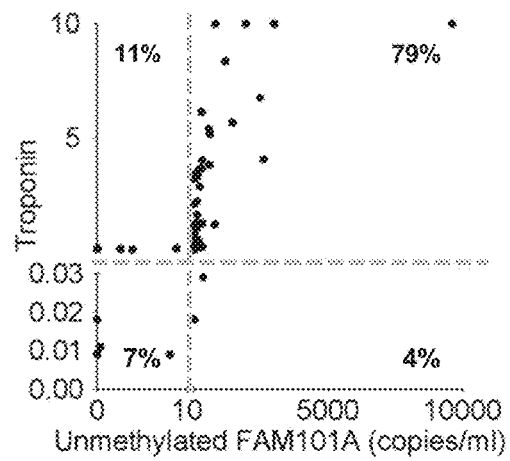

FIG. 2F. XY Scatter plot for cardiac cfDNA levels vs. cardiac troponin. Quadrants indicate negative and positive hs-Tn, and negative and positive cardiac cfDNA. Numbers indicate the percentage of specimens in each quadrant.

FIGS. 3A-C: Cardiac cfDNA dynamics during MI and after angioplasty.

FIG. 3A. Cardiac cfDNA levels in MI patients before and after PCI.

FIG. 3B. ROC curve for cardiac cfDNA in healthy individuals versus MI patients prior to intervention.

FIG. 3C. Time course of cardiac cfDNA and troponin levels in five patients. Vertical dashed lines indicate PCI time.

Figure 4A:
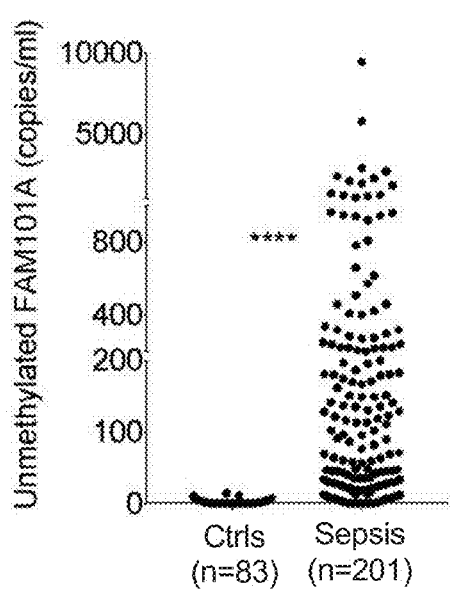
Figure 4B:
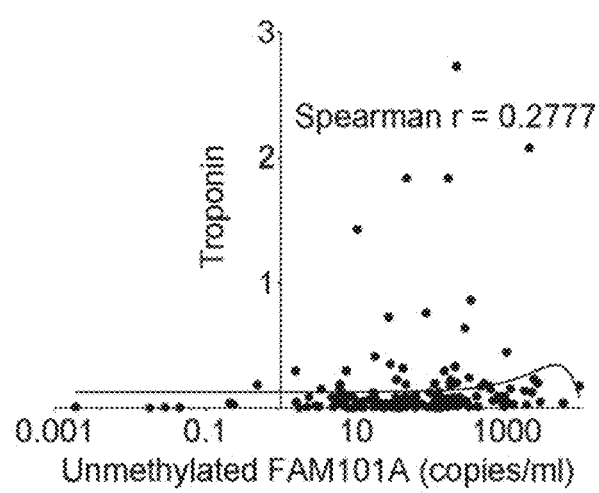
Figure 4C:
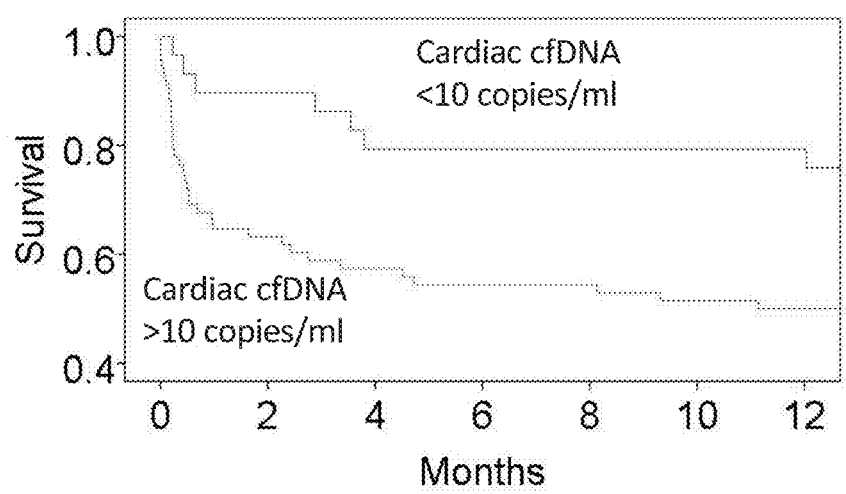

FIGS. 4A-C: Cardiac cfDNA in sepsis.

FIG. 4A. Levels of cardiac cfDNA in healthy controls and patients with sepsis.

FIG. 4B. Lack of correlation between cardiac cfDNA and troponin. Curved line represents non linear (quadratic) fit.

FIG. 4C. Kaplan-Meier plot showing correlation of cardiac cfDNA to patient survival.

FIGS. 5A-D: An exemplary method for detecting cardiac cfDNA using digital droplet PCR, according to embodiments of the present invention.

FIG. 5A. Schematic of approach for ddPCR-based detection of methylation status of multiple adjacent cytosines. A signal from two probes in the same droplet reflects lack of methylation in 5 adjacent cytosines in the same original DNA strand.

FIG. 5B. Signal from cardiomyocyte and leukocyte DNA based on individual or dual probes. Scoring only dual probe signals drastically reduces noise from leukocyte DNA.

FIG. 5C. Spike-in experiment assessing sensitivity and linearity of signal from cardiomyocyte DNA diluted in leukocyte DNA. The use of dual probe enhances linearity and reduces baseline signal.

FIG. 5D. Measurement of cardiac cfDNA in plasma of healthy adults and patients with myocardial infarction. The use of dual probes reduces the baseline signal in healthy plasma.

Figure 6A:
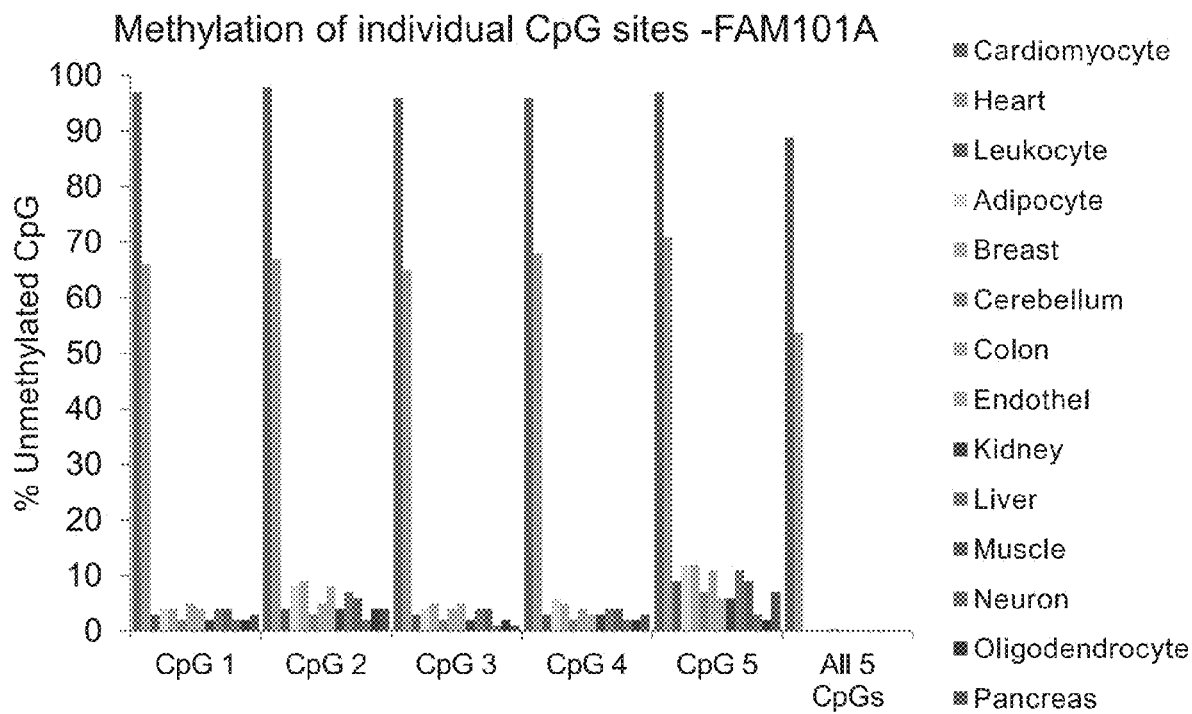
Figure 6B:
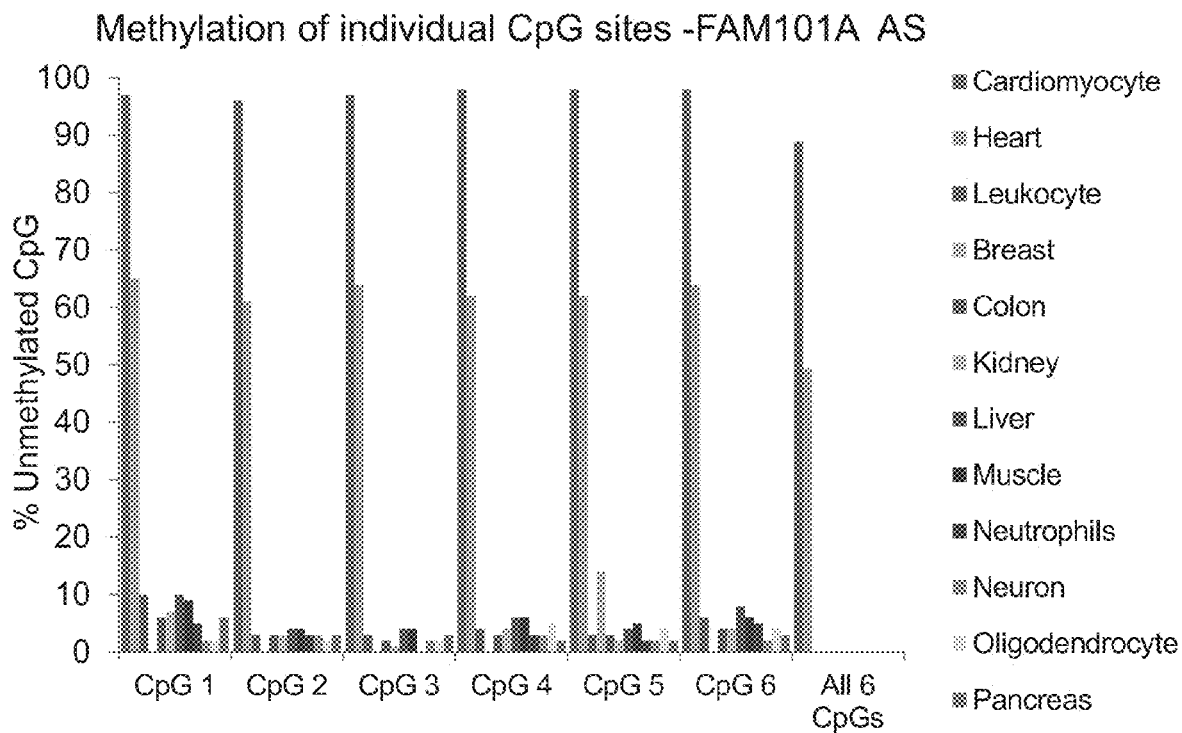
Figure 6C:
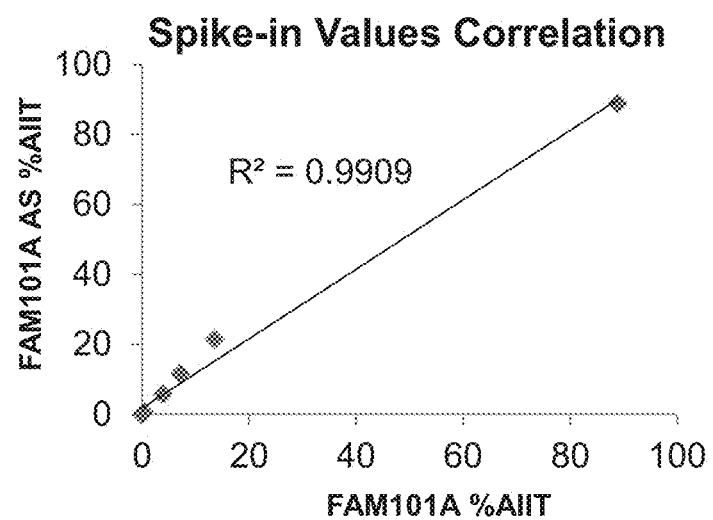

FIGS. 6A-C: methylation of individual and multiple adjacent cytosines within the FAM101A locus.

FIG. 6A. Methylation status of cytosines in the sense strand of FAM101A

FIG. 6B. Metylation status of cytosines in the antisense (AS) strand of FAM101A. Graphs show the percentage of unmethylated molecules in DNA from each tissue. The set of columns on the far right describes the percentage of molecules in which all CpG sites are unmethylated, demonstrating the higher signal-to-noise ratio afforded by interrogating all CpGs simultaneously.

FIG. 6C. Correlation between results of spike-in experiments using the sense and antisense FAM101A markers.

FIGS. 7A-F: additional correlations of cardiac and total cfDNA in MI patients.

Figure 7A:
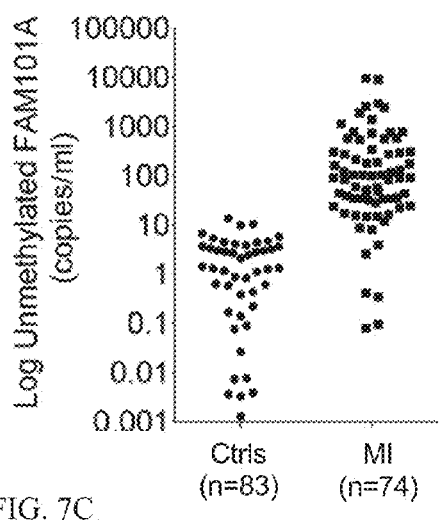

FIG. 7A. Log scale presentation of unmethylated FAM101A levels in plasma specimens from healthy controls (n=83) and patients during MI (n=74). 54 values were zero, so are not shown in the graph.

Figure 7B:
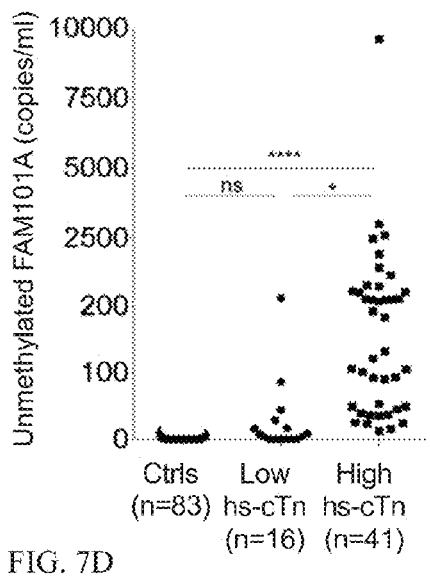

FIG. 7B. Cardiac cfDNA levels in controls vs MI patients positive or negative for high sensitive troponin using 0.1 as a cutoff. Dunn's multiple comparisons test adjusted P value:
Ctrls vs. Low hs-cTn (<0.1), P=0.0433; Ctrls vs. High hs-cTn (>0.1), P<0.0001; Low hs-cTn (<0.1) vs. High hs-cTn (>0.1), P=0.0003.

Figure 7C:
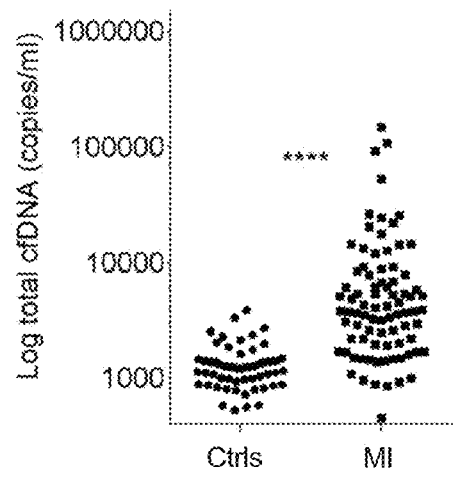

FIG. 7C. Total cfDNA concentration in controls and MI patients.

Figure 7D:
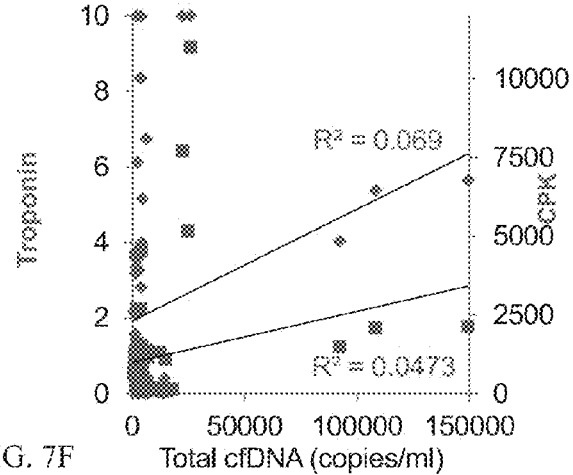

FIG. 7D. Lack of correlation between total concentration of cfDNA (genome equivalents/ml) and either hs-Tn (blue) or CK (red) levels.

Figure 7E:
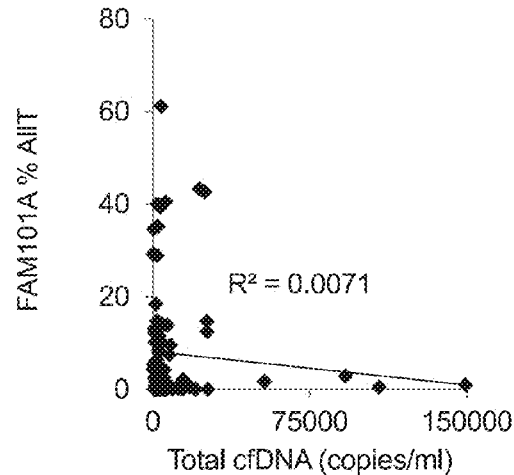

FIG. 7E. Lack of correlation between total cfDNA (genome equivalents/ml) and percentage of cardiac cfDNA.

Figure 7F:
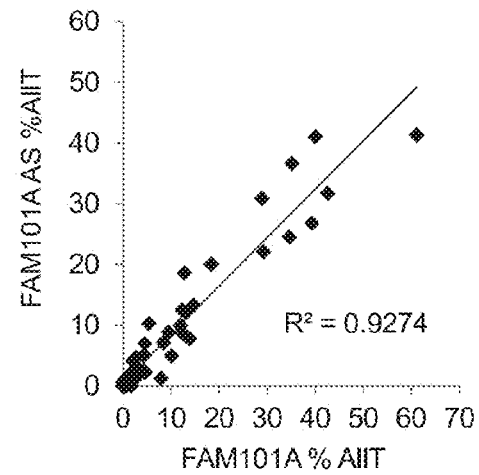

FIG. 7F. Linear correlation between FAM101A sense (S) and antisense (AS) signal in the MI specimens.

Figure 8A:
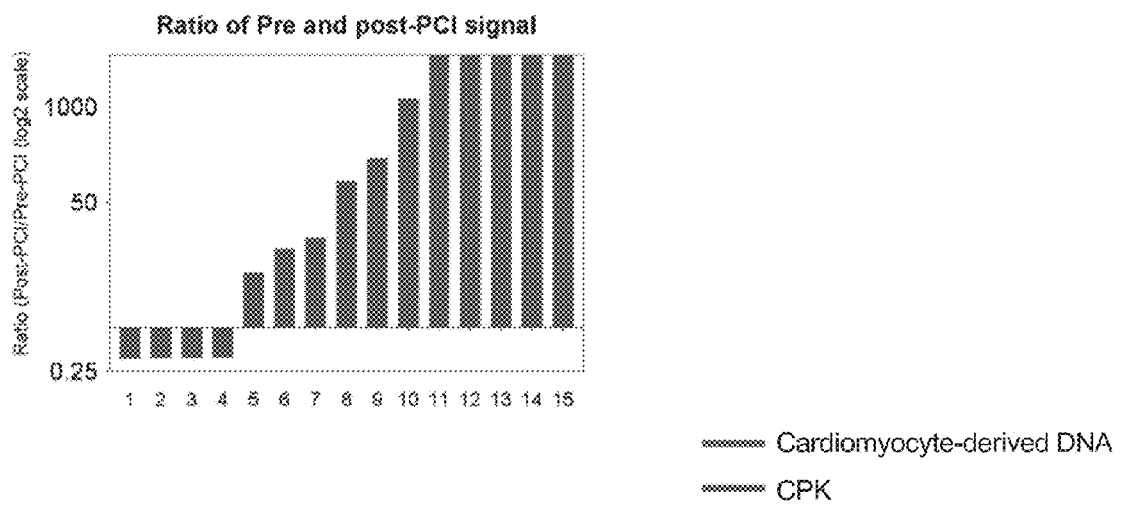
Figure 8B:
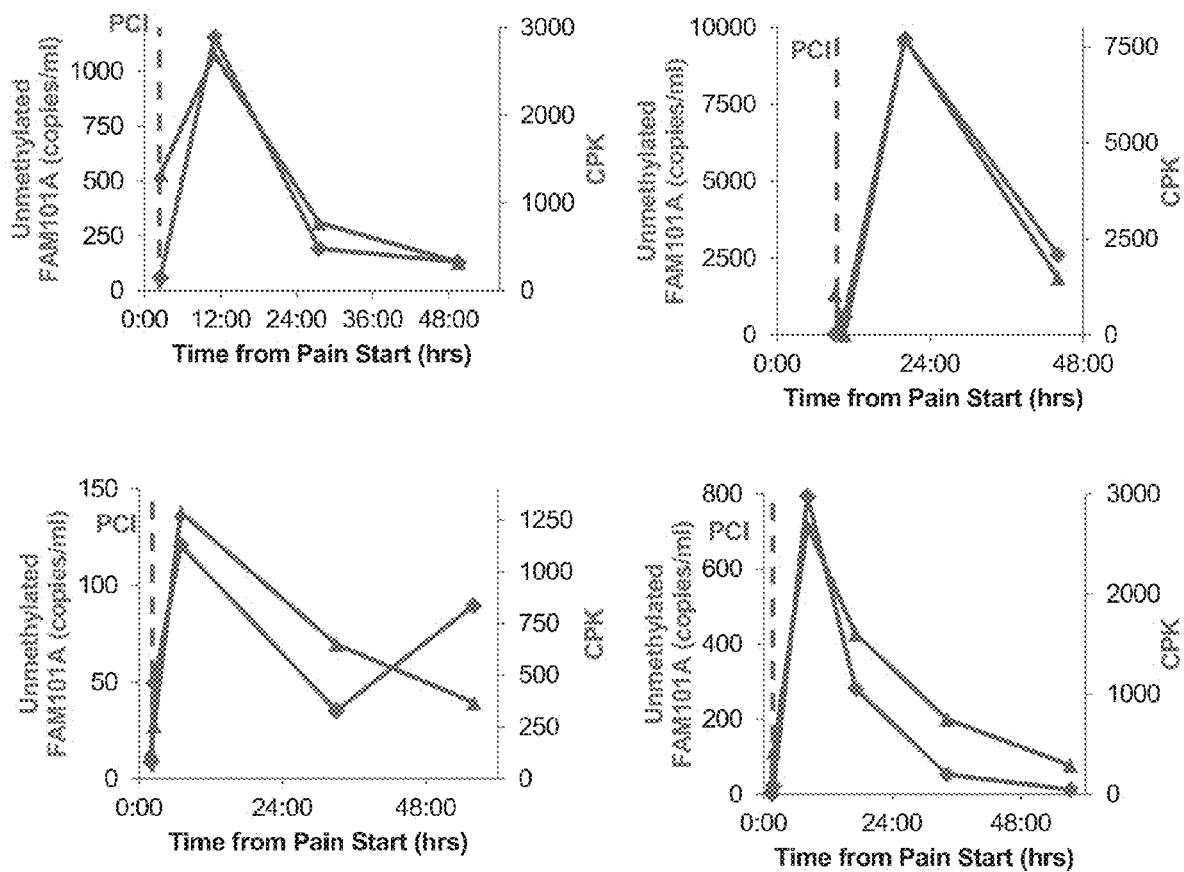

FIGS. 8A-B. Dynamics of cardiac cfDNA and CPK in myocardial infarction.

FIG. 8A. Ratio of cardiac cfDNA before and after PCI in 15 individuals with MI. As expected, cardiac cfDNA levels increased after intervention.

FIG. 8B. Dynamics of cardiac cfDNA and CPK in individual patients. Time 0 is the beginning of chest pain. Vertical dashed line indicates time of PCI.

Figure 9A:
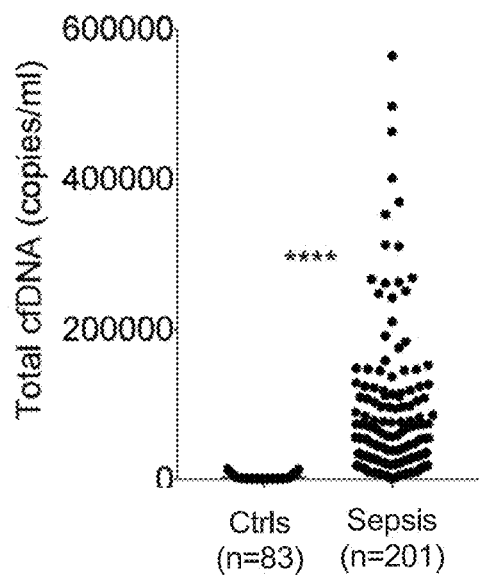
Figure 9B:
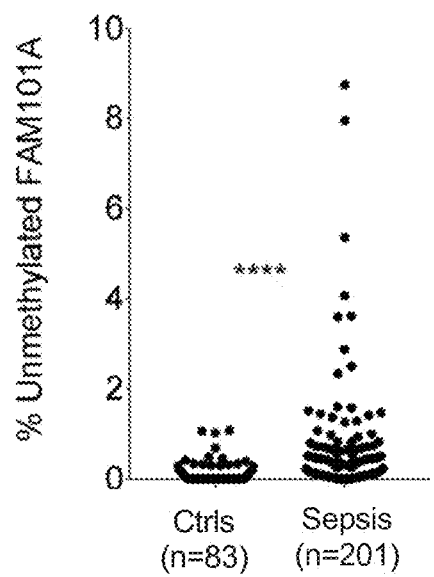
Figure 9C:
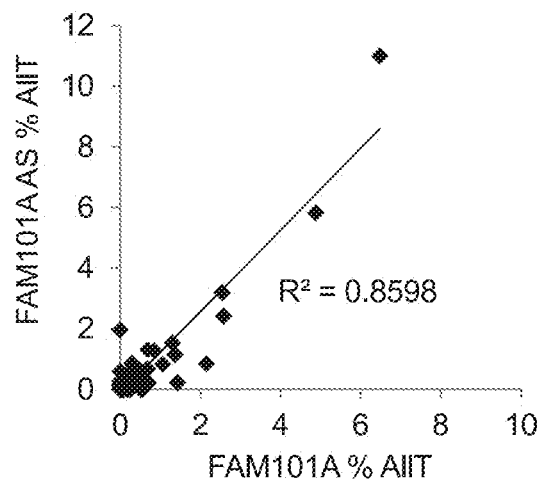

FIGS. 9A-C: Total and cardiac cfDNA levels in patients with sepsis.

FIG. 9A. Concentration of cfDNA in patients with sepsis.

FIG. 9B. Percentage of cardiac cfDNA in patients with sepsis.

FIG. 9C. Correlation between FAM101A sense and antisense signals in sepsis specimens.

Figure 10:
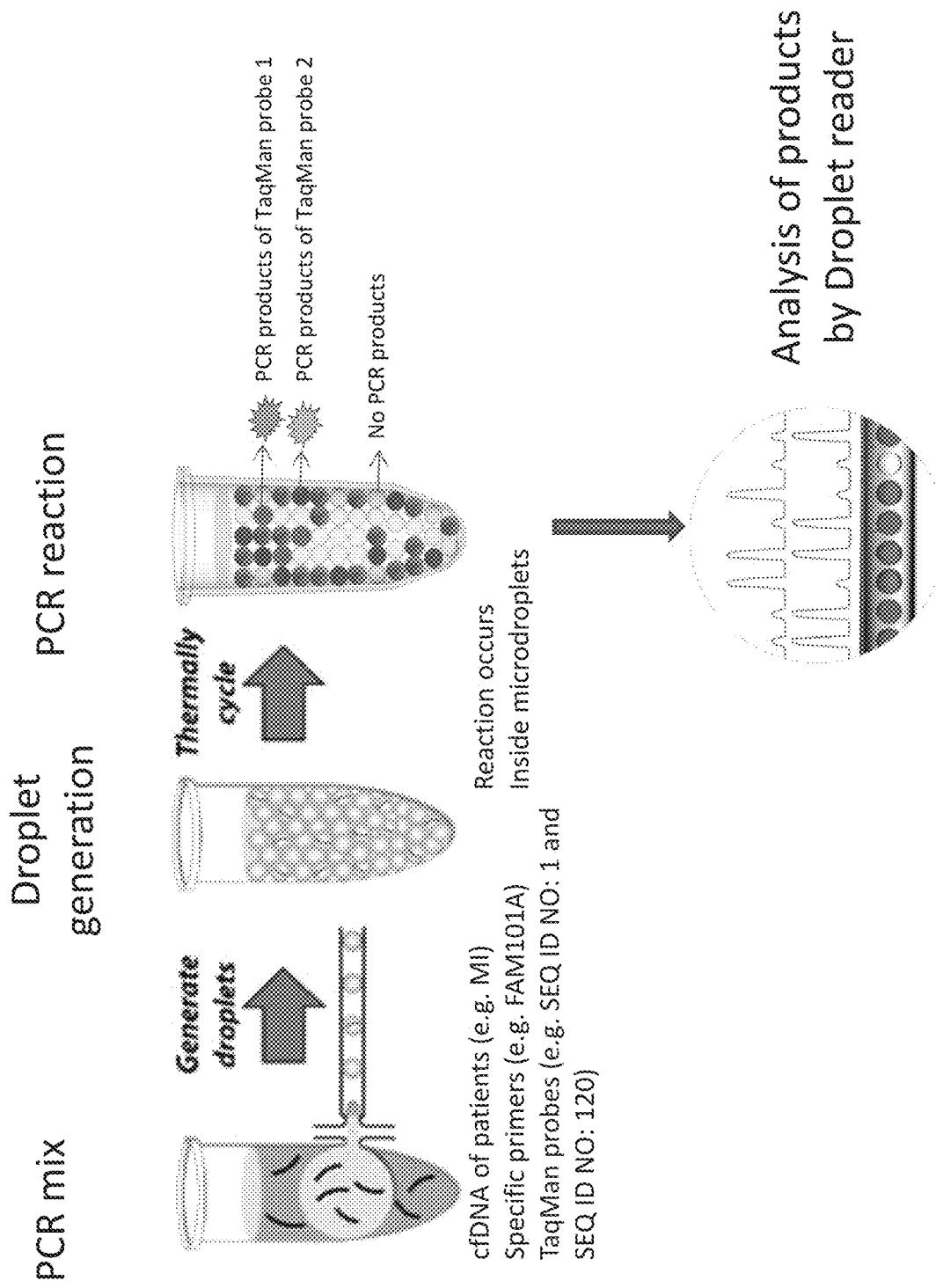

FIG. 10 is a pictorial representation of ddPCR technology.

Figure 11:
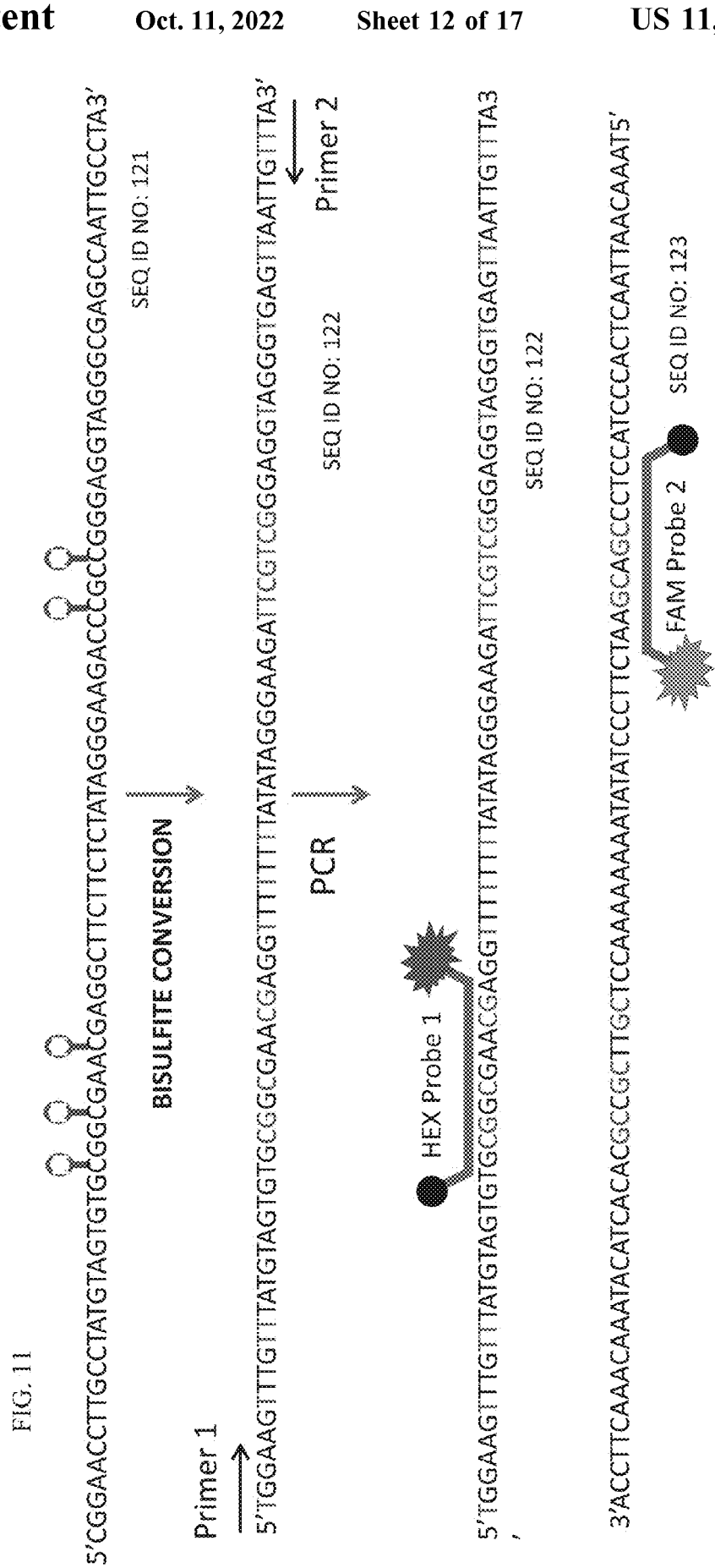

FIG. 11 is a pictorial representation of an assay according to embodiments of the present invention. The figure illustrates the use of two probes (red and green) to define methylation status of two clusters of CpGs on the same DNA molecule in the same droplet.

FIG. 12 is a table comparing the time it takes to analyse methylation status by sequencing and by ddPCR.

Figure 13A:
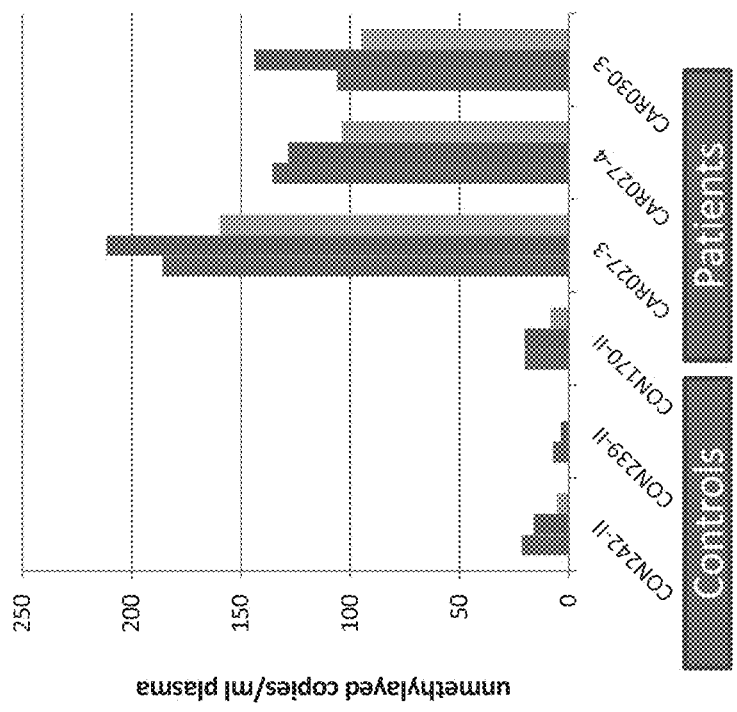
Figure 13B:
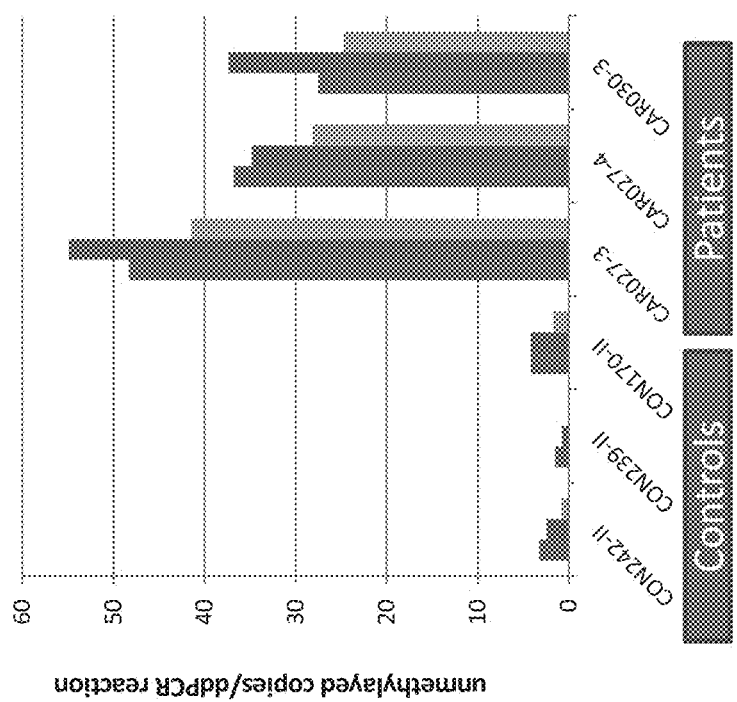

FIGS. 13A-B are bar graphs illustrating how ddPCR may be used to diagnose patients with a myocardial infarction.

FIGS. 14A-B illustrate digital droplet PCR for the identification of liver-derived cfDNA according to embodiments of the present invention.

A. Hepatocyte and leukocyte DNA examined using ddPCR. B. Hepatocyte-derived DNA in the plasma of six liver transplant recipients. Each patient was sampled at four time points as indicated. Graph shows the average values of the two liver markers in each sample.

Figure 15A:
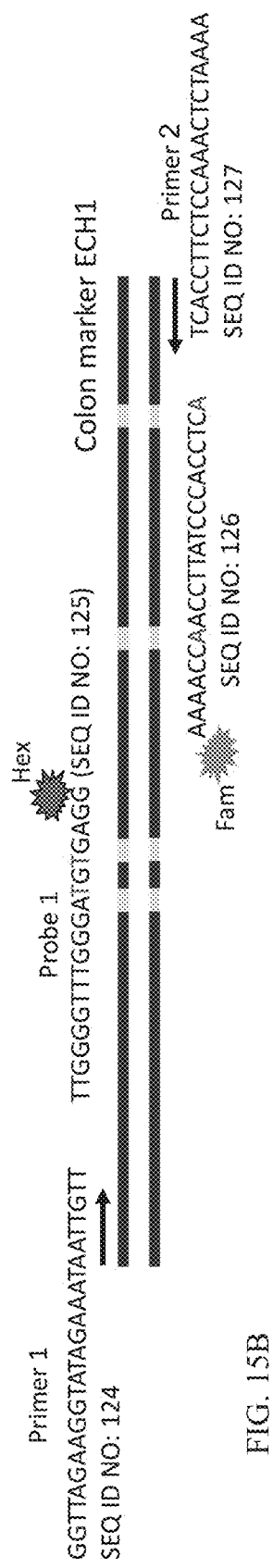
Figure 15B:
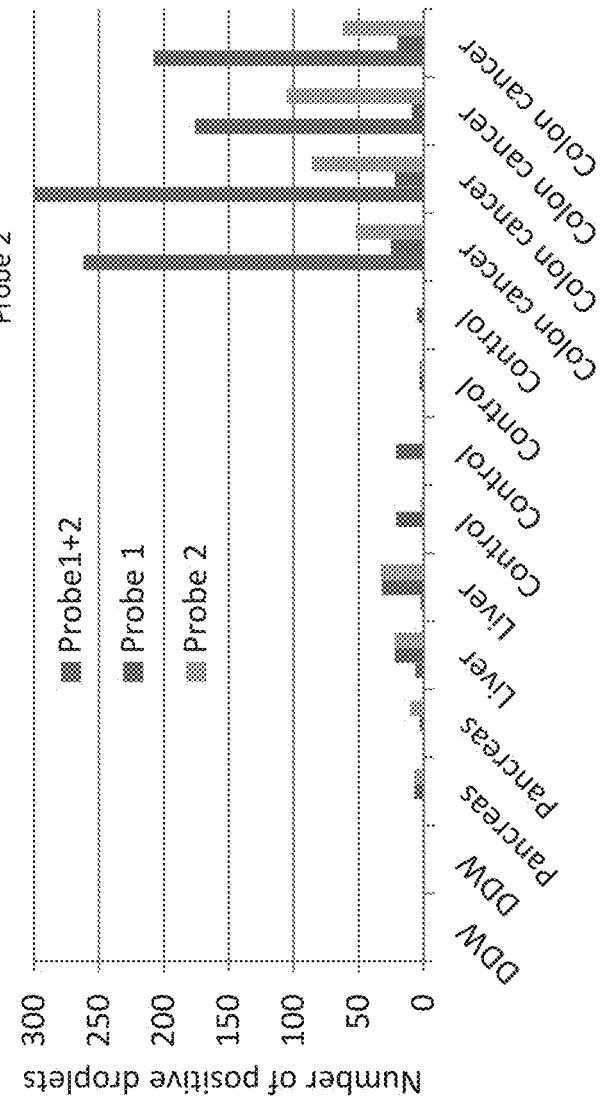

FIGS. 15A-B illustrate digital droplet PCR for the identification of colon-derived cfDNA in plasma samples. ddPCR using both amplicons showed no signal in pancreas, liver, cfDNA from healthy controls DNA and a strong signal in cfDNA of patients with colorectal cancer.

FIGS. 16A-B illustrates digital droplet PCR for the identification of liver-derived cfDNA according to embodiments of the present invention.

DESCRIPTION OF SPECIFIC EMBODIMENTS OF THE INVENTION

The present invention contemplates using digital droplet PCR (ddPCR) for analyzing the methylation status of single DNA molecules. In particular, the method can be used to detect tissue-specific methylation markers.

Analysis of circulating DNA is beginning to revolutionize prenatal diagnosis, tumor diagnosis and the monitoring of graft rejection. However a major limitation of all applications is the dependence on the presence of identifiable genetic differences between the tissue of interest and the host.

Until presently, analysis of tissue-specific methylation patterns present in circulating DNA fragments were performed using massively parallel sequencing, requiring access to a next generation sequencer and the application of a bioinformatics pipeline to interpret sequencing results.

The present inventors have now simplified the method by alleviating the need for sequencing, whilst maintaining accuracy and reliability. The novel method which relies on digital droplet polymerase chain reaction (ddPCR; an overview of which is presented in FIG. 10), reduced the level of false positives to such an extent that clinical utility can now be envisaged.

Using primers for digital droplet PCR (ddPCR) after bisulfite conversion of cfDNA, and fluorescent probes that recognize blocks of unmethylated CpGs in the amplified marker regions, the present inventors have shown that methylation status of clusters of CpG sites (comprising at least two, and preferably at least three, or even at least four CpG sites) in the same molecule can be scored.

FIG. 11 illustrates the use of two probes (red and green) to define the methylation status of two clusters of CpGs on the same DNA molecule in the same droplet.

The increased specificity of the technique is illustrated in FIG. 5B. The number of droplets positive for each individual probe (HEX probe and FAM probe) demonstrated that it is possible to discriminate between cardiac and blood DNA. But when scoring for droplets that are positive for both probes (that is, unmethylated in all 5 CpG sites tested), the noise from blood (red bar) was reduced dramatically and accuracy was increased dramatically.

The present inventors propose that ddPCR (as compared to sequencing) for identification of the methylation status of cfDNA will radically reduce the time from drawing blood to results, from 36 hours today to 7 hours, and potentially much less if rapid PCR machines are used. Comparison of the time needed to analyze methylation status by sequencing or by ddPCR is to summarized in FIG. 12.

Whilst further reducing the present invention to practice, the present inventors have shown that the ddPCR protocol could successfully diagnose myocardial infarction patients (FIGS. 13A-B). In addition, the present inventors have shown that the ddPCR protocol could successfully diagnose liver damage (FIGS. 14A-B) and colon cancer (FIGS. 15A-B).

Thus, according to a first aspect of the present invention there is provided a method of analyzing the methylation status of methylation sites of a double-stranded DNA molecule which comprises at least two methylation sites per single strand of said double-stranded DNA molecule, the double-stranded DNA molecule being comprised in a specimen, the method comprising:
(a) contacting the double-stranded DNA with bisulfite to generate single-stranded DNA molecules of which demethylated cytosines of said single-stranded DNA molecules are converted to uracils;
(b) fractionating the specimen into a plurality of specimen fractions wherein more than 50% of the fractions contain no more than one single-stranded DNA molecule per specimen fraction; and
(c) determining the methylation status of said at least two methylation sites of said single-stranded DNA molecule in at least one of said specimen fractions, wherein a methylation status of each of said at least two methylation sites on said single-stranded DNA molecule is indicative of the methylation status of methylation sites of a double-stranded DNA molecule.

As used herein, the term "methylation status" refers to the status of a cytosine in a DNA sequence. The cytosine may be methylated (and present as 5-methylcytosine) or non-methylated and present as cytosine.

As used herein, the term "methylation site" refers to a cytosine residue adjacent to guanine residue (CpG site) that has a potential of being methylated.

The DNA molecule which is analyzed is preferably no longer than 300 nucleotides, 295 nucleotides, 290 nucleotides, 285 nucleotides, 280 nucleotides, 275 nucleotides, 270 nucleotides, 265 nucleotides, 260 nucleotides, 255 nucleotides, 250 nucleotides, 245 nucleotides, 240 nucleotides, 235 nucleotides, 230 nucleotides, 225 nucleotides, 220 nucleotides, 215 nucleotides, 210 nucleotides, 205 nucleotides, 200 nucleotides, 195 nucleotides, 190 nucleotides, 185 nucleotides, 180 nucleotides, 175 nucleotides, 170 nucleotides, 165 nucleotides, 160 nucleotides, 155 nucleotides, 150 nucleotides, 145 nucleotides, 140 nucleotides, 135 nucleotides, 130 nucleotides, 125 nucleotides, 120 nucleotides, 115 nucleotides, 110 nucleotides, 105 nucleotides, 100 nucleotides, 95 nucleotides, 90 nucleotides, 85 nucleotides, 80 nucleotides, 75 nucleotides, 70 nucleotides, 65 nucleotides, 60 nucleotides, 55 nucleotides, or 50 nucleotides.

According to a particular embodiment, the DNA molecule is between 50-300 nucleotides, e.g. between 50-250, between 50-200, between 100-300, or between 100-250 nucleotides.

In another embodiment, the methylation sites of a methylation signature which are analyzed on a double stranded molecule are no more than 300 nucleotides apart, 295 nucleotides apart, 290 nucleotides apart, 285 nucleotides apart, 280 nucleotides apart, 275 nucleotides apart, 270 nucleotides apart, 265 nucleotides apart, 260 nucleotides apart, 255 nucleotides apart, 250 nucleotides apart, 245 nucleotides apart, 240 nucleotides apart, 235 nucleotides apart, 230 nucleotides apart, 225 nucleotides apart, 220 nucleotides apart, 215 nucleotides apart, 210 nucleotides apart, 205 nucleotides apart, 200 nucleotides apart, 195 nucleotides apart, 190 nucleotides apart, 185 nucleotides apart, 180 nucleotides apart, 175 nucleotides apart, 170 nucleotides apart, 165 nucleotides apart, 160 nucleotides apart, 155 nucleotides apart, 150 nucleotides apart, 145 nucleotides apart, 140 nucleotides apart, 135 nucleotides apart, 130 nucleotides apart, 125 nucleotides apart, 120 nucleotides apart, 115 nucleotides apart, 110 nucleotides apart, 105 nucleotides apart, 100 nucleotides apart, 95 nucleotides apart, 90 nucleotides apart, 85 nucleotides apart, 80 nucleotides apart, 75 nucleotides apart, 70 nucleotides apart, 65 nucleotides apart, 60 nucleotides apart, 55 nucleotides apart, or 50 nucleotides apart.

The sequence of the DNA may be of a coding or non-coding region.

According to a particular embodiment, the sequence is not derived from a gene which is differentially expressed in the cell of interest. Thus, for example in the case of identifying a methylation pattern for a pancreatic beta cell, it is preferable that the DNA sequence is not part of a gene encoding insulin or another pancreatic beta cell protein.

In accordance with another particular embodiment, the methylation pattern characterizes the normal cell of interest and is not a methylation pattern characterizing a diseased cell (is not for example a methylation pattern characterizing cancer cells of a specific type).

The method of the present invention contemplates analyzing at least 2, at least 3, at least 4, at least 5, at least 6, at least 7 at least 8, at least 9 or even at least 10 or more methylation sites of a double-stranded DNA molecule.

Thus, the methylation signature of a double-stranded DNA molecule may comprise at least 2, at least 3, at least 4 at least 5, at least 6, at least 7 at least 8, at least 9 or even at least 10 or more methylation sites.

In order to be considered a methylation signature for a particular cell of interest each of the methylation sites of the signature on the DNA molecule should be differentially methylated in that cell of interest with respect to a second non-identical cell. The methylation signature comprises the methylation status of at least two, at least three, at least four methylation sites of a particular DNA molecule. The methylation sites may be on a single strand of the DNA molecule or distributed amongst both strands of the DNA molecule.

According to a particular embodiment, each of the at least two, three, four or more methylation sites of the signature are unmethylated in the cell of interest (the cell for which the methylation pattern is being determined) on the DNA molecule, whereas in the second non-identical cell each of the sites are methylated on the DNA molecule.

According to another embodiment, each of the at least two, three, four or more methylation sites of the signature are methylated in the cell of interest on the DNA molecule, whereas in the second non-identical cell each of the sites are unmethylated on the DNA molecule.

According to another embodiment, at least one of the methylation sites of the signature is unmethylated in the cell of interest on the DNA molecule, whereas in the second non-identical cell that site is methylated on the DNA molecule.

According to another embodiment, at least one of the methylation sites of the signature is methylated in the cell of interest on the DNA molecule, whereas in the second non-identical cell that site is unmethylated on the DNA molecule.

According to another embodiment, at least two methylation sites of the signature are unmethylated in the cell of interest on the DNA molecule, whereas in the second non-identical cell those sites are methylated on the DNA molecule.

According to another embodiment, at least two methylation sites of the signature are methylated in the cell of interest on the DNA molecule, whereas in the second non-identical cell those sites are unmethylated on the DNA molecule.

According to another embodiment, at least three methylation sites of the signature are unmethylated in the cell of interest on the DNA molecule, whereas in the second non-identical cell those sites are methylated on the DNA molecule.

According to another embodiment, at least three methylation sites of the signature are methylated in the cell of interest on the DNA molecule, whereas in the second non-identical cell those sites are unmethylated on the DNA molecule.

According to another embodiment, at least four methylation sites of the signature are unmethylated in the cell of interest on the DNA molecule, whereas in the second non-identical cell those sites are methylated on the DNA molecule.

According to another embodiment, at least four methylation sites of the signature are methylated in the cell of interest on the DNA molecule, whereas in the second non-identical cell those sites are unmethylated on the DNA molecule.

The second, non-identical cell may be of any source including for example blood cells. Typically, the non-identical cell is one which is comprised in the specimen/sample being analyzed.

The method can be used for identifying methylation signatures of any cell of interest, including but not limited to cardiac cells (e.g. cardiomyocytes), pancreatic cells (such as pancreatic beta cells, exocrine pancreatic cells (e.g. acinar cells), brain cells, oligodendrocytes, liver cells (hepatocytes), kidney cells, tongue cells, vascular endothelial cells, lymphocytes, neutrophils, melanocytes, T-regs, lung cells, a uterus cells, breast cells, adipocytes, colon cells, rectum cells, prostate cells, thyroid cells and skeletal muscle cells. Specimens which may be analyzed are generally fluid specimens derived from mammalian subjects and include for example blood, plasma, sperm, milk, urine, saliva or cerebral spinal fluid.

According to a particular embodiment, the specimen is plasma or blood.

Specimens which are analyzed typically comprise DNA from at least one or at least two cell/tissue sources, as further described herein below. Thus for example the specimens may comprise cell-free DNA from a single cell type or at least two cell types.

According to one embodiment, a specimen of blood is obtained from a subject according to methods well known in the art. Plasma or serum may be isolated according to methods known in the art.

DNA may be isolated from the blood immediately or within 1 hour, 2 hours, 3 hours, 4 hours, 5 hours or 6 hours. Optionally the blood is stored at temperatures such as 4° C., or at −20° C. prior to isolation of the DNA. In some embodiments, a portion of the blood specimen is used in accordance with the invention at a first instance of time whereas one or more remaining portions of the blood specimen (or fractions thereof) are stored for a period of time for later use.

According to one embodiment, the DNA molecule which is analyzed is cellular DNA (i.e. comprised in a cell).

According to still another embodiment, the DNA molecule which is analyzed is comprised in a shredded cell or non-intact cell.

Methods of DNA extraction are well-known in the art. A classical DNA isolation protocol is based on extraction using organic solvents such as a mixture of phenol and chloroform, followed by precipitation with ethanol (J. Sambrook et al., "Molecular Cloning: A Laboratory Manual", 1989, $2^{nd}$ Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 4692-4693), trimethylammonium bromide salts DNA extraction (S. Gustincich et al., BioTechniques, 1991, 11: 298-302) and guanidinium thiocyanate DNA extraction (J. B. W. Hammond et al., Biochemistry, 1996, 240: 298-300).

There are also numerous versatile kits that can be used to extract DNA from tissues and bodily fluids and that are commercially available from, for example, BD Biosciences Clontech (Palo Alto, Calif.), Epicentre Technologies (Madison, Wis.), Gentra Systems, Inc. (Minneapolis, Minn.), MicroProbe Corp. (Bothell, Wash.), Organon Teknika (Durham, N.C.), and Qiagen Inc. (Valencia, Calif.). User Guides that describe in great detail the protocol to be followed are usually included in all these kits. Sensitivity, processing time and cost may be different from one kit to another. One of ordinary skill in the art can easily select the kit(s) most appropriate for a particular situation.

According to another embodiment, the DNA which is analyzed is cell-free DNA. For this method, cell lysis is not performed on the specimen. Methods of isolating cell-free DNA from body fluids are also known in the art. For example Qiaquick kit, manufactured by Qiagen may be used to extract cell-free DNA from plasma or serum.

The specimen may be processed before the method is carried out, for example DNA purification may be carried out following the extraction procedure. The DNA in the specimen may be cleaved either physically or chemically (e.g. using a suitable enzyme). Processing of the specimen may involve one or more of: filtration, distillation, centrifugation, extraction, concentration, dilution, purification, inactivation of interfering components, addition of reagents, and the like.

To analyze methylation status according to this aspect of the present invention, the DNA is treated with bisulfite which converts cytosine residues to uracil (which are converted to thymidine following PCR), but leaves 5-methylcytosine residues unaffected. Thus, bisulfite treatment introduces specific changes in the DNA sequence that depend on the methylation status of individual cytosine residues, yielding single-nucleotide resolution information about the methylation status of a segment of DNA.

During the bisulfite reaction, care should be taken to minimize DNA degradation, such as cycling the incubation temperature.

Bisulfite sequencing relies on the conversion of every single unmethylated cytosine residue to uracil. If conversion is incomplete, the subsequent analysis will incorrectly interpret the unconverted unmethylated cytosines as methylated cytosines, resulting in false positive results for methylation. Only cytosines in single-stranded DNA are susceptible to attack by bisulfite, therefore denaturation of the DNA undergoing analysis is critical. It is important to ensure that reaction parameters such as temperature and salt concentration are suitable to maintain the DNA in a single-stranded conformation and allow for complete conversion.

According to a particular embodiment, an oxidative bisulfite reaction is performed. 5-methylcytosine and 5-hydroxymethylcytosine both read as a C in bisulfite sequencing. Oxidative bisulfite reaction allows for the discrimination between 5-methylcytosine and 5-hydroxymethylcytosine at single base resolution. The method employs a specific chemical oxidation of 5-hydroxymethylcytosine to 5-formylcytosine, which subsequently converts to uracil during bisulfite treatment. The only base that then reads as a C is 5-methylcytosine, giving a map of the true methylation status in the DNA specimen. Levels of 5-hydroxymethylcytosine can also be quantified by measuring the difference between bisulfite and oxidative bisulfite sequencing.

Following bisulfite treatment, the bisulfite-treated DNA sequence is fractionated and then optionally subjected to an amplification reaction.

To fractionate the DNA specimen, emulsification techniques can be used so as to create large numbers of aqueous droplets that function as independent reaction chambers for the PCR reactions. For example, an aqueous specimen (e.g., 20 microliters) can be partitioned into droplets (e.g., 20.000 droplets of one nanoliter each) to allow an individual test for the target to be performed with each of the droplets.

Aqueous droplets can be suspended in oil to create a water-in-oil emulsion (NV/O). The emulsion can be stabilized with a surfactant to reduce coalescence of droplets during heating, cooling, and transport, thereby enabling thermal cycling to be performed.

In an exemplary droplet-based digital assay, a specimen is partitioned into a set of droplets at a dilution that ensures that more than 40% of the droplets contain no more than one single-stranded DNA molecule per specimen fraction.

In an exemplar)/droplet-based digital assay, a specimen is partitioned into a set of droplets at a dilution that ensures that more than 50% of the droplets contain no more than one single-stranded DNA molecule per specimen fraction.

In an exemplary droplet-based digital assay, a specimen is partitioned into a set of droplets at a dilution that ensures that more than 60% of the droplets contain no more than one single-stranded DNA molecule per specimen fraction.

In an exemplary droplet-based digital assay, a specimen is partitioned into a set of droplets at a dilution that ensures that more than 70% of the droplets contain no more than one single-stranded. DNA molecule per specimen fraction.

In an exemplary droplet-based digital assay, a specimen is partitioned into a set of droplets at a dilution that ensures that more than 80% of the droplets contain no more than one single-stranded DNA molecule per specimen fraction.

In an exemplary droplet-based digital assay, a specimen is partitioned into a set of droplets at a dilution that ensures that more than 90% of the droplets contain no more than one single-stranded DNA molecule per specimen fraction.

Once fractionation has taken place, the single-stranded DNA may then optionally be amplified.

As used herein, the term "amplification" refers to a process that increases the representation of a population of specific nucleic acid sequences in a specimen by producing multiple (i.e., at least 2) copies of the desired sequences. Methods for nucleic acid amplification are known in the art and include, but are not limited to, polymerase chain reaction (PCR) and ligase chain reaction (LCR). In a typical PCR amplification reaction, a nucleic acid sequence of interest is often amplified at least fifty thousand fold in amount over its amount in the starting specimen. A "copy" or "amplicon" does not necessarily mean perfect sequence complementarity or identity to the template sequence. For example, copies can include nucleotide analogs such as deoxyinosine, intentional sequence alterations (such as sequence alterations introduced through a primer comprising a sequence that is hybridizable but not complementary to the template), and/or sequence errors that occur during amplification.

A typical amplification reaction is carried out by contacting a forward and reverse primer (a primer pair) to the specimen DNA together with any additional amplification reaction reagents under conditions which allow amplification of the target sequence. The oligonucleotide amplification primers typically flank the target sequence—(i.e. the sequence comprising the at least two, three, four or five methylation sites (per single strand).

The terms "forward primer" and "forward amplification primer" are used herein interchangeably, and refer to a primer that hybridizes (or anneals) to the target (template strand). The terms "reverse primer" and "reverse amplification primer" are used herein interchangeably, and refer to a primer that hybridizes (or anneals) to the complementary target strand. The forward primer hybridizes with the target sequence 5' with respect to the reverse primer.

The term "amplification conditions", as used herein, refers to conditions that promote annealing and/or extension of primer sequences. Such conditions are well-known in the art and depend on the amplification method selected. Thus, for example, in a PCR reaction, amplification conditions generally comprise thermal cycling, i.e., cycling of the reaction mixture between two or more temperatures. In isothermal amplification reactions, amplification occurs without thermal cycling although an initial temperature increase may be required to initiate the reaction. Amplification conditions encompass all reaction conditions including, but not limited to, temperature and temperature cycling, buffer, salt, ionic strength, and pH, and the like.

As used herein, the term "amplification reaction reagents", refers to reagents used in nucleic acid amplification reactions and may include, but are not limited to, buffers, reagents, enzymes having reverse transcriptase and/or polymerase activity or exonuclease activity, enzyme cofactors such as magnesium or manganese, salts, nicotinamide adenine dinuclease (NAD) and deoxynucleoside triphosphates (dNTPs), such as deoxyadenosine triphospate, deoxyguanosine triphosphate, deoxycytidine triphosphate and thymidine triphosphate. Amplification reaction reagents may readily be selected by one skilled in the art depending on the amplification method used.

In one embodiment, the amplification reaction uses a single labeled oligonucleotide probe which hybridizes to one strand of the amplified DNA which comprises at least two, at least three, at least four, at least five methylation sites (for example as illustrated in FIG. 16B).

In another embodiment, the amplification reaction uses at least two probes, one which hybridizes to the first strand of the amplified DNA and one which hybridizes to the second strand of the amplified DNA (for example as illustrated in FIG. 16A). Preferably the two probes are labeled with non-identical labels i.e. detectable moieties.

The oligonucleotides of the invention (e.g. primers or probes) need not reflect the exact sequence of the target nucleic acid sequence (i.e. need not be fully complementary), but must be sufficiently complementary so as to hybridize to the target site under the particular experimental conditions. Accordingly, the sequence of the oligonucleotide typically has at least 70% homology, preferably at least 80%, 90%, 95%, 97%, 99% or 100% homology, for example over a region of at least 13 or more contiguous nucleotides with the target sequence. The conditions are selected such that hybridization of the oligonucleotide to the target site is favored and hybridization to the non-target site is minimized.

Various considerations must be taken into account when selecting the stringency of the hybridization conditions. For example, the more closely the oligonucleotide (e.g. primer) reflects the target nucleic acid sequence, the higher the stringency of the assay conditions can be, although the stringency must not be too high so as to prevent hybridization of the oligonucleotides to the target sequence. Further, the lower the homology of the oligonucleotide to the target sequence, the lower the stringency of the assay conditions should be, although the stringency must not be too low to allow hybridization to non-specific nucleic acid sequences.

Oligonucleotides of the invention may be prepared by any of a variety of methods (see, for example, J. Sambrook et al., "Molecular Cloning: A Laboratory Manual", 1989, 2.sup.nd Ed., Cold Spring Harbour Laboratory Press: New York, N.Y.; "PCR Protocols: A Guide to Methods and Applications", 1990, M. A. Innis (Ed.), Academic Press: New York, N.Y.; P. Tijssen "Hybridization with Nucleic Acid Probes— Laboratory Techniques in Biochemistry and Molecular Biology (Parts I and II)", 1993, Elsevier Science; "PCR Strategies", 1995, M. A. Innis (Ed.), Academic Press: New York, N.Y.; and "Short Protocols in Molecular Biology", 2002, F. M. Ausubel (Ed.), 5.sup.th Ed., John Wiley & Sons: Secaucus, N.J.). For example, oligonucleotides may be prepared using any of a variety of chemical techniques well-known in the art, including, for example, chemical synthesis and polymerization based on a template as described, for example, in S. A. Narang et al., Meth. Enzymol. 1979, 68: 90-98; E. L. Brown et al., Meth. Enzymol. 1979, 68: 109-151; E. S. Belousov et al., Nucleic Acids Res. 1997, 25: 3440-3444; D. Guschin et al., Anal. Biochem. 1997, 250: 3440-3444; D. Guschin et al., Anal. Biochem. 1997, 250: 203-211; M. J. Blommers et al., Biochemistry, 1994, 33: 7886-7896; and K. Frenkel et al., Free Radic. Biol. Med. 1995, 19: 373-380; and U.S. Pat. No. 4,458,066.

For example, oligonucleotides may be prepared using an automated, solid-phase procedure based on the phosphoramidite approach. In such a method, each nucleotide is individually added to the 5'-end of the growing oligonucleotide chain, which is attached at the 3'-end to a solid support. The added nucleotides are in the form of trivalent 3'-phosphoramidites that are protected from polymerization by a dimethoxytriyl (or DMT) group at the 5'-position. After base-induced phosphoramidite coupling, mild oxidation to give a pentavalent phosphotriester intermediate and DMT removal provides a new site for oligonucleotide elongation. The oligonucleotides are then cleaved off the solid support, and the phosphodiester and exocyclic amino groups are deprotected with ammonium hydroxide. These syntheses may be performed on oligo synthesizers such as those commercially available from Perkin Elmer/Applied Biosystems, Inc. (Foster City, Calif.), DuPont (Wilmington, Del.) or Milligen (Bedford, Mass.). Alternatively, oligonucleotides can be custom made and ordered from a variety of commercial sources well-known in the art, including, for example, the Midland Certified Reagent Company (Midland, Tex.), ExpressGen, Inc. (Chicago, Ill.), Operon Technologies, Inc. (Huntsville, Ala.), and many others.

Purification of the oligonucleotides of the invention, where necessary or desirable, may be carried out by any of a variety of methods well-known in the art. Purification of oligonucleotides is typically performed either by native acrylamide gel electrophoresis, by anion-exchange HPLC as described, for example, by J. D. Pearson and F. E. Regnier (J. Chrom., 1983, 255: 137-149) or by reverse phase HPLC (G. D. McFarland and P. N. Borer, Nucleic Acids Res., 1979, 7: 1067-1080).

The sequence of oligonucleotides can be verified using any suitable sequencing method including, but not limited to, chemical degradation (A. M. Maxam and W. Gilbert, Methods of Enzymology, 1980, 65: 499-560), matrix-assisted laser desorption ionization time-of-flight (MALDI-TOF) mass spectrometry (U. Pieles et al., Nucleic Acids Res., 1993, 21: 3191-3196), mass spectrometry following a combination of alkaline phosphatase and exonuclease digestions (H. Wu and H. Aboleneen, Anal. Biochem., 2001, 290: 347-352), and the like.

In certain embodiments, the detection probes or amplification primers (or both) are labeled with a detectable agent or moiety before being used in amplification/detection assays. In certain embodiments, the detection probes are labeled with a detectable agent. Preferably, a detectable agent is selected such that it generates a signal which can be measured and whose intensity is related (e.g., proportional) to the amount of amplification products in the sample being analyzed.

The association between the oligonucleotide and detectable agent can be covalent or non-covalent. Labeled detection probes can be prepared by incorporation of or conjugation to a detectable moiety. Labels can be attached directly to the nucleic acid sequence or indirectly (e.g., through a linker). Linkers or spacer arms of various lengths are known in the art and are commercially available, and can be selected to reduce steric hindrance, or to confer other useful or desired properties to the resulting labeled molecules (see, for example, E. S. Mansfield et al., Mol. Cell. Probes, 1995, 9: 145-156).

Methods for labeling nucleic acid molecules are well-known in the art. For a review of labeling protocols, label detection techniques, and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153. Standard nucleic acid labeling methods include: incorporation of radioactive agents, direct attachments of fluorescent dyes (L. M. Smith et al., Nucl. Acids Res., 1985, 13: 2399-2412) or of enzymes (B. A. Connoly and O. Rider, Nucl. Acids. Res., 1985, 13: 4485-4502); chemical modifications of nucleic acid molecules making them detectable immunochemically or by other affinity reactions T. R. Broker et al., Nucl. Acids Res. 1978, 5: 363-384; E. A. Bayer et al., Methods of Biochem. Analysis, 1980, 26: 1-45; R. Langer et al., Proc. Natl. Acad. Sci. USA, 1981, 78: 6633-6637; R. W. Richardson et al., Nucl. Acids Res. 1983, 11: 6167-6184; D. J. Brigati et al., Virol. 1983, 126: 32-50; P. Tchen et al., Proc. Natl. Acad. Sci. USA, 1984, 81: 3466-3470; J. E. Landegent et al., Exp. Cell Res. 1984, 15: 61-72; and A. H. Hopman et al., Exp. Cell Res. 1987, 169: 357-368); and enzyme-mediated labeling methods, such as random priming, nick translation, PCR and tailing with terminal transferase (for a review on enzymatic labeling, see, for example, J. Temsamani and S. Agrawal, Mol. Biotechnol. 1996, 5: 223-232). More recently developed nucleic acid labeling systems include, but are not limited to: ULS (Universal Linkage System), which is based on the reaction of mono-reactive cisplatin derivatives with the N7 position of guanine moieties in DNA (R. J. Heetebrij et al., Cytogenet. Cell. Genet. 1999, 87: 47-52), psoralen-biotin, which intercalates into nucleic acids and upon UV irradiation becomes covalently bonded to the nucleotide bases (C. Levenson et al., Methods Enzymol. 1990, 184: 577-583; and C. Pfannschmidt et al., Nucleic Acids Res. 1996, 24: 1702-1709), photoreactive azido derivatives (C. Neves et al., Bioconjugate Chem. 2000, 11: 51-55), and DNA alkylating agents (M. G. Sebestyen et al., Nat. Biotechnol. 1998, 16: 568-576).

If the methylation sites are close enough together on the DNA, it is conceivable that the probes of this aspect of the present invention hybridize to more than one methylation site, for example, two, three, or even four—see for example FIG. 16B.

The sequence of the first and/or second probe may be selected such that it binds to the amplified DNA when the methylation site of the double-stranded DNA molecule is non-methylated.

Alternatively, the sequence of the first and/or second probe may be selected such that it binds to the amplified DNA when the methylation site of the double-stranded DNA molecule is methylated.

In certain embodiments, the inventive detection probes are fluorescently labeled. Numerous known fluorescent labeling moieties of a wide variety of chemical structures and physical characteristics are suitable for use in the practice of this invention. Suitable fluorescent dyes include, but are not limited to, fluorescein and fluorescein dyes (e.g., fluorescein isothiocyanine or FITC, naphthofluorescein, 4',5'-dichloro-2',7'-dimethoxy-fluorescein, 6 carboxyfluorescein or FAM), carbocyanine, merocyanine, styryl dyes, oxonol dyes, phycoerythrin, erythrosin, eosin, rhodamine dyes (e.g., carboxytetramethylrhodamine or TAMRA, carboxyrhodamine 6G, carboxy-X-rhodamine (ROX), lissamine rhodamine B, rhodamine 6G, rhodamine Green, rhodamine Red, tetramethylrhodamine or TMR), coumarin and coumarin dyes (e.g., methoxycoumarin, dialkylaminocoumarin, hydroxycoumarin and aminomethylcoumarin or AMCA), Oregon Green Dyes (e.g., Oregon Green 488, Oregon Green 500, Oregon Green 514), Texas Red, Texas Red-X, Spectrum Red™, Spectrum Green™, cyanine dyes (e.g., Cy-3™, Cy-5™, Cy-3.5™, Cy-5.5™, Alexa Fluor dyes (e.g., Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), BODIPY dyes (e.g., BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), IRDyes (e.g., IRD40, IRD 700, IRD 800), and the like. For more examples of suitable fluorescent dyes and methods for linking or incorporating fluorescent dyes to nucleic acid molecules see, for example, "The Handbook of Fluorescent Probes and Research Products", 9th Ed., Molecular Probes, Inc., Eugene, Oreg. Fluorescent dyes as well as labeling kits are commercially available from, for example, Amersham Biosciences, Inc. (Piscataway, N.J.), Molecular Probes Inc. (Eugene, Oreg.), and New England Biolabs Inc. (Beverly, Mass.). Another contemplated method of analyzing the methylation status of the sequences is by analysis of the DNA following exposure to methylation-sensitive restriction enzymes—see for example US Application Nos. 20130084571 and 20120003634, the contents of which are incorporated herein.

Exemplary probes for detecting cardiac DNA are set forth in SEQ ID NOs: 118 and 119.

Exemplary probes for detecting colon DNA are set forth in SEQ ID NOs: 125 and 126.

Exemplary probes for detecting liver DNA are set forth in SEQ ID NOs: 128, 129 and 130.

In one embodiment, the probes that are used are TaqMan™ probes.

TaqMan™ probes comprise a detectable moiety (e.g. fluorophore) covalently attached to the 5'-end of the oligonucleotide probe and a quencher at the 3'-end. Several different fluorophores (e.g. 6-carboxyfluorescein, acronym: FAM, or tetrachlorofluorescein, acronym: TET) and quenchers (e.g. tetramethylrhodamine, acronym: TAMRA) are available. The quencher molecule quenches the fluorescence emitted by the fluorophore when excited by the cycler's light source via FRET (Forster Resonance Energy Transfer). As long as the fluorophore and the quencher are in proximity, quenching inhibits any fluorescence signals.

Other examples of quenchers include, but are not limited to Dabcyl™, TAMRA™, ECLIPSE™, DDQ™, QSY™, Blackberry Quencher™, Black Hole Quencher™, Qxl, Iowa black FQ™, Iowa black RQ™, and IRDye QC-1™.

TaqMan™ probes are designed such that they anneal within a DNA region amplified by a specific set of primers. As the Taq polymerase extends the primer and synthesizes the nascent strand, the 5' to 3' exonuclease activity of the Taq polymerase degrades the probe that has annealed to the template. Degradation of the probe releases the detectable moiety from it and breaks the close proximity to the quencher, thus relieving the quenching effect and allowing for detection of the detectable moiety (e.g. it allow for fluorescence of the fluorophore). Hence, the amount of detectable moiety is directly proportional to the amount of DNA template present in the PCR.

According to a particular embodiment, determining the methylation status is carried out as follows:

The bisulfate-treated DNA of the specimen is contacted with:

(i) a first probe that hybridizes to at least one methylation site of the amplified DNA; and (ii) a second probe that hybridizes to at least one other methylation site of the amplified DNA, wherein the first probe and the second probe are labeled with non-identical detectable moieties, wherein the first probe and the second probe comprise a quenching moiety.

According to a particular embodiment, the first probe hybridizes to the forward strand of the amplified DNA and the second probe hybridizes to the reverse strand of the amplified DNA (see for example FIG. 5A).

The contacting is effected under conditions that separate the quenching moiety from the first probe and the second probe to generate a non-quenched first probe and a non-quenched second probe. The conditions are those which are inductive for an amplification reaction—i.e. presence of a polymerase enzyme having 5' to 3' nuclease activity (e.g. Taqman™ polymerase), dNTPs and buffer etc.

Once sufficient amplification has occurred, the amount of non-quenched first probe and non-quenched second probe in a single droplet can be measured—e.g. by using a fluorimeter.

In one embodiment, the number of droplets containing a signal from both probes is scored Exemplary targets that may be analyzed according to this aspect of the present invention are provided in US Patent Application No. 20170121767, the contents of which are incorporated herein by reference.

According to a particular embodiment, the target comprises at least a part of the sequence of human chromosome 12, between coordinates 124692462-124692551 (e.g. SEQ ID NOs: 56 or 57).

According to another embodiment, the target comprises at least a part of the ECH1 locus.

According to still another embodiment, the target comprises at least a part of the IGF2R gene or the VTN gene (e.g. SEQ ID NOs: 65 or 66).

Other exemplary targets that may be analyzed are comprised in the sequences set forth in SEQ ID Nos: 2-117 or SEQ ID NOs: 135-191. According to a particular embodiment, the target sequence comprises the nucleotides CG which are at position 250 and 251 of each of these sequences.

According to another embodiment, at least one of the methylation sites of the signature are the nucleotides CG which are at position 250 and 251 of each of these sequences.

Kits

Any of the components described herein may be comprised in a kit. In a non-limiting example the kit comprises:

(i) a first oligonucleotide probe, wherein the 3' end of said first probe comprises a quenching moiety and the 5' end is labeled with a first detectable moiety;

(ii) a second oligonucleotide probe, wherein the 3' end of said second probe comprises a quenching moiety and the 5' end is labeled with a second detectable moiety;

wherein the sequence of said first probe is selected so as to determine a methylation status at a first methylation site of the double-stranded DNA molecule and the sequence of said second probe is selected so as determine a methylation status at a second methylation site of the same double-stranded DNA molecule, wherein said first methylation site and said second methylation site are no more than 300 base pairs apart; and (iii) a polymerase enzyme having 5' to 3' nuclease activity (e.g. Taqman™ polymerase).

In another non-limiting example, the kit includes:

(i) at least two oligonucleotides, wherein the sequence of said first oligonucleotide of said at least two oligonucleotides is selected so as to determine a methylation status at a first methylation site of the double-stranded DNA molecule and the sequence of said second oligonucleotide of said at least two oligonucleotides is selected so as determine a methylation status at a second methylation site of the same double-stranded DNA molecule, wherein said first methylation site and said second methylation site are no more than 300 base pairs apart; and (ii) a droplet forming oil.

Detectable moieties, quenching moieties and probes have been described herein above.

Additional components that may be included in any of the above described kits include at least one of the following components: a droplet forming oil, bisulfite (and other reagents necessary for the bisulfite reaction), reagents for purification of DNA, $MgCl_2$. The kit may also comprise reaction components for sequencing the amplified or non-amplified sequences.

The kits may also comprise DNA sequences which serve as controls. Thus, for example, the kit may comprise a DNA having the same sequence as the amplified sequence derived from a healthy subject (to serve as a negative control) and/or a DNA having the same sequence as the amplified sequence derived from a subject known to have the disease which is being investigated (to serve as a positive control).

In addition, the kits may comprise known quantities of DNA such that calibration and quantification of the test DNA may be carried out.

The containers of the kits will generally include at least one vial, test tube, flask, bottle, syringe or other containers, into which a component may be placed, and preferably, suitably aliquoted. Where there is more than one component in the kit, the kit also will generally contain a second, third or other additional container into which the additional components may be separately placed. However, various combinations of components may be comprised in a container.

When the components of the kit are provided in one or more liquid solutions, the liquid solution can be an aqueous solution. However, the components of the kit may be provided as dried powder(s). When reagents and/or components are provided as a dry powder, the powder can be reconstituted by the addition of a suitable solvent.

A kit will preferably include instructions for employing, the kit components as well the use of any other reagent not included in the kit. Instructions may include variations that can be implemented.

Diagnostics

It will be appreciated that analysis of the methylation status according to methods described herein allows for the accurate determination of cellular/tissue source of a DNA molecule, even when the majority of the DNA of the sample is derived from a different cellular source. The present inventors have shown that they are able to determine the cellular source of a particular DNA even when its contribution to the total amount of DNA in the population is less than 1:1000, less than 1:5,000, 1:10,000 or even 1:100,000.

Pathological and disease conditions that involve cell death cause the release of degraded DNA from dying cells into body fluids (blood, plasma, urine, cerebrospinal fluid). Thus, the methods described herein may be used to analyze the amount of cell death of a particular cell population in those body fluids. The amount of cell death of a particular cell population can then be used to diagnose a particular pathological state (e.g. disease) or condition (e.g. trauma).

It will be appreciated that death of a particular cell type may be associated with a pathological state—e.g. disease or trauma.

The monitoring of the death of a particular cell type may also be used for monitoring the efficiency of a therapeutic regime expected to effect cell death of a specific cell type.

The determination of death of a specific cell type may also be used in the clinical or scientific study of various mechanism of healthy or diseased subjects.

Thus, for example measurement of pancreatic beta cell death is important in cases of diabetes, hyperinsulinism and islet cell tumors, and in order to monitor beta cell survival after islet transplantation, determining the efficacy of various treatment regimes used to protect beta cells from death, and determining the efficacy of treatments aimed at causing islet cell death in islet cell tumors. Similarly, the method allows the identification and quantification of DNA derived from dead kidney cells (indicative of kidney failure), dead neurons (indicative of traumatic brain injury, amyotrophic lateral sclerosis (ALS), stroke, Alzheimer's disease, Parkinson's disease or brain tumors, with or without treatment); dead pancreatic acinar cells (indicative of pancreatic cancer or pancreatitis); dead lung cells (indicative of lung pathologies including lung cancer); dead adipocytes (indicative of altered fat turnover), dead hepatocytes (indicative of liver failure, liver toxicity or liver cancer) dead cardiomyocytes (indicative of cardiac disease, or graft failure in the case of cardiac transplantation), dead skeletal muscle cells (indicative of muscle injury and myopathies), dead oligodendrocytes (indicative of relapsing multiple sclerosis, white matter damage in amyotrophic lateral sclerosis, or glioblastoma), dead colon cells is indicative of colorectal cancer.

As used herein, the term "diagnosing" refers to determining the presence of a disease, classifying a disease, determining a severity of the disease (grade or stage), monitoring disease progression and response to therapy, forecasting an outcome of the disease and/or prospects of recovery.

The method comprises quantifying the amount of cell-free DNA which is comprised in a fluid sample (e.g. a blood sample or serum sample) of the subject which is derived from a cell type or tissue. When the amount of cell free DNA derived from the cell type or tissue is above a predetermined level, it is indicative that there is a predetermined level of cell death. When the level of cell death is above a predetermined level, it is indicative that the subject has the disease or pathological state. Determining the predetermined level may be carried out by analyzing the amount of cell-free DNA present in a sample derived from a subject known not to have the disease/pathological state. If the level of the cell-free DNA derived from a cell type or tissue associated with the disease in the test sample is statistically significantly higher (e.g. at least two fold, at least three fold, or at least 4 fold) than the level of cell-free DNA derived from the same cell type or tissue in the sample obtained from the healthy (non-diseased subject), it is indicative that the subject has the disease. Alternatively, or additionally, determining the predetermined level may be carried out by analyzing the amount of cell-free DNA present in a sample derived from a subject known to have the disease. If the level of the cell-free DNA derived from a cell type or tissue associated with the disease in the test sample is statistically significantly similar to the level of the cell-free DNA derived from a cell type of tissue associated with the disease in the sample obtained from the diseased subject, it is indicative that the subject has the disease.

The severity of disease may be determined by quantifying the amount of DNA molecules having the specific methylation pattern of a cell population associated with the disease. Quantifying the amount of DNA molecules having the specific methylation pattern of a target tissue may be achieved using a calibration curve produced by using known and varying numbers of cells from the target tissue.

According to one embodiment, the method comprises determining the ratio of the amount of cell free DNA derived from a cell of interest in the sample: amount of overall cell free DNA.

According to still another embodiment, the method comprises determining the ratio of the amount of cell free DNA derived from a cell of interest in the sample: amount of cell free DNA derived from a second cell of interest.

The methods described herein may also be used to determine the efficacy of a therapeutic agent or treatment, wherein when the amount of DNA associated with a cell population associated with the disease is decreased following administration of the therapeutic agent, it is indicative that the agent or treatment is therapeutic.

According to some embodiments of the invention, screening of the subject for a specific disease is followed by substantiation of the screen results using gold standard methods.

The method can also be used to predict prognosis of the subject with the disease.

According to some embodiments of the invention, the method further comprising informing the subject of the predicted disease and/or the predicted prognosis of the subject.

As used herein the phrase "informing the subject" refers to advising the subject that based on the cfDNA levels, the subject should seek a suitable treatment regimen.

Once the cfDNA level is determined, the results can be recorded in the subject's medical file, which may assist in selecting a treatment regimen and/or determining prognosis of the subject.

According to some embodiments of the invention, the method further comprising recording the cfDNA levels of the subject in the subject's medical file.

As mentioned, the prediction can be used to select the treatment regimen of a subject and thereby treat the subject in need thereof.

As used herein the term "about" refers to ±10%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is understood that any Sequence Identification Number (SEQ ID NO) disclosed in the instant application can refer to either a DNA sequence or a RNA sequence, depending on the context where that SEQ ID NO is mentioned, even if that SEQ ID NO is expressed only in a DNA sequence format or a RNA sequence format. For example, SEQ ID NO: XXX is expressed in a DNA sequence format (e.g., reciting T for thymine), but it can refer to either a DNA sequence that corresponds to an XXX nucleic acid sequence, or the RNA sequence of an RNA molecule nucleic acid sequence. Similarly, though some sequences are expressed in a RNA sequence format (e.g., reciting U for uracil), depending on the actual type of molecule being described, it can refer to either the sequence of a RNA molecule comprising a dsRNA, or the sequence of a DNA molecule that corresponds to the RNA sequence shown. In any event, both DNA and RNA molecules having the sequences disclosed with any substitutes are envisioned.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Clinical Specimens:
Cardiac biomarkers used were troponin T and CPK.
Identification of Cardiac Methylation Markers:
Tissue-specific DNA methylation markers were selected after a comparison of publically available DNA methylation datasets generated by whole-genome bisulfite sequencing (Roadmap Epigenomics). The fragment of FAM101A used as a cariomyocyte-specific marker is located in chromosome 12, coordinates124692462-124692551.

cfDNA Analysis:

Blood specimens were collected in EDTA tubes, and centrifuged within 2 hours to separate plasma from peripheral blood cells: first at 1500 g for 10 min, and then at 3000 g for 10 min to remove any remaining cells. Plasma was then stored at 80° C.

cfDNA was extracted using the QIAsymphony SP instrument and its dedicated QIAsymphony Circulating DNA Kit (Qiagen) according to the manufacturer's instructions.

DNA concentration was measured using the Qubit™ dsDNA HS Assay Kit.

cfDNA was treated with bisulfite using a kit (Zymo Research), and PCR amplified with primers specific for bisulfite-treated DNA but independent of methylation status at the monitored CpG sites. Primers were bar-coded, allowing the mixing of specimens from different individuals when sequencing PCR products using MiSeq or NextSeq (Illumina). Sequenced reads were separated by barcode, aligned to the target sequence, and analyzed using custom scripts written and implemented in R. Reads were quality filtered based on Illumina quality scores, and identified by having at least 80% similarity to target sequences and containing all the expected CpGs in the sequence. CpGs were considered methylated if "CG" was read and were considered unmethylated if "TG" was read.

Digital Droplet PCR:

A procedure was established for digital droplet PCR, in which bisulfite-treated cfDNA is amplified using a methylation-sensitive Taqman™ probe.

The limited length of probes (up to 30 bp) dictated that they could cover only 2 or 3 informative CpG sites in the FAM101A locus, predicting a relatively high frequency of "noise" (positive droplets) in DNA from non-cardiac tissue. In the sequencing-based assay, this problem was addressed by documenting the methylation status of multiple adjacent cytosines (FIGS. 1A-E), which greatly increased specificity.

To implement this concept in the ddPCR platform, two Taqman™ probes were designed, each recognizing lack of methylation in a different cluster of cytosines (one containing 2 CpG sites and one containing 3 CpG sites) within the same amplified 100 bp fragment from the FAM101A locus (FIG. 5A). Each probe was labeled with a different fluorophore, such that droplets could be identified in which both probes found a target. Such droplets would be interpreted as containing a FAM101A cfDNA fragment in which all 5 targeted cytosines were demethylated. This would provide ddPCR with the improved specificity afforded by interrogating multiple cytosines on the same DNA molecule.

For the analysis of 5 cytosines, located adjacent to the FAM101A locus, the following primers were used: 5'-TATGGTTTGGTAATTTATTTAGAG-3' (SEQ ID NO: 1; forward) and 5'-AAATACAAATCCCACAAATAAA-3' (SEQ ID NO: 120; reverse) in combination with probes that detected lack of methylation on 3 and 2 cytosines respectively: 5'-AATGTATGGTGAAATGTAGTGTTGGG-3' (SEQ ID NO: 118; FAM-forward probe) and 5'-AAAAATACTCAACTTCCATCTACAATT-3' (SEQ ID NO: 119, HEX-reverse probe).

Assay design is shown in FIG. 5A. Each 20-μL volume reaction mix consisted of ddPCR™ Supermix for Probes (No dUTP) (Bio-Rad), 900 nM primer, 250 nM probe, and 2 μL of specimen. The mixture and droplet generation oil were loaded onto a droplet generator (Bio-Rad). Droplets were transferred to a 96-well PCR plate and sealed. The PCR was run on a thermal cycler as follows: 10 minutes of activation at 95° C., 47 cycles of a 2 step amplification protocol (30 s at 94° C. denaturation and 60 s at 53.7° C.), and a 10-minute inactivation step at 98° C. The PCR plate was transferred to a QX100Droplet Reader (Bio-Rad), and products were analyzed with QuantaSoft (Bio-Rad) analysis software. Discrimination between droplets that contained the target (positives) and those which did not (negatives) was achieved by applying a fluorescence amplitude threshold based on the amplitude of reads from the negative template control.

Results

Identification of Cardiomyocyte Methylation Markers

To define genomic loci that are methylated in a cardiac-specific manner, the methylomes of human heart chambers (right atrium, left and right ventricle) were compared with the methylomes of 23 other human tissues, all publicly available[12]. Several differentially methylated loci were identified and a cluster of cytosines adjacent to the FAM101A locus was selected for further analysis (FIGS. 1A-B). PCR was used to amplify a 90 bp fragment around this cluster after bisulfite conversion of unmethylated cytosines, and the PCR product was sequenced to determine the methylation status of all 6 cytosines in the cluster. In purified cardiomyocyte DNA, 89% of the molecules were fully unmethylated, while in non-cardiac tissue<0.2% of molecules were unmethylated; specifically in leukocytes (the main contributor to cfDNA), <0.006% of molecules were unmethylated (FIG. 1C and FIGS. 6A-C). Thus, interrogating all CpGs simultaneously, the ratio of demethylated molecules in heart:blood DNA was 89:0.006 giving a signal to noise ratio of 15,000.

To determine the linearity and sensitivity of the assay, leukocyte DNA was spiked with increasing amounts of cardiac DNA. The fraction of cardiac DNA in the mixture was assessed using PCR amplification and massively parallel sequencing. The assay was able to correctly determine the fraction of cardiac DNA, even when it was only 0.5% of the DNA in the mixture (FIG. 1D).

Following bisulfite treatment, DNA becomes single stranded. Therefore, each strand can be considered an independent biomarker. To test this idea, the present inventors designed primers against the antisense strand of FAM101A post-bisulfite conversion. As expected, the sense and antisense templates showed a similar sensitivity and specificity (FIGS. 1B-E and 6A-C). It was reasoned that by testing both strands in a given specimen, both sensitivity and specificity of the assay will increase. For this reason further analysis of clinical specimens was performed using both sense and antisense specific primer sets.

Plasma Levels of Cardiomyocyte DNA in Healthy Individuals

The sense and antisense FAM101A markers were used to assess the concentration of cardiac cfDNA in the plasma of donors. cfDNA was extracted from plasma and treated with bisulfite. PCR and sequencing were performed, typically using material from 0.5 ml of plasma. The fraction of PCR products carrying the cardiac-specific methylation pattern was multiplied by the total concentration of cfDNA, to obtain an estimation of cardiac cfDNA content in plasma.

Healthy adult plasma from 83 healthy donors was tested and zero copies of cardiac cfDNA were detected in 73 of them (FIG. 2A). In ten individuals, 1-20 copies/ml cardiac cfDNA was found. This low level of a signal likely reflects the low rate of cardiomyocyte death in healthy adults[13]. The mean plus 2 standard deviations of the control group was 10 copies/ml, and this was thus defined as the cutoff level for a positive signal.

Plasma Levels of Cardiomyocyte DNA after Myocardial Infarction

As a positive control where high levels of cardiac cfDNA are expected, plasma from donors with myocardial infarction (MI) were used. Specimens from individuals that presented with chest pain, before and after they underwent angioplasty were used. The levels of cardiac cfDNA as well as troponin and CPK were assessed. MI patients showed dramatically higher levels of cardiac cfDNA than healthy controls (FIG. 2A and FIGS. 7A-F and 8A-B). To assess assay performance in discriminating healthy from MI plasma a Receiver Operator Characteristic (ROC) curve was plotted. The area under the curve (AUC) was 0.9345, indicating high sensitivity and specificity (FIG. 2B). The present inventors also compared cardiac cfDNA to standard cardiac damage markers CPK and troponin. Compared with healthy controls, cardiac cfDNA was significantly higher in MI patients that had CPK just above normal (<200), and was even higher in patients with high CPK (>200) (FIG. 2C). Similarly, cardiac cfDNA was higher than normal in plasma specimens that had either low or high levels of troponin (FIG. 2D and FIGS. 7A-F). Among the 6 specimens that had troponin levels above baseline but <0.03, there was no more cfDNA than in healthy controls (FIG. 2D).

A comparison of troponin levels to cardiac cfDNA in 57 specimens from MI patients yielded Spearman correlation value of 0.7975 and p<0.0001 (FIG. 2E). When plotting cardiac cfDNA vs troponin and marking on each axis the threshold of a positive signal, it was found that 79% of the MI specimens were positive for both troponin and cardiac cfDNA, and 7% were negative for both. 11% were positive only for troponin, and 4% were positive only for cardiac cfDNA (FIG. 2F). Importantly, total levels of cfDNA in MI did not correlate with troponin or CPK, nor with the percentage of cardiac cfDNA (FIGS. 7A-F). This reflects that fact that total cfDNA integrates all recent cell death events, including contributions from tissues that mask the cardiac signal. Thus, it is essential to calculate the specific contribution of the heart to cfDNA in order to assess cardiac damage. The sense and antisense markers correlated well in the MI plasma specimens (FIGS. 7A-F).

Finally, the present inventors examined the dynamics of cardiac cfDNA before and after angioplasty (Percutaneous Coronary Intervention, PCI). PCI causes the release of trapped cardiac material into blood, hence increased levels of troponin post PCI are typical of successful reperfusion. Cardiac cfDNA levels increased dramatically in most patients after PCI (FIG. 3A and supplemental FIGS. 8A-B), further supporting authenticity of the signal. A more detailed time course on a smaller group of patients revealed that cardiac cfDNA levels rose quickly after PCI and returned to baseline after 1-2 days, showing similar kinetics to troponin and CPK (FIG. 3B and supplemental FIGS. 8A-B). Importantly, the cardiac cfDNA signal was sufficient to distinguish people with MI prior to intervention (0-2 hours after onset of chest pain) from healthy individuals (AUC=0.7616, p=0.0044, FIG. 3C).

It can be concluded that measurements of cardiac cfDNA captures cardiomyocyte cell death associated with myocardial infarction, and that the cardiac cfDNA assay can in principle identify MI before intervention.

Cardiomyocyte cfDNA in Patients with Sepsis

Some septic patients have elevated levels of troponin and CPK[14], although they do not show clinical evidence of cardiac damage[15, 16]. The biological significance of this observation is disputed, since high troponin could represent either cardiomyocyte death, or alternatively transient stress absent of cell death. Since renal dysfunction is common in sepsis, the elevation in circulating troponin may also result from slower clearance, rather than faster release of troponin[17]. Since cfDNA is a stronger marker of cell death and is cleared by the liver[18], it was reasoned that measurements of cardiac cfDNA can be informative in this setting.

The present inventors determined the levels of cardiac cfDNA in a cohort of 100 patients with sepsis, for which 201 plasma specimens were available. Cardiac cfDNA was assessed blindly, and values were correlated to other biomarkers and to clinical parameters.

Septic patients had high levels of total cfDNA, reflective of broad tissue damage (FIGS. 9A-C), as reported[19]. Strikingly, many patients had high levels of cardiac cfDNA, similar in magnitude to the acute setting of MI (FIG. 4A). These findings argue strongly that in many septic patients, massive cardiomyocyte death occurs. The sense and antisense markers of FAM101A correlated well, supporting specificity of the signal (FIGS. 9A-C). Cardiac cfDNA and troponin levels did not correlate in the sepsis, unlike the situation in MI (FIG. 4B). This is not surprising, given the chronic nature of tissue damage in sepsis, which is expected to involve a major contribution of clearance rates on the actual measurements of biomarkers. A dramatic elevation of cardiac cfDNA was seen also in septic patients with normal renal function (data not shown), supporting the idea that cardiac cfDNA reflects cell death and not altered clearance rate.

The present inventors attempted to correlate the levels of cardiac cfDNA with clinical parameters recorded for the sepsis patients. The presence of cardiac cfDNA was strongly correlated with short-term mortality (FIG. 4C). When excluding cases with sepsis in the background of advanced cancer, patients with cardiac cfDNA were 4 times more likely to die within 90 days of hospitalization than patients with no cardiac cfDNA. The correlation was stronger than the correlation between troponin and mortality or between total cfDNA and mortality, but weaker than the correlation between age and mortality. These findings indicate that cardiac function is a central determinant of patient survival under sepsis, and that cardiac cfDNA can be used as a prognostic biomarker in sepsis.

A Modified Digital Droplet PCR Procedure for Measurement of Cardiac cfDNA

In order to translate analysis of cfDNA to a simpler and faster PCR format, the present inventors established a procedure using digital droplet PCR (ddPCR) to accurately count the number of molecules carrying the cardiac methylation signature at the FAM101A locus. They designed the assay to simultaneously interrogate 5 CpGs in the locus using two fluorescent probes, each capturing 2 or 3 unmethylated cytosines (FIG. 5A), leveraging the increased specificity attributed to regional methylation status[9].

ddPCR analysis of cardiomyocyte and leukocyte DNA revealed that each probe alone was able to discriminate between DNA from the two sources, with a signal to noise ratio of 50 to 58. However, when only droplets positive for both probes were scored, the cardiomyocyte:leukocyte signal ratio increased to 258, affording a 5 fold increase in specificity (FIG. 5B). ddPCR on cardiac DNA spiked with leukocyte DNA gave a signal that increased linearly with the amount of cardiac DNA; scoring only dual-labeled probes gave a lower baseline signal than scoring individual probes, better reflecting cardiomyocyte contribution to the mixture (FIG. 5C).

Finally, the ddPCR assay was tested on plasma specimens. ddPCR revealed a clear signal in the plasma of MI patients and was able to distinguish well between controls and patients. A lower baseline signal was observed in healthy individuals when scoring only dual-labeled probes, indicating increased specificity (FIG. 5D). It can be concluded that the ddPCR assay for cardiac cfDNA provides a rapid and simple alternative to sequencing-based assays.

Example 2

Monitoring Liver Damage Using Hepatocyte-Specific Methylation Markers in Cell-Free Circulating DNA Materials and Methods
Digital Droplet PCR.

Bisulfite-treated cfDNA was interrogated using methylation-sensitive TaqMan™ probes. The limited length of probes (up to 30 bp) dictated that they could cover only 2 to 4 informative CpG sites. In the IGF2R locus 4 CpGs were covered. However, in the VTN=locus, only 2 CpGs were covered by a probe predicting a relatively high frequency of "noise" (positive droplets) in DNA from non-liver tissue. Two TaqMan™ probes were designed, each recognizing lack of methylation in a different cluster of cytosines (each containing 2 CpG sites) within the same amplified 100 bp fragment from the VTN locus. Each probe was labeled with a different fluorophore, such that it was possible to identify droplets in which both probes found a target. Such droplets would be interpreted as containing a VTN cfDNA fragment in which all 4 targeted cytosines were unmethylated. This resulted in a ddPCR assay with the improved specificity afforded by interrogating multiple cytosines on the same DNA molecule.

Each 20 µL, volume reaction mix consisted of ddPCR™ Supermix for Probes (No dUTP) (Bio-Rad), 900 nM primer, 250 nM probe, and 2 µL of sample. The mixture and droplet generation oil were loaded onto a droplet generator (Bio-Rad). Droplets were transferred to a 96-well PCR plate and sealed. The PCR was run on a thermal cycler as follows: 10 minutes of activation at 95° C., 47 cycles of a 2 step amplification protocol (30 s at 94° C. denaturation and 60 s at 56° C.), and a 10-minute inactivation step at 98° C. The PCR plate was transferred to a QX100 Droplet Reader (Bio-Rad), and products were analyzed with QuantaSoft (Bio-Rad) analysis software. Discrimination between droplets that contained the target (positives) and those that did not (negatives) was achieved by applying a fluorescence amplitude threshold based on the amplitude of reads from the negative template control.

Probe and Primer Sequences:
VTN:
Probe 1—SEQ ID NO: 128
Probe 2—SEQ ID NO: 129
Primer 1—forward SEQ ID NO: 131
Primer 2—reverse—SEQ ID NO: 132.
IGF2R:
Probe 1—SEQ ID NO: 130
Primer 1—forward—SEQ ID NO: 133
Primer 2—reverse—SEQ ID NO: 134
Results Primers were designed for digital droplet PCR (ddPCR) after bisulfite conversion of cfDNA, and probes were designed that recognize blocks of unmethylated CpGs in the amplified marker regions. In this example, the present inventors focused on the VTN and IGF2R markers, which had multiple CpGs in close proximity.

ddPCR using both amplicons showed no signal in leukocyte DNA and a strong signal in hepatocyte DNA (FIG. 14A). Next, the present inventors examined 6 sets of plasma samples from 6 patients before and after liver transplantation. The ddPCR assay revealed a strong and transient elevation of hepatocyte cfDNA in plasma shortly after transplantation, which declined thereafter, strongly suggesting validity of the assay (FIG. 14B).

Example 3

List of Additional Identified Targets

A list of identified targets is provided in Table 1 and 2 herein below. The methylation signature of the targets can be used to identify a cell type of the listed organ. It will be appreciated that the sequences provided are 500 base pairs. Preferably the target sequence (which is amplified which is less than all the 500 base pairs) comprises the nucleotides CG which are at position 250 and 251 of each of these sequences and additional nucleotides up and/or downstream of this site.

TABLE 1

| Organ | Name | SEQ ID NO: |
|---|---|---|
| Acinar | CPA1 | 2 |
| Acinar | LMF2 | 3 |
| Acinar | NCLN | 4 |
| Acinar | BRF1 | 5 |
| Acinar | FRY | 6 |
| Astrocytes | HDAC4 | 7 |
| Astrocytes | AGAP1 | 8 |
| Astrocytes | AST1 | 9 |
| Astrocytes | PRDM | 10 |
| Astrocytes | FOXP4 | 11 |
| Astrocytes | KIAA | 12 |
| Astrocytes | PRDM2 | 13 |
| Astrocytes | WWOX | 14 |
| B cells | LRP5 | 15 |
| B cells | SORL1 | 16 |
| B cells | TRPV1 | 17 |
| BETA | INSh | 18 |
| BETA | MTG1 | 19 |
| BETA | ZC3H3 | 20 |
| BETA | Leng8 | 21 |
| BETA | Fbxw8 | 22 |
| BETA | Fbxl19 | 23 |
| Blood | Loc1/AGAP2 | 24 |
| Blood | PTPRCAP | 25 |
| BRAIN | MAD1L1 | 26 |
| BRAIN | PTPRN2 | 27 |
| BRAIN | WM1 | 28 |
| BRAIN | MBP | 29 |
| BRAIN | NUMBLE | 30 |
| BRAIN | LRRN3 | 31 |
| BRAIN | cg0978 | 32 |
| BRAIN | ZNF238 | 33 |
| Brain | WB1 | 34 |
| Brain | UBE4B | 35 |
| Breast | KRT19 | 36 |
| Breast | LMX1B | 37 |
| Breast | ZNF296 | 38 |
| CD8 cells | CD8A | 39 |
| CD8 cells | CD8A anti | 40 |
| CD8 cells | CD8B | 41 |
| CD8 cells | CD8B anti | 42 |
| Colon | FGFRL1 | 43 |
| Colon | FAT1 | 44 |

TABLE 1-continued

| Organ | Name | SEQ ID NO: |
|---|---|---|
| Colon | col1 | 45 |
| Colon | MG1 | 46 |
| Colon | colnp | 47 |
| Colon | col2np | 48 |
| Colon | ECH1 | 49 |
| Colon | ECH1 | 50 |
| Colon | CNL (my name) | 51 |
| Colon | MAP7D1 | 52 |
| Colon | col3np (my name) | 53 |
| Eosinophils | PCYT1A | 54 |
| Eosinophils | PCYT1A anti | 55 |
| Heart | FAM101A | 56 |
| Heart | FAM101A AS | 57 |
| kidney | cg00256155 | 58 |
| kidney | PAX2 | 59 |
| kidney | cg15767955 | 60 |
| kidney | MCF2L | 61 |
| kidney | HOXC4 | 62 |
| kidney | PAX2 | 63 |
| Liver | ITIH4 | 64 |
| Liver | SEBOX; VTN | 65 |
| Liver | IGF2R | 66 |
| LUNG | SFTP/A1 | 67 |
| LUNG | SFTP/A2 | 68 |
| LUNG | CLDN18 | 69 |
| LUNG | RAB4 | 70 |
| LUNG | CHST | 71 |
| LUNG | SFTPC | 72 |
| Melanocytes | GALNT3-B | 73 |
| Melanocytes | Melanol | 74 |
| Melanocytes | Melanol anti | 75 |
| Melanocytes | RNF207-A | 76 |
| Melanocytes | RNF207-A anti | 77 |
| Melanocytes | RNF207-B | 78 |
| Melanocytes | RNF207-B anti | 79 |
| Monocytes | TCF7L2 | 80 |
| Monocytes | MONO1 | 81 |
| Muscle | MAD1L1 | 82 |
| Muscle | TPO | 83 |
| Muscle | TNNI2 | 84 |
| Muscle | TRIM72; PYDC1 | 85 |
| Neuron | ZNF509 | 86 |
| Neuron | ITFG3 | 87 |
| Neuron | CTBP2 | 88 |
| Neuron | SLC38A10 | 89 |
| neutrophils | DENND3 | 90 |
| neutrophils | NEUT1 | 91 |
| NK | RFC2 | 92 |
| Oligodendrocytes | PLEK | 93 |
| Oligodendrocytes | EVI5L | 94 |
| Oligodendrocytes | ZFP57 | 95 |
| Oligodendrocytes | DNAH | 96 |
| Oral cavity | hH&N1 | 97 |
| Oral cavity | CALML3 | 98 |
| Oral cavity | hH&N4 | 99 |
| Pancreas | CUX2 | 100 |
| Pancreas | PAN4 | 101 |
| Pancreas | REG1A | 102 |
| Pancreas | FRY | 103 |
| Pancreas | BRF1 | 104 |
| Pancreas | PRDM16 (not the same as above) | 105 |
| Pancreatic duct | PRDM16 | 106 |
| Small intestine | ST5 | 107 |
| Small intestine | BANP | 108 |
| Small intestine | SS18L1 | 109 |
| T cells | PRKCH | 110 |
| T cells | SPATA13 | 111 |
| Thyroid | ZNF500 | 112 |
| Thyroid | ATP11A | 113 |
| Treg | FOXP3 | 114 |
| Treg | FOXP3 ANTI | 115 |
| Treg | FOXP3 TSDR | 116 |
| Treg | FOXP3 TSDR anti | 117 |

TABLE 2

| Organ | Name | SEQ ID NO: |
|---|---|---|
| B cells | NAT10 | 135 |
| BETA | GALNTL4 | 136 |
| BETA | cg06081580 | 137 |
| BETA | RGS9 | 138 |
| BETA | DLG5 | 139 |
| BETA | GNAS | 140 |
| BETA | TTC15 | 141 |
| BETA | MAD1L1 | 142 |
| BETA | cg22406334 | 143 |
| BETA | ZDHHC14 | 144 |
| BETA | ZC3H3_a | 145 |
| BETA | SDK1 | 146 |
| BETA | SFRS16 | 147 |
| BETA | PUS3 | 148 |
| BETA | ZC3H3-c | 149 |
| BETA | ACSF3 | 150 |
| BETA | cg19441717 me | 151 |
| White Blood Cells | SNX11 | 152 |
| Cardiomyocytes | Cardio C | 153 |
| Cardiomyocytes | Cardio D | 154 |
| Cardiomyocytes | Cardio E | 155 |
| Cardiomyocytes | Cardio I | 156 |
| Cardiomyocytes | Cardio J | 157 |
| Colon | CNL2 | 158 |
| Colon | CNL | 159 |
| Colon | col3np | 160 |
| Eosinophils | HTT | 161 |
| Eosinophils | ACOT7 | 162 |
| Kidney | ATP11A | 163 |
| Kidney | PAX2-6032 | 164 |
| Kidney | cg00256155 | 165 |
| Kidney | PAX2-818 | 166 |
| Kidney | MCF2L | 167 |
| LUNG | LUAD1 | 168 |
| LUNG | LUAD5 | 169 |
| LUNG | LUSC2 | 170 |
| LUNG | LUSC3 | 171 |
| LUNG | S3-unMe | 172 |
| LUNG | S4-unMe | 173 |
| LUNG | S5-unMe | 174 |
| LUNG | S5-Meth | 175 |
| LUNG | S10-unMe | 176 |
| LUNG | S11 -unMe | 177 |
| LUNG | S13-unMe | 178 |
| LUNG | S12-Meth | 179 |
| Melanocytes | RNF207-A | 180 |
| Melanocytes | RNF207-B | 181 |
| Melanocytes | melano1 | 182 |
| Neutrophils | HIPK3 | 183 |
| Oligodendrocyte | NMRAL1 | 184 |
| Oligodendrocyte | TAF8 | 185 |
| Tongue | PIGG | 186 |
| Tongue | MAD1L1 | 187 |
| Tongue | TP73 | 188 |
| Tongue | BAIAP2 | 189 |
| Tongue | HN1L | 190 |
| T regs | FOXP3 TSDR | 191 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Hickman, P. E. et al. Cardiac troponin may be released by ischemia alone, without necrosis. *Clin Chim Acta* 411, 318-323 (2010).
2. Michielsen, E. C., Wodzig, W. K. & Van Dieijen-Visser, M. P. Cardiac troponin T release after prolonged strenuous exercise. *Sports medicine* 38, 425-435 (2008).
3. Roca, E. et al. The Dynamics of Cardiovascular Biomarkers in non-Elite Marathon Runners. *J Cardiovasc Transl Res* (2017).
4. Katus, H. A., Remppis, A., Scheffold, T., Diederich, K. W. & Kuebler, W. Intracellular compartmentation of cardiac troponin T and its release kinetics in patients with reperfused and nonreperfused myocardial infarction. *Am J Cardiol* 67, 1360-1367 (1991).
5. Bianchi, D. W. et al. DNA sequencing versus standard prenatal aneuploidy screening. *The New England journal of medicine* 370, 799-808 (2014).
6. Dawson, S. J. et al. Analysis of circulating tumor DNA to monitor metastatic breast cancer. *The New England journal of medicine* 368, 1199-1209 (2013).
7. Snyder, T. M., Khush, K. K., Valantine, H. A. & Quake, S. R. Universal noninvasive detection of solid organ transplant rejection. *Proc Natl Acad Sci USA* 108, 6229-6234 (2011).
8. De Vlaminck, I. et al. Circulating cell-free DNA enables noninvasive diagnosis of heart transplant rejection. *Sci Transl Med* 6, 241ra277 (2014).
9. Lehmann-Werman, R. et al. Identification of tissue-specific cell death using methylation patterns of circulating DNA. *Proc Natl Acad Sci USA* 113, E1826-1834 (2016).
10. Sun, K. et al. Plasma DNA tissue mapping by genome-wide methylation sequencing for noninvasive prenatal, cancer, and transplantation assessments. *Proc Natl Acad Sci USA* 112, E5503-5512 (2015).
11. Guo, S. et al. Identification of methylation haplotype blocks aids in deconvolution of heterogeneous tissue specimens and tumor tissue-of-origin mapping from plasma DNA. *Nat Genet* 49, 635-642 (2017).
12. Roadmap Epigenomics, C. et al. Integrative analysis of 111 reference human epigenomes. *Nature* 518, 317-330 (2015).
13. Bergmann, O. et al. Dynamics of Cell Generation and Turnover in the Human Heart. *Cell* 161, 1566-1575 (2015).
14. Turner, A., Tsamitros, M. & Bellomo, R. Myocardial cell injury in septic shock. *Crit Care Med* 27, 1775-1780 (1999).
15. Sanfilippo, F. et al. Diastolic dysfunction and mortality in septic patients: a systematic review and meta-analysis. *Intensive care medicine* 41, 1004-1013 (2015).
16. Hochstadt, A., Meroz, Y. & Landesberg, G. Myocardial dysfunction in severe sepsis and septic shock: more questions than answers? *J Cardiothorac Vasc Anesth* 25, 526-535 (2011).
17. Friden, V. et al. Clearance of cardiac troponin T with and without kidney function. *Clin Biochem* (2017).
18. Gauthier, V. J., Tyler, L. N. & Mannik, M. Blood clearance kinetics and liver uptake of mononucleosomes in mice. *J Immunol* 156, 1151-1156 (1996).
19. Rhodes, A., Wort, S. J., Thomas, H., Collinson, P. & Bennett, E. D. Plasma DNA concentration as a predictor of mortality and sepsis in critically ill patients. *Critical care* 10, R60 (2006).
20. Shave, R. et al. Exercise-induced cardiac troponin elevation: evidence, mechanisms, and implications. *J Am Coll Cardiol* 56, 169-176 (2010).
21. Lo, Y. M. et al. Rapid clearance of fetal DNA from maternal plasma. *Am J Hum Genet* 64, 218-224 (1999).
22. Simpson, J. T. et al. Detecting DNA cytosine methylation using nanopore sequencing. *Nature methods* 14, 407-410 (2017).

What is claimed is:

1. A method of analyzing the methylation status of methylation sites of a double-stranded DNA molecule which comprises at least two methylation sites per single strand of said double-stranded DNA molecule, the double-stranded DNA molecule being comprised in a specimen, the method comprising:
   (a) contacting the double-stranded DNA with bisulfite to generate single-stranded DNA molecules of which demethylated cytosines of said single-stranded DNA molecules are converted to uracils;
   (b) fractionating the specimen into a plurality of specimen fractions wherein more than 50% of the fractions contain no more than one single-stranded DNA molecule per specimen fraction;
   (c) contacting said single-stranded DNA with amplification primers under conditions that generate amplified DNA from said single-stranded DNA; and
   (d) determining the methylation status of said at least two methylation sites of said single-stranded DNA molecule in at least one of said specimen fractions, wherein a methylation status of each of said at least two methylation sites on said single-stranded DNA molecule is indicative of the methylation status of methylation sites of a double-stranded DNA molecule; wherein said determining comprises contacting said amplified DNA with:
   (i) a first probe that hybridizes to said amplified DNA at a site which comprises the first of said at least two methylation sites; and
   (ii) a second probe that hybridizes to said amplified DNA at a site which comprises a second of said at least two methylation sites, wherein said first probe and said second probe are labeled with non-identical detectable moieties.

2. The method of claim 1, wherein
   a. said double-stranded DNA molecule is no longer than 150 bp;
   b. said at least two methylation sites are not more than 150 bp apart;
   c. wherein each strand of said double-stranded DNA comprises at least four methylation sites; or
   d. wherein each strand of said double-stranded DNA comprises at least four methylation sites which are not more than 150 bp apart.

3. The method of claim 1, wherein said first probe and said second probe comprise a quenching moiety;
   wherein said contacting is effected under conditions that separate said quenching moiety from said first probe and said second probe to generate a non-quenched first probe and a non-quenched second probe; and
   wherein the method further comprises analyzing the amount of said non-quenched first probe and said non-quenched second probe in at least one specimen fraction of said plurality of specimen fractions.

4. The method of claim 1, wherein said double-stranded DNA molecule is differentially methylated in a cell or tissue of interest.

5. The method of claim 4, wherein said cell of interest is selected from the group consisting of a pancreatic beta cell, a pancreatic exocrine cell, a hepatocyte, a brain cell, a lung cell, a uterus cell, a kidney cell, a breast cell, an adipocyte, a colon cell, a rectum cell, a cardiomyocyte, a skeletal muscle cell, a prostate cell and a thyroid cell or wherein said tissue is selected from the group consisting of pancreatic tissue, liver tissue, lung tissue, brain tissue, uterus tissue, renal tissue, breast tissue, fat, colon tissue, rectum tissue, cardiac tissue, skeletal muscle tissue, prostate tissue and thyroid tissue.

6. The method of claim 5, wherein said tissue is cardiac tissue and wherein said double-stranded DNA molecule is non-methylated in cells of cardiac tissue and methylated in leukocytes.

7. The method of claim 6, wherein said double-stranded DNA molecule comprises a sequence which is comprised in SEQ ID NOs: 56 or 57.

8. The method of claim 5, wherein said tissue is liver tissue and wherein said double-stranded DNA molecule comprises a sequence which is comprised in SEQ ID NOs: 65 or 66.

9. The method of claim 3, wherein said first probe comprises a sequence as set forth in SEQ ID NO: 118 and said second probe comprises a sequence as set forth in SEQ ID NO: 119, said first probe comprises a sequence as set forth in SEQ ID NO: 128 and said second probe comprises a sequence as set forth in SEQ ID NO: 129 or said first probe comprises a sequence as set forth in SEQ ID NO: 125 and said second probe comprises a sequence as set forth in SEQ ID NO: 126.

10. The method of claim 3, wherein the sequence of said first probe is selected such that said first probe binds to said amplified DNA when said methylation site of said double-stranded DNA molecule is non-methylated or wherein the sequence of said second probe is selected such that said second probe binds to said amplified DNA when said methylation site of said double-stranded DNA molecule is non-methylated.

11. The method of claim 3, wherein said non-identical detectable moieties are FAM and HEX.

12. The method of claim 1, wherein
 a. said double-stranded DNA is cell-free DNA;
 b. said double-stranded DNA is cellular DNA and wherein said method further comprises lysing the cells of said cellular DNA prior to said determining;
 c. said specimen is a fluid specimen;
 d. said specimen is a body fluid specimen;
 e. said specimen is a body fluid specimen selected from the group consisting of blood, plasma, sperm, milk, urine, saliva and cerebral spinal fluid;
 f. said specimen comprises DNA from a plurality of cell-types;
 said specimen is blood; or
 g. said method further comprises quantitating the amount of DNA of said cell or tissue origin.

13. The method of claim 1, wherein said first probe hybridizes to the forward strand of said amplified DNA and said second probe hybridizes to the reverse strand of said amplified DNA.

14. The method of claim 1, wherein said DNA molecule comprises at least four methylation sites per single strand, said first probe hybridizes to said amplified DNA at a site which comprises at least two methylation sites of said four methylation sites and said second probe hybridizes to said amplified DNA at a site which comprises at least two methylation sites of said four methylation sites.

* * * * *

SEQUENCE LISTING

<160> NUMBER OF SEQ ID NOS: 191

<210> SEQ ID NO 1
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 1
tatggtttgg taatttattt agag                                          24

<210> SEQ ID NO 2
<211> LENGTH: 500
<212> TYPE: DNA
<213> ORGANISM: homo sapiens

<400> SEQUENCE: 2
tgtccctgcc tgctgtcctg gctggtgccc ccagcccgct gtgaccgtgc cggctcttgt      60
cctccccagc tggacttctg gcgggggcct gcccaccctg gctcccccat cgacgtccga     120
gtgcccttcc ccagcatcca ggcggtcaag atctttctgg agtcccacgg catcagctat     180
gagaccatga tcgaggacgt gcagtcgctg ctggacgagg agcaggagca gatgttcgcc     240

| | |
|---|---|
| ttccggtccc gggcgcgctc caccgacact tttaactacg ccacctacca caccctggag | 300 |
| gaggtgaggg cgccctagc ggccgctccc tgcagccacc agctcttcat catggctggt | 360 |
| agaacgcggt agggccaagg ccagggccag cctgggtgtg cgcagcgcct gctctgtttc | 420 |
| catgtggcct gtgtggtcgt agctccattg cagggctcgc agcaggctgg gacggtgggg | 480 |
| ctgctaaggg aagcatctgg | 500 |

<210> SEQ ID NO 3
<211> LENGTH: 500
<212> TYPE: DNA
<213> ORGANISM: homo sapiens

<400> SEQUENCE: 3

| | |
|---|---|
| ccgctctcag tgctcccgga gactgacgcc tggccccgtg gcaggcaccc acctccaccc | 60 |
| tgcagggtgc atccctctgc tacaaggcct cccaacagc ggttgccagc tgtccccggg | 120 |
| agccacgctg tccccaacag gcacgctga cagcgctga aggccgagcc ctgtctgcct | 180 |
| ctctctgaca gctgcggccc tcacccacct gcgagtagaa agcagccaag cgcaggcgtc | 240 |
| gaatgggggc gaagaacagg ggcggcacag cgatctcaat taggaaggtg gccaccacgc | 300 |
| tgagcttgtg cagccagacc ggcaggtggt gtgcgaacca ggcggcgggc gtgggcaggc | 360 |
| actgggtctc gtagtggtag gtgagggctg caggcgaggg caggagtcag ggctggccga | 420 |
| gccccccagac taccccaggt ccagaccggg cccctcacca gtgagccccc accacgcagg | 480 |
| gcagcggctg gtcagcttga | 500 |

<210> SEQ ID NO 4
<211> LENGTH: 500
<212> TYPE: DNA
<213> ORGANISM: homo sapiens

<400> SEQUENCE: 4

| | |
|---|---|
| tggtgacttc tctcaggatg cccggtgccc tccatggcgt ccaccacaag tggtctcagc | 60 |
| ccattcagac gcgggtctga gggagttggt gctggtttcg cctccgcaga gggccgtgtc | 120 |
| cacactagct tgtggccacc cggcccgacc ctggcccctcg agggaggctg ggccaccca | 180 |
| aggccatctg ttctcctggg gagatgggcc ttggccacag agagcccttg ccattgggcc | 240 |
| ccgagcgagc gggggctggg atccagaggg cagtgtggcc ttggctggtg ctgacgcgag | 300 |
| gcggggctcc gatgggcggg gcttcggaat gggaggccgt ggccttcagg gagctctggg | 360 |
| tgctggtgtc ccctccgtt cctctgactt gctgctgctc cttcccttct ccctcctcgc | 420 |
| tcactcccta tcccgcctgc gggagctcga ggcccggaga acgggggtgc ctgccagttg | 480 |
| gcctcatctc ccggccccaa | 500 |

<210> SEQ ID NO 5
<211> LENGTH: 500
<212> TYPE: DNA
<213> ORGANISM: homo sapiens

<400> SEQUENCE: 5

| | |
|---|---|
| agggctgcag gcccagggcc agatcctgac ttgcccaccc gccggctgtg tgaccttcag | 60 |
| cgcgcgacta acctctctgt gcctatttcc tcgaggaaaa tgccgggaaa tagcagcgcc | 120 |
| tgcccctgta aagccctcag agcagagtgg accgcgctct ctgcaagcgc tggctgctgg | 180 |
| cgtccgtagc aagctaaatc gcgaagcatc tgaacgaacg aggaagccca acgaccatcc | 240 |

```
cacaggccgc ggccagaggc agactccgga atgcaaatgg ccaaacaagc aggtccacct    300
gcgttcctaa ccaaaagatc gctaactgaa gaacgggcgc aagcacctgc gcatggcact    360
gcgggtctgg gggcggccgc ctgccagcgc cgggagccgc cttccacggc tacctctgca    420
cagcgcgcgg ctcgcgccgg ttgctgggca gaagctcgag cagcttcgag gatgtcgggc    480 ctggggggcgg ggccgcgagg                                               500

<210> SEQ ID NO 6
<211> LENGTH: 500
<212> TYPE: DNA
<213> ORGANISM: homo sapiens

<400> SEQUENCE: 6
aaagcagcgc ggccgccgcc tccgagggct gcagggagat cagcgtccag caaataagaa     60
gcaagtcctg gacccggagg aggaggagcg gccgagcatc tctctctgct ccgccgtgtc    120
ctttagatga gcactcccgg ccggagccgg aggtggatcc gcagagctgc ctctgggcgc    180
ctgaccccgc gctgacatca caacctgtga caggcgcatc acgcccggta cctgctcccg    240
gccgctgccc gtcctcccag cctctttgta tgccgcagac atggccagcc agcaggattc    300
gggcttcttt gagatcagta tcaaatattt actgaaatcc tggagtaata gtgagtaata    360 gaaataacc ttttgtttg tttgtttgct ggatgttgca taaggctgga gacagaaaat     420
ctcaactgga cacatatgtt tgtgagccgc ggaagttttt cttttttct tttcttttct     480 tttctctttc tttctttctt                                                500

<210> SEQ ID NO 7
<211> LENGTH: 500
<212> TYPE: DNA
<213> ORGANISM: homo sapiens

<400> SEQUENCE: 7
tccaccctcc ccgggaggcc ggctctcaga ggaccccgct acaggcccag aggccttgct     60
gacgtcattt ctagaggcca ataatgagaa aaataaagaa aaaggttgtg gctgttcaag    120
gaaaagcgcg ggcgccaggt ctcagccagg aagactgcct gtcctgctcc tcttcctcct    180
cttccatcga agtcaccgtg ccgctgtgag agccacaaga gcgtgtgccc cagaagtggt    240
ccagacagac gctcgagacc cggagcccgt ttccatggtg agacaagcgc ccccttggaa    300
aacatgttta ccagacacag ccaacgagac gtgctcctgg ctcttggcac aagtgcgttc    360
ctctgggcat gcgtttctgc acctcgcgaa gaaatggatt ttctgccctg tactaatgtg    420
ctattgagaa aaggctacaa gtaattttga tgaggaacag aagctgaatc aatttcattc    480
cttacaatca ataccaaatg                                                500

<210> SEQ ID NO 8
<211> LENGTH: 500
<212> TYPE: DNA
<213> ORGANISM: homo sapiens

<400> SEQUENCE: 8
agacaagatg tacacacctt tcccttgta gttttgggga gaattcttgt atatttttta     60
gtagcctaat acggtatttt gatgaggact ttgtaccacc ctccttgctg gagccaagtg    120
ttactcattt ggtaacctcc cggtcctggg aacacataac tgtgaaattc taggacaacg    180
tgatacagca gcgaatcaat taattctctg tatcaggagg gatctggtac accgagatac    240
taatgactcc gcgtccttct ccaaaggcag ccccacagaa ggcgggcgcc acgttaagct    300
```

| | |
|---|---:|
| gtgctgctgt cagcaagctg aaagctatgg gtctctgaca cggctctcaa ttgctagcag | 360 |
| gtttctctca ttgcacctca tttgcatctg ggacatcaat tagcatgttt gttgaggcta | 420 |
| attgaatgaa actcaatcat agctcttaat tgcttgacta tgtgaaaaga aatcacatta | 480 |
| atgcagctaa ttaagtgtac | 500 |

<210> SEQ ID NO 9
<211> LENGTH: 500
<212> TYPE: DNA
<213> ORGANISM: homo sapiens

<400> SEQUENCE: 9

| | |
|---|---:|
| agcctgtggc attggagagc atggtgcacc aggcactcgc ccgctgcaag ctcgctgccc | 60 |
| ccgcagtcgc cagctgtgat ctccctagg ggttcagacc caggagcaga gaggaggcag | 120 |
| cctgtggggg cttctcagct agaactggcg agaggaggag agagaaggtc caacctcagg | 180 |
| cctccaccca ccgtgggccg ggtatggat agacatggaa gtatgtgagc gtggacatcc | 240 |
| atgcgcacgc gcacaggcac acggggagaa ccctcttcct cttccccatc agccctctg | 300 |
| gtttttggtg ctcccagacg tgcgctgagt gcatgagggc ctcctcaaag accgagtgag | 360 |
| ggtcaccaca agctcttgcc aagacagttt taaatatgag attcctccaa ggtccctggg | 420 |
| ggacatagga aaaaaagaa gtaagcctct gagtccctcg ctccttcag cactgctgtc | 480 |
| gggcttggaa tatgaatgac | 500 |

<210> SEQ ID NO 10
<211> LENGTH: 500
<212> TYPE: DNA
<213> ORGANISM: homo sapiens

<400> SEQUENCE: 10

| | |
|---|---:|
| agattctttt tcttgaaata ccagaggttg gtggagggat ttttgcggca cctgaacagt | 60 |
| cctaagcagg cccatgccag cggcgtccca gctcctgggt gcaggatctg gtgcgcctgt | 120 |
| ctccatgagg atttggacca cgttcggcag agcaggtctc ccaggcttcc ctaaagatgt | 180 |
| ttaacaaaaa cagtggagat gattgggttt ggagtcgctt cctgggcaga gctgctcgtg | 240 |
| ttcgggcagc gctcagggca ctcggttgga cgtcgccagg gtggctcggc ccctccacgt | 300 |
| ggggcctcca caccacctct caggggctgc cacccttcc cgtcccccta gaccccaaga | 360 |
| ccccaaaacc acacatgggc taattgtggt aaaatataca aatgtaatct ttgtcatttt | 420 |
| aaccacccgt gagcgtggca ttaggtggcg ttcaatatgc ccgggccact gcggaaccat | 480 |
| caccccctctc tgtgcccagg | 500 |

<210> SEQ ID NO 11
<211> LENGTH: 500
<212> TYPE: DNA
<213> ORGANISM: homo sapiens

<400> SEQUENCE: 11

| | |
|---|---:|
| gttaatgttt cagcgtaacg aattagtctc tcatcacgaa tcaggcttcg aaatgaggga | 60 |
| aaaaagcccc ggtgaggcca tcctcggaaa ttggggtcat tctcatttgc aaagcggagg | 120 |
| atcggagccc cgtaatgcgg gcaaatttat tccgaggcag gagccccggc gtgattaggc | 180 |
| cctttgtaat tatcgctcca agagattcca ctccagccgc ccgcctccct cgtggattag | 240 |
| caagcgagtc ggaaaaatac acaggattta attagaggca aattaaaatt ggtaatgaaa | 300 |

```
tcgggccagt tgcaagtggc aagagttgga agggagagag ggagagggat ctccagggc      360 acgggctgcc tgccctaccc gctttcttcc ccgtttagaa atgtaaagag agacaagga      420 tggggacgag gcggggagg ctaagggagg acaggtaaca gggtccaggg atgcaggcag      480
ggatggtgat aactgggagc                                                 500

<210> SEQ ID NO 12
<211> LENGTH: 500
<212> TYPE: DNA
<213> ORGANISM: homo sapiens

<400> SEQUENCE: 12
tttctgggcc tgacctgagg ggacgtgggg gagggccgag gatgttccca atcctccact      60
ggcatttaaa tgagggctcc gacaggccca agaacacagg ccctccaaaa gccagctcag     120
cggtttgttg caaatgcagc cacacgtgac ctgactcaag atgggcttcg aggagatgaa     180 aggggggcgga actccaggct ggcccacgtg gcaggcgctg ccttgggcac caccgctcac     240
cccagcccac gcctggcacc cccagcccag ccaagcgcct ctgtttccaa acatgcctgt     300
tttaattagt gccgctctct gacaggtgaa ccgggtttat gtgattttcg atctgcctac     360
caccgtgtca atgatcaaac tgtggaatta tgcgaaaaca ccccatcgag gggtgaagga     420
gtttggcgta agtacttatt agctgagttt tttgagataa ttatgctcgt tggtaattag     480
gccgccggca attatcattt                                                 500

<210> SEQ ID NO 13
<211> LENGTH: 500
<212> TYPE: DNA
<213> ORGANISM: homo sapiens

<400> SEQUENCE: 13
gcgtgtccat gcgtgtgcac gtgtgcatgc gtgtgcgtgc gcgtgcatcc acgcctggcg      60
gcctgggccc ggcgtgagtg tgtgggtggg agcgggtgtg tatccgcggc tgctccattc     120
tgctgtaaag gctcgctgca gtgggcaaca tggaggagac atgaaagagg ggacaataaa     180
tagcttccta ccttgcctgg ataatgggcg agttctccgg gtggattaat cctcgcgtcg     240
tctttgggcc gtcagtttgg gagtgacagt aacaaggctc ccggggaccc tgctaatttg     300
cactccattc accggctcgt gaaaccgtca gggctgcgga aggactgcgc ggcgcgggcc     360
tccattcact gggagcctga tatactggga aaggggccag tgcgcacaaa gcccaaaaga     420
gcacatgggt gaggctttgt ccctcctctc ccgttccctt ttatgcggcc ttgtgctagt     480
taagctcctc atttgtcccc                                                 500

<210> SEQ ID NO 14
<211> LENGTH: 500
<212> TYPE: DNA
<213> ORGANISM: homo sapiens

<400> SEQUENCE: 14
ttctcgagcc cctgattgtc ttattaaata atttctttgc ctcttaagtg tggactcgga      60
gcactcgtgc tctgaaagcc ctcctgatta actatagcct tggcctcaag ttgattttat     120
aaacttcgga tggtgcccca gagggtgaag cttcctgttg tcaattctgc ccgttgctat     180
agataccaaa ctccacaatc agtaattaga gcgtgccccc tgcccagaa ctggtcaaac      240 ggtgcagagc gctcggcaaa tggtcttaaa agcatccgcg cttgcatgga aatgcatttc     300
caatggtgac gggtttgtt ttattcatgg acttttgaa aaaaaaatca ctggtttatt       360
```

```
ggaaaccata gagaagtata agtaattatt atgcttttta aaatacaacc gaggttcctc    420
atcatgatac gttaagggaa aggaagacag ggcaggaggg tggtgtggca caaaggcggc    480
tctgtctgac ctgtcacgtt                                                500
```

<210> SEQ ID NO 15
<211> LENGTH: 500
<212> TYPE: DNA
<213> ORGANISM: homo sapiens

<400> SEQUENCE: 15

```
atggggcgcg ggcttcagac ttcacaaagc agaccacgcg gcagcctggg gctttagtat     60
ccaaatgtcc tgccctccag gtttcattcc ttgccgtaaa atatcacgtt aaaggaaaat    120
gttttgttaa aagaccacag tcctgtcacc tgagcacagt cgctgttctc ggttcctctg    180
tggctttcca ggctgcaggt gcccattggt attgcggccg tgcgcccggc gggcatgaat    240
tagctgtgcc gcctggctgc tgacgggacg cctcgcctcg actgaaaact acctggagct    300
gctcacccag gggcaacgtg aagaaaacgt gaaattctgt cgcttgttgc agctgacagc    360
acggctgtga ggtcccagtg ggcagaggcc tcgtgcaggg cacctcacca gccgggatgt    420
cagagctggc cagaaggagc ggtgcccatg gagggctgcc agtgcccaga gagccttccg    480
aggtgtcacg ttgggcagtg                                                500
```

<210> SEQ ID NO 16
<211> LENGTH: 500
<212> TYPE: DNA
<213> ORGANISM: homo sapiens

<400> SEQUENCE: 16

```
gctttaaaat ttctctcttt ttttacgctg tcccttt att tctcagaccg gccgacactt     60
agggaaaata gaaagaacc tatgtgaaat atcgggggtg aatttcaccc gatatctggc    120
tgaatttccc ccgatagtta ctaaagggag ggaaactcaa aagagaaaga cctgtggtcc    180
agcagtaaga ataatattgg tttcatttcc tcccctgccg cactctgatg ggtagagaac    240
acctgtcttc gcaaccagta tcgctgcagc aacgggaact gtatcaacag catttggtgg    300
tgtgactttg acaacgactg tggagacatg agcgatgaga gaaactgccg tgagtcttct    360
ggattggacg ttaagcactt accattactc agaagcctgg ttggctcttc ccaggctgag    420
ggcctaaggt ctagggcgag ggccacccat gattggtgat gcccatctaa gttgatgggg    480
cttagatgac agagaaaaca                                                500
```

<210> SEQ ID NO 17
<211> LENGTH: 500
<212> TYPE: DNA
<213> ORGANISM: homo sapiens

<400> SEQUENCE: 17

```
ccaggtgggc tcaggagtg agatccagct ggcccctgaa ccaccggcct ccaaactccc      60
tctgtctctg cccaaacctc cccttagcaa aagccaaaaa gatcagggtc tgccacactg    120
tctccctacc gaagtagaat ccaggccgcc ctttggtttt cttaaagaag tccccatggg    180
ccgcagcctg gacgtctgct ccgttctcca ccaggagggt caccagggcc atgttgcgtc    240
tctcgatggc gatgtgcagt gctgtctggc tacagagga cgcgcacggt tggcttcgtg    300
gtcacggtcc tgtggggctg ccgggacagg tgctggggaa gggctctggg caggcagcag    360
```

```
ctgctgcagg aggaactggg cagaaagtgc ctggaggacc cccccactgc aggaggccag      420
gccagggtcc cccaaggggt cccagcaagg tcctgagaca ggagacccct gggaacagga      480
aataacgggt tggaagccag                                                  500
```

<210> SEQ ID NO 18
<211> LENGTH: 500
<212> TYPE: DNA
<213> ORGANISM: homo sapiens

<400> SEQUENCE: 18

```
ccagctctgc agcagggagg acgtggctgg gctcgtgaag catgtggggg tgagcccagg       60
ggccccaagg cagggcacct ggccttcagc ctgcctcagc cctgcctgtc tcccagatca      120
ctgtccttct gccatggccc tgtggatgcg cctcctgccc ctgctggcgc tgctggccct      180
ctggggacct gacccagccg cagcctttgt gaaccaacac ctgtgcggct cacacctggt      240
ggaagctctc tacctagtgt gcggggaacg aggcttcttc tacacaccca agacccgccg      300
ggaggcagag gacctgcagg gtgagccaac tgcccattgc tgcccctggc cgcccccagc      360
caccccctgc tcctggcgct cccacccagc atgggcagaa ggggcagga ggctgccacc      420 cagcaggggg tcaggtgcac ttttttaaaa agaagttctc ttggtcacgt cctaaaagtg      480
accagctccc tgtggcccag                                                 500
```

<210> SEQ ID NO 19
<211> LENGTH: 500
<212> TYPE: DNA
<213> ORGANISM: homo sapiens

<400> SEQUENCE: 19

```
tcagagttcg agactagcct ggccaacatg gtgaaacccc atctctacta aaaatacaaa       60
aaaagtagcc gggcgtggtg gtgcgcacct gtagtcccag ctactcagga ggctaaggca      120
ggagaactgc ttgaacccccg ggaggcggag gttgcagtga ccaagatca cgccactgca      180 ctccagcctg gcgacagagc gagactccgt ctcaaaaata aaaattccgg tagagtaata      240
ctcttgtaac gcagtgtgca attgagcagt tgctgactgc tgatttagag ttgaaatccg      300
actatattta tgtctagtct tggacagtgg agaatatttc agcctcatta attaatcggt      360
ttaatttagc agaactgcag tcagtatttg gaaacagttt gttatattaa accctgaagt      420
acttgaggct gcgcgcggtg gctcatgcct gtaatcccag cattttggga ggccgagaca      480
ggtagatcac ttgaggtcag                                                 500
```

<210> SEQ ID NO 20
<211> LENGTH: 500
<212> TYPE: DNA
<213> ORGANISM: homo sapiens

<400> SEQUENCE: 20

```
tgtggctctt taacaagcca tcgctttatg aagcaaggtt aacaatttca cttgattcag       60
tggaatatta taaactctct ggggcccatt tgaggacttc tacttcaggc gcaaggtgac      120
gattcagcac ttttcacatt atttagagaa taaaattaac cctcgcaggc ccgggctgcc      180
gcctgtcccc gctggatctg gccggctcag cgctttccca tatataatta caagctgcta      240
tccatcatgc gggcgccgcg gcgcggacac acggaaaggc agcagtaagc acttccacta      300
atagaagcag gacctaaata tcactttgat attttcattt aaatcgaaac attttacaat      360
aatcagccat ggcctccatg gggatcctgc cactgccccc acagggtctg ggctgccccc      420
```

```
agccaggccc tacctccccg gagggggattg cctgccaggt ttcaggttgg ggagcccggc    480
ctggccaacc cttggcccgg                                                 500

<210> SEQ ID NO 21
<211> LENGTH: 500
<212> TYPE: DNA
<213> ORGANISM: homo sapiens

<400> SEQUENCE: 21
tgatctcatt tatccctccc agcagactct gaagcagaaa ccctttatca gcatagtaca     60
gattagaaaa cttaggctta gactggtagt aacagttaga tatgggatcc aggggctgga   120
atttgcctcc caacttgccc acctgtgtac agtggggaga acaggtgtga cttgatgtcc   180
tctctctctg caggtcttct cagtacagca tggtggctgg ggcaggccga gagaatggca   240
tggagacgcc gatgcacgag aacccggagt gggagaaggc ccgtcaggcc ctggccagca   300
tcagcaagtc aggagctgcc ggcggctctg ccaagtccag cagcaatggg cctgtggcca   360
gtgcacaggt gagaaggcct catggggctg ggtaccctg agccagaggt tgtgggaggg    420
acacagtctg gcgtcctgtt gtatcattca gacggggtgc tctgagggga aacataaaaa   480
gacgttccag ggtatctaaa                                                500

<210> SEQ ID NO 22
<211> LENGTH: 500
<212> TYPE: DNA
<213> ORGANISM: homo sapiens

<400> SEQUENCE: 22
gaaaaccgag tcctctcagt tgcacacgtg tacgtatcag tgggaagtgc ttgccattac     60
tccaaagcct agaaccttca cgtcatgaag gttctggaag gttttttcaga ttgcttaaga   120 tacgcagcca ttccatattc atctccaact acacagggga acggagcaga tagagctgcg   180
actgggaagc gtcaccttcc cgtccagagc gctttctttc agaccctgcc tacctgcagg   240
cagatggacc ggagggtttt ctgcttcctt tcaaccagat aacttcctaa gtggagatgg   300
cctgtaggta gcaaatgcag gattttgttt actttcatca tgtcatgtgg tggtcagact   360
gctcgctggt ggcctcgctt tagaaggttt tcatcaagcc ccgcccttc tctctcatag    420 tcttaatgcg tctggaccac tggggaaaat attttctttt tcaaaaagca gccccttcag   480
tctgcgttcc cagttcattt                                                500

<210> SEQ ID NO 23
<211> LENGTH: 500
<212> TYPE: DNA
<213> ORGANISM: homo sapiens

<400> SEQUENCE: 23
gcaccaggtc actcacttat gtgggaagca ggtggagggc agatggtctg gatacctggg     60
cgcagggatg ggagtggcca ggagtgctga cctctcatct ggctgcccag ggcaaacaga   120
gagccgtggt cggctgcagg gggtggcaga actgcgtctg gcaggtttgg agctgacaga   180
tgcctccctg cgtctcctgc tgcgtcacgc accccagctg agcgccctgg acctgagcca   240
ctgcgcccac gtcggggacc ccagtgttca cctcctcacg gcccccacgt ccccactccg   300
cgagaccctg gtgcacctca atcttgctgg taagcacggt cccccatccg tcctgccagc   360
ctgtggatcc ccacggccag tgccaaccc ttgctcacct gcctggtctc agctccactg    420
```

```
ccccatcccc aggttgccac cgcctaacgg accactgcct cccgctgttc cgccgctgcc    480
ctcgtctacg ccgcctagac                                                500

<210> SEQ ID NO 24
<211> LENGTH: 500
<212> TYPE: DNA
<213> ORGANISM: homo sapiens

<400> SEQUENCE: 24
acccacagca gcagttgcgt gatgacgacg tgggcgagct cggccgccag gtggagtggg     60
gagcgcagct gtgggtcctc tacgctggtg tcgagcggcc cgtgtcgcgc atgggccaaa    120
agcaggagaa cggtagccac gtcctgggcc tgcacggcgg cccacagctg gcggcccagc    180
ggctcctccg aggtgctcag cggcgccagg aacagtagct gctcgtactt ggcgcgaatc    240
cacgactcgc gctcctccct gcaagaccag ggatcaacgg aaaaggctct agggacccc     300 agccaggact tctgccccta cccacgggac cgtctcaggt tcgcacaccc tcagcaaccc    360 tcccccgct ctgttccctc acgcttaccg cgaagagtcc cgcgagggct tggcacggcc     420
tcgcgtgtcg ctttcccaca cgcggttggc cgtgtcgttg ccaatagccg tcagcaccag    480
ggtcagctcc cgtggccagt                                                500

<210> SEQ ID NO 25
<211> LENGTH: 500
<212> TYPE: DNA
<213> ORGANISM: homo sapiens

<400> SEQUENCE: 25
cctgacaggg gcctggtccg gtatggggtg ctgggggcca ggcctggagt cccagggagc     60
ccagctcagt tgagagaaag gttcagcctc tgccatactc ctcttaggtc tcacctcttc    120
cctggggcca atgtggggcc ctccttagct ccacaggccc agacattcta gccccgaccg    180
cctgtggccc ccatcccaag aacccggggg gctccgagcc ttaccattgg tccgcaggcc    240
cctccgtgcc gggcacccac ctccagctct ggctgtgtcg agcgagaagt gagctcagtg    300
ctcgtctgca gtgaagggtg gcccaggctt ccgcttcctg cccacatacc ccacctgccc    360
ctccctgctg caggacccct ggtccacacc agaccctccc cagtctctct ggaggaggct    420
gggctgccgg gcctgtcctc caaggaagaa gcagcaccaa cttgaagctg gatgcagcct    480
tgcatgtgtt ctcaggtctt                                                500

<210> SEQ ID NO 26
<211> LENGTH: 500
<212> TYPE: DNA
<213> ORGANISM: homo sapiens

<400> SEQUENCE: 26
gcagcagccc tggggaaacg gctcagcctc gagctccttc tgagctaggg acgcggcagg     60
agcggctgtc agaaatgggc ccaggtggcc tccaggagcc ggcccgatcc acgatcagtt    120
ccatcccttc ttcactggca catctctgag gcagctcctg gggaagtgca gggcccccgc    180
gagggctcgc aggaagagca cggagacgac caaacaggcg ctaccaagta tgggttccag    240 accccacc ggccattcca gacgcctccc tgtgctgcgc acacagcctc cccgcacccg      300
ctctgcagct cagagctgct caccctcagc tctgggtcct ccgcacccac ttcggattcc    360
catcagagga caggccctgc ctgtgggccc atcaccatcc catctcccac ctagacggaa    420
aacccgagct ctgctcctcc tgaaatgagg ccagccctct ggtgtcaatt acatgcaact    480
```

```
tccccgggcc tcggcttctt                                                500
```

<210> SEQ ID NO 27
<211> LENGTH: 500
<212> TYPE: DNA
<213> ORGANISM: homo sapiens

<400> SEQUENCE: 27

```
tggggcttgg ctgtggcctg aatagcgca gacatctgca agttggaacc catcgagtgg    60
gggagagtgg gcccagctgc aacgctgaac tctcgtcttt taggcttgtg aatcacggct   120
ttattcctca ttctggcttc atcaaatggt tcatctcagg gaaaagggac ctcaacatgg   180
cttttctttt ccttcggacg gtttcgtgtt gccaactctg ctgcacatag tacaggaacg   240
gaatccaggc gcgcacacct ggctttacca gaacgcacgt tctgttcatc aagtgagagg   300
ctggcacatc agcgaggctt tggtttgatg ttttgaatt agaattgatg acagaaaaat    360
actatgtgca tcacatctta ttaaggaaga tgaatgagga tctttgaaac ccacacggaa   420
ccaagcttgg gagtcaacct ctgctggaag gaaggaagtg attccttctt aagaatgaac   480
acataaacag aaacctgggt                                                500
```

<210> SEQ ID NO 28
<211> LENGTH: 500
<212> TYPE: DNA
<213> ORGANISM: homo sapiens

<400> SEQUENCE: 28

```
cagcaagaga aggagcagga gaggctggaa tattctggct tgaaaacagc agctgtgtaa    60
taaagccggg ctggttttgtc tcagggcccc gctgtcccctt ctccccgcct caaagtagca  120
gcatgaatca gttcactgcg gcaatggtcc aggcgatgtg acttgcatcc ccatcagcta   180
cctgattgcg gtccctggat gcatgaggcg ctggatgtgc ctggcatacc aaactgcccg   240
cctctgtgcc gcagctactg gtaatgaaga tcaccggccc cgcccagcac tgcggacaga   300
gccgggcatt cttcaaggcc accactggtc ttttatcttg tccaaggctc tgggatagtc   360
accgaaatcc ttgggctgct tttgacgggg gccaccagcc tgtctcaaag atgccctgac   420
aagcccctcc agccctgggc agacaaaggc ttgaaaggag aggaattgca cacggtccag   480
acgctgctgt ttctaatacg                                                500
```

<210> SEQ ID NO 29
<211> LENGTH: 500
<212> TYPE: DNA
<213> ORGANISM: homo sapiens

<400> SEQUENCE: 29

```
aatcctgtta ggaaaaatga agtctacttt aggaggtgag agaaggacag gaaaaaaaaa    60
caaaggaagc ttggatgtca acagtcctct ctgccgccca cgtcctctct gtctctgcag   120
ctgtgtgcct ccatggcagt gaccagcaaa agcgcaaggg tgccgcagcc acggcgaaaa   180
gaaagtccaa gggtggaggg gtgaacgtgg agggacgtct gtgcacctgg cccctgaag    240
acccacgtgc gtctgggggc acattgcggg ggaaggaacg tgatcttcac acagaaaggg   300
acagttttaa ccgttttctg ttttcatgtt ctcatttaac tgttggccgg aaattgccgg   360
taggctgccg tggcctgacc ctactacgtg cacaactccg caggcattag gggaggggtc   420
atctgctcta attaggtaac aggggcaagt gggattaaag ttttaaggca gttatattaa   480
```

```
gaagctgagg acaggattcc                                                 500
```

<210> SEQ ID NO 30
<211> LENGTH: 500
<212> TYPE: DNA
<213> ORGANISM: homo sapiens

<400> SEQUENCE: 30

```
ggcctaggga tcctgtgccc tgggacccat gaccaagcca gggggtggag ggattggggg     60
ttgcctgaaa ttgtccttat tttattcagg ctggggtggg gtggagtccc aggcacaggg    120
accttgtttt gagaagtggc tgtgcctggg actccgccca aggattgggg ggatgctgtg    180
cccagggtgc ctctgagacc tggggcagg ctgtgcttgg agtccccta ggccttggcg      240 tggtgggaac gctgtaccca gtgacccat cctcgagacc gtacctaggc agttgttgtg     300
ctgagacccc cttaggcagg gagaggtagg gattgtgtct ggaatcgcgt cctggaggcc    360
ttggtttgat acggggggctg tgtccccgac cccatctcca tccccatcta gttctaggag   420
ttgtacctag aatctctgta cccctgtcct tggttttgtg gggggtctgt gtccaggatc    480
cctatttcca gggccttggc                                                500
```

<210> SEQ ID NO 31
<211> LENGTH: 500
<212> TYPE: DNA
<213> ORGANISM: homo sapiens

<400> SEQUENCE: 31

```
acattccctc agaaggaaa aaaagaagg aaatgatac ctaggaaaac atgcaagcct        60
gtttcattta tttgtatcct aagcagcagt gtcatagaac agacagtttg tttcagccaa   120
ccagactgga gcagctgcga gtgctacatc ttggctgtct gaagcgattg gctcctctct   180
ggggagtgga gggtgttcag ttattaatga ccgctgagca ggcagcacca tgtcagtgtg   240
acaactgatc gggtgaacga tgcaccacta accaccatgg aaacaaggaa aaataaagcc   300
agctcacagg atctctcttc actggattga gagcctcagc ctgccgactg agaaaaagag   360
ttccaggaaa aagaaggaat cccggctgca gcctcctgcc ttcctttata ttttaaaata   420
gagagataag attgcgtgca tgtgtgcata tctatagtat atattttgta cactttgtta   480
cacagacaca caaatgcacc                                                500
```

<210> SEQ ID NO 32
<211> LENGTH: 500
<212> TYPE: DNA
<213> ORGANISM: homo sapiens

<400> SEQUENCE: 32

```
ggctccgtgt ttctaagaac cacagcccag catcattaaa gaaggcatta ttttgtgttt    60
agtagagcac taaattggtg aaatatagtt gtgattctgg tagtgaatat ccctgttgcc   120
acggtaacga tattatgtca tgggaggctg tctcgagtgc tcctgggagc agccaggtct   180
ccgtgagctc ctgtttactc taaagactcc ggcagcccac atgtgtgcac gctgaataaa   240
atcgtgctgc gggaccacag tgcggggagg caccgactct gtcattctgt caacgcaccg   300
cacagtcacg aacatcagca ttgacatgaa atggacggtt agggagctgc aaaggactca   360
tgctcctcta ttgcacgaat ttgtcttttc atattcaaag tacttgtaag agctccaagt   420
tccacgtact cagccactaa cctcaggcat ctgcacggga gacttggtac acaggctcac   480
atgcatgcac gcacacaggc                                                500
```

<210> SEQ ID NO 33
<211> LENGTH: 500
<212> TYPE: DNA
<213> ORGANISM: homo sapiens

<400> SEQUENCE: 33

```
gcaggacggc atccgcagca agcccgccgc cgatgtcaac gtgcccacgt gctcgctgtg    60
tgggaagact ttctcttgca tgtacaccct caagcgccac gagaggactc actcggggga   120
gaagccctac acatgcaccc agtgcggcaa gagcttccag tactcgcaca acctgagccg   180
ccatgccgtg gtgcacaccc gcgagaagcc gcacgcctgc aagtggtgcg agcgcaggtt   240
cacgcagtcc ggggacctgt acagacacat tcgcaagttc cactgtgagt tggtgaactc   300
cttgtcggtc aaaagcgaag cactgagctt gcctactgtc agagactgga ccttagaaga   360
tagctctcaa gaactttgga ataattttta tatatatata aataatatat atatatatac   420
atatatataa atagatctct atatagttgt ggtacggtct aaaagcagtc ttgtttcctg   480
gaaataaaaa gttgggatat                                               500
```

<210> SEQ ID NO 34
<211> LENGTH: 500
<212> TYPE: DNA
<213> ORGANISM: homo sapiens

<400> SEQUENCE: 34

```
gtatgcgggc cagacagtgc ggtaaagcca agggagatta tccagacccc caggagcgaa    60
cagcaagcag caaccgaagg cgcaagtgcc aggattacag cctaggctgc tccaactatg   120
agcccttcct cggaccctgg gactcggcta cttggggttt gggggtcttc acaccacag    180
aggcacaaag ctgactttaa tcactttttt tcctttaaac ttgattctgc cgcagtggag   240
ccagcacagc ggatgttttc acacccagca agacaaaggc cgtcgtctcc gccatgacac   300
tgttccgttc caagcagagg ccgggattct ggactcctcg aaaaatcaaa agaaacaag    360
gaaaacaaac aacaaataca gcaacaaaca gaaaaaactg aaaaccacca aaatcgtttg   420
cccgtttgcc cgtgccaggg gtgatctggg catctgttgc agcagaaggc gcttgtgtgg   480
ggctaatttt tcttttggtg                                               500
```

<210> SEQ ID NO 35
<211> LENGTH: 500
<212> TYPE: DNA
<213> ORGANISM: homo sapiens

<400> SEQUENCE: 35

```
cccttttttcc ctgcagacat ccagtccctc cctctcatgt cccagtcctt ctggagtctt    60
cggctcaatg agggaaagaa tggccttttc ttcccatttta tacagagcga caagcatcct   120
ctctcaggaa gagccctccc atctggggca ttaatcctcc ttttttttctt ttctcagtgc   180
cagaactgaa agagcagatt caggcgtgga tgagagagaa acagaacagc gatcactaaa   240
ccgttccgcc gcccaccctc tgctagacac agccaaggcc aacgaggcaa gcagaagcag   300
cggccgcagc gaagctgccg ttcatgtgtt ggaggccaaa tgtggcaaac caccccagg    360
cccacccaga gcgagcaaac gctgagacct gaaaggacat ggatgagaag aggagcccgc   420
ttcctgtaca tatatttaag tgacaaacac ggtcaaaagc ttaagggaca ggttttatgg   480
ttgcttgtgt aataaagcat                                               500
```

<210> SEQ ID NO 36
<211> LENGTH: 500
<212> TYPE: DNA
<213> ORGANISM: homo sapiens

<400> SEQUENCE: 36

| | | |
|---|---|---|
| tgacaaatgg gagtgatgaa agagagggac cctgcacaaa gcactgctgt gtgccagaga | 60 |
| tgctggccaa gtcctggacg gtctcagctg agcaagatcc ctgccactac catcccccag | 120 |
| ccctgggacc catgccgtct cttggggagc cttgctcttg cccagatggg gaagaatcct | 180 |
| attcactgtc ttgaagggcc cagcagccag gacagggcag cgccggccat gtcatgagca | 240 |
| gcccaaagcc gcactcgggt caggaggctg atgctctcgg gacttgagcc tccgcacagc | 300 |
| ccaggtctgg ccatttctgc tgcatctcaa tggcttcctg agacgtggaa acccaggaaa | 360 |
| gggggagggc agggcaagta agctaggtca ggatggcccc tggtgttcct ctccaagtcc | 420 |
| tcagggagg aaaaaccagc ccgaccagaa ccagggcaga tggtgtgggt ggggagggac | 480 |
| agctgagtcc tgcaaggaat | 500 |

<210> SEQ ID NO 37
<211> LENGTH: 500
<212> TYPE: DNA
<213> ORGANISM: homo sapiens

<400> SEQUENCE: 37

| | | |
|---|---|---|
| tgtggttgta tcaatccaca aatatttact cttaacagac ttgtatctgt ggagatttcg | 60 |
| aacaaagaca gtttaggggg attacaaaaa ccctaaaccc cgttttctc ccggacttgg | 120 |
| tgctttaaat gccaattata ggcgagccat atccaacagc aacggggaaa ggcgagcagg | 180 |
| ctccggggag ggaggtgggg ggagagtccg gccattaaat gtaacttttc attatgaaaa | 240 |
| ggatttcgcc ggttttatct tctaataaga ttatgtcacg aacacaagta cctaggatgg | 300 |
| tgctgagtga cagggctctg tcgtttaatc agaggctgtg ccgctcaaac cgcggggccc | 360 |
| tttgtcccac ggagtgaacg acggaaactt gccatcctaa tccccttatt catgtcaagc | 420 |
| acagaaaaga agccgagcac cttacaaccg tgtcccctcc accccttccg aggacggcgg | 480 |
| gaagagggggg ctccggccct | 500 |

<210> SEQ ID NO 38
<211> LENGTH: 500
<212> TYPE: DNA
<213> ORGANISM: homo sapiens

<400> SEQUENCE: 38

| | | |
|---|---|---|
| tttacttgga gaaggcgggc aaaaacgagg aggtcaatgg gtgttggcag cggtaccagg | 60 |
| gacagtgagg ggggctttcc tgggctcagg cctcgccggc cgcctcaggg tgcttctgcc | 120 |
| gcaggtgttt gtccagggtg gctcgcaggc cgaaggcac atggcagtgg ggcactcga | 180 |
| agcgggtgct gccaggcgtc atgccgtgca tgcggcggtg gcggttgagc ttactgctct | 240 |
| gggcgcaggc gtagttgcag aactcacagg tgtaggggcg ctccccggtg tgtgagcgcc | 300 |
| ggtgcaccgt caggttgctg ctgttggtaa aatgcttccc gcagaactca cagctgcccc | 360 |
| cgggcccgcg gctcttgccc cctgacttgg gcatcttttt gggtgatgcc ttctggctgt | 420 |
| ttgcagggtc agttctttgt tccgtggtga tggctcccca agtgtctcca ccagggccgg | 480 |
| cttgagcccc actgccagga | 500 |

<210> SEQ ID NO 39
<211> LENGTH: 500
<212> TYPE: DNA
<213> ORGANISM: homo sapiens

<400> SEQUENCE: 39

| | | | | | | |
|---|---|---|---|---|---|---|
| gggcctcgga | aagaaagacc | tgaatggtgt | ggaggaaaga | gccctgagct | gggagacaag | 60 |
| gtccctccag | ctactgctcc | aaccctgact | tgctgtgtgc | ctttgatcaa | gctgtctctg | 120 |
| ggctttagcc | tcccccttg | taaaacgggc | ggggaagagg | ttgagatggc | atgggtgcct | 180 |
| ccagctctct | cagcatgatt | ctgagaactc | tgcgggtagc | tctggcctgc | cccttcctcac | 240 |
| gccctaccgc | gatgtgcgca | caacagtatt | gtgacccttg | tggtgtactg | tagatttac | 300 |
| ctagttttgt | ttcccgtcaa | acacataaag | aaaagtaat | cttcccacc | ccgccccac | 360 |
| taaaataata | atcatgagaa | tgaatacaca | gggaggaaga | ctggaaaaaa | tgaaagggaa | 420 |
| ggacttgctc | cctcaaaagg | aaggatctca | gtttgaagta | atgtagtggc | tgttgcacag | 480 |
| ggttagacgt | atctcgccga | | | | | 500 |

<210> SEQ ID NO 40
<211> LENGTH: 500
<212> TYPE: DNA
<213> ORGANISM: homo sapiens

<400> SEQUENCE: 40

| | | | | | | |
|---|---|---|---|---|---|---|
| tcggcgagat | acgtctaacc | ctgtgcaaca | gccactacat | tacttcaaac | tgagatcctt | 60 |
| ccttttgagg | gagcaagtcc | ttcccttttca | tttttttccag | tcttcctccc | tgtgtattca | 120 |
| ttctcatgat | tattattta | gtgggggcgg | ggtgggaaag | attactttt | ctttatgtgt | 180 |
| ttgacgggaa | acaaaactag | gtaaaatcta | cagtacacca | caagggtcac | aatactgttg | 240 |
| tgcgcacatc | gcggtagggc | gtggaaaggg | gcaggccaga | gctaccgca | gagttctcag | 300 |
| aatcatgctg | agagagctgg | aggcacccat | gccatctcaa | cctcttcccc | gcccgttta | 360 |
| caaaggggga | ggctaaagcc | cagagacagc | ttgatcaaag | gcacacagca | agtcagggtt | 420 |
| ggagcagtag | ctggagggac | cttgtctccc | agctcagggc | tctttcctcc | acaccattca | 480 |
| ggtctttctt | tccgaggccc | | | | | 500 |

<210> SEQ ID NO 41
<211> LENGTH: 500
<212> TYPE: DNA
<213> ORGANISM: homo sapiens

<400> SEQUENCE: 41

| | | | | | | |
|---|---|---|---|---|---|---|
| gttaagaaac | caacaggaaa | aagaacgcac | aactcccagc | acagtgctgg | cgcctgtgag | 60 |
| gcactcagcc | gacgggagct | tgttcttcg | ttgtattgtg | gcggggaagc | aacatggggc | 120 |
| cttgtcctgc | ggacacactt | gagttaagat | cacactgggg | ctccttcagg | ccctgggcca | 180 |
| agttggggca | caggccgagt | tcggttgttg | ctgtagcctc | agaaccaccc | agagttgact | 240 |
| gaagacactc | gggggcctcc | ataactgaga | gcaggcagag | gcattgtttt | taacccagtg | 300 |
| tggacccca | aatggaacat | tttccttccc | taggtgaacg | ccttcggaac | cctccgaaaa | 360 |
| tcgcagtttc | acttttagca | aagagccccg | ctgcagcagg | ggaaagcccc | cacaaacccc | 420 |
| gtcctctcca | aagggaatgt | tccgagcccc | ctgcttcctc | cacccttctc | ttccccctgg | 480 |
| ttaattcctt | cgctccagct | | | | | 500 |

<210> SEQ ID NO 42

```
<211> LENGTH: 500
<212> TYPE: DNA
<213> ORGANISM: homo sapiens

<400> SEQUENCE: 42
agctggagcg aaggaattaa ccagggggaa gagaagggtg gaggaagcag ggggctcgga        60 acattcccctt tggagaggac gggggtttgtg ggggctttcc cctgctgcag cggggctctt    120
tgctaaaagt gaaactgcga ttttcggagg gttccgaagg cgttcaccta ggaaggaaa       180 atgttccatt tgggggtcca cactgggtta aaaacaatgc ctctgcctgc tctcagttat     240
ggaggccccc gagtgtcttc agtcaactct ggtggttct gaggctacag caacaaccga      300
actcggcctg tgccccaact tggcccaggg cctgaaggag ccccagtgtg atcttaactc     360
aagtgtgtcc gcaggacaag gccccatgtt gcttccccgc cacaatacaa cgaagaacaa     420
agctcccgtc ggctgagtgc ctcacaggcg ccagcactgt gctgggagtt gtgcgttctt     480
tttcctgttg gtttcttaac                                                 500

<210> SEQ ID NO 43
<211> LENGTH: 500
<212> TYPE: DNA
<213> ORGANISM: homo sapiens

<400> SEQUENCE: 43
ggggcactgc acctcggccc ctctgctcat cttgggcagg tgacccaggt ggagctcagg      60
cccgaggtct gtgctgggcc gtgggtcccc ttttgaccgc ccccccggct ccggacccca    120
agcccctcct cgctgactgt tcctcggtcc cacccgcagg ccccccaaag atggcggaca    180
aggtggtccc acggcaggtg gccggctgg gccgcactgt gcggctgcag tgcccagtgg     240
agggggaccc gccgccgctg accatgtgga ccaaggatgg ccgcaccatc cacagcggct    300
ggagccgctt ccgcgtgctg ccgcaggggc tgaaggtgaa gcaggtggag cgggaggatg    360
ccggcgtgta cgtgtgcaag gccaccaacg gcttcggcag cctgagcgtc aactacaccc    420
tcgtcgtgct gggttagtcg ctgctgcggt cagaggtcat gggctgggtt ggagccaggc    480
aggggtgtgc aggagggcgg                                                500

<210> SEQ ID NO 44
<211> LENGTH: 500
<212> TYPE: DNA
<213> ORGANISM: homo sapiens

<400> SEQUENCE: 44
tccattagcg atcgctttaa tgacaatacc cccgagttgg ggtttaaact aaagaaatcc      60
agttcatttc cagcttcaat ctgatactgt accaactgaa gttcatctgc atcaatagca    120
gaaacagtgg ttatttgctc tcccacgcct agatctctgg gaattgtccc ttcacaattt    180
attttctcaa acaaaggtgt gttgtcattc aagttattga gagtaattgt agcaaggact    240
tcgacttccc ggcggtacgg caagccccag tctgatgcac gaatcctcag agtataaacc    300
cgaggcatca gttcgtagtc caggtttttct gacgtactca cggcaccagt gaaatggtca    360
atcgcaaacg gcacatgatt taaatttgcg atactgtatg tcacgtaccc gttctcaccc    420
tcatcagggt ctacggcact caggctcatg acagtagtac caatgggcac gttctcatca    480
aaagcagctt tgtacgctgt                                                500

<210> SEQ ID NO 45
<211> LENGTH: 500
```

<212> TYPE: DNA
<213> ORGANISM: homo sapiens

<400> SEQUENCE: 45

```
caaggggacg cccctgggct ccaggtcctt tgcaggcctt agaggccctg cacatcaact    60
gttctctgga gaaccttct gcaagcctct gggatgtagc tgcctcctct gctgagacac    120
tagccacgcc tcgtctcctt ccaggctgct gagccagtag cgttgaaccc tctcacctgc    180
cgtccccgcc tttcctatgc cctttgtcct tgtaggttga cgcctgtgtc agcagagaga    240
ggaaagagac gcaggcgatc attctcccgt ccttacgtgg cagacagggt tatttgcgta    300
gattgaccga gatgagtgtc ctgcactctg aagaaccttg gtggctcctc cttcggaatt    360
gatttaagca gtggtagcat agtgttttga agacagtcaa cggtgggttg ggtttactgg    420
aattgcccaa ggtgtttgga tgaaggcctt cattaagcaa ggcccttggc gggacgttct    480
atggaaccag ccctgaatgg                                                500
```

<210> SEQ ID NO 46
<211> LENGTH: 500
<212> TYPE: DNA
<213> ORGANISM: homo sapiens

<400> SEQUENCE: 46

```
cacttttgtg ggagaccaat gggtgcatga agccaaggga aagtgcattt gcggaactcc    60
aagggtgtgt ggtcttgtgc acaatcaagg gagtaagtgt tcctaaaggt gtgacttgtg    120
tgaccatcca aaggctgccg gggcgggggg atcccagaga gcacaacatg gcaatcacga    180
aaatatgttg gtgtcatttc tcggtcttca aaaatgacgg acactgctgg tcgctgtggc    240
ttcctcctac gcgttcggtc actcctgcac atgtccgcag tagtggtgct ctcggggacc    300
ccctcgccac cccacaatac cgctcaccac atggccaaac aggttcgtct ttttccatgt    360
gatttcttct tttgctagaa catttataaa acttcttagg aaatttaagg aatgttaagg    420
aagttaagga aaagttatga acgcttttcc agaggctaaa aaagaattca atttatttcc    480
tactagctag tctagaattt                                                500
```

<210> SEQ ID NO 47
<211> LENGTH: 500
<212> TYPE: DNA
<213> ORGANISM: homo sapiens

<400> SEQUENCE: 47

```
cacttttgtg ggagaccaat gggtgcatga agccaaggga aagtgcattt gcggaactcc    60
aagggtgtgt ggtcttgtgc acaatcaagg gagtaagtgt tcctaaaggt gtgacttgtg    120
tgaccatcca aaggctgccg gggcgggggg atcccagaga gcacaacatg gcaatcacga    180
aaatatgttg gtgtcatttc tcggtcttca aaaatgacgg acactgctgg tcgctgtggc    240
ttcctcctac gcgttcggtc actcctgcac atgtccgcag tagtggtgct ctcggggacc    300
ccctcgccac cccacaatac cgctcaccac atggccaaac aggttcgtct ttttccatgt    360
gatttcttct tttgctagaa catttataaa acttcttagg aaatttaagg aatgttaagg    420
aagttaagga aaagttatga acgcttttcc agaggctaaa aaagaattca atttatttcc    480
tactagctag tctagaattt                                                500
```

<210> SEQ ID NO 48
<211> LENGTH: 500
<212> TYPE: DNA

<213> ORGANISM: homo sapiens

<400> SEQUENCE: 48

| | | | | | |
|---|---|---|---|---|---|
| ggcttttcag | gctttcaaac | ctgctcctcc | aaatcggttc | ttccatcaca | taacaattta | 60 |
| atgtgccttc | agaaggtgga | gaagctcatg | gaagccatta | cgaaaatgag | gagaaacaca | 120 |
| gattttatga | gtgtaataaa | aatacaatga | tctagaccat | aaactaatca | tccggcactc | 180 |
| ggctccgtgc | cacccaagtg | tgacattaca | gagcccgtc | gactgggggg | acccggacgg | 240 |
| cctggaagcc | gcactcattg | gctctcgcgt | ccgcccttca | ttatggggcg | ccttccggc | 300 |
| tctctgaaga | tttggttaag | attaaatcca | aatgaaactt | aatttaaaca | agcaatccca | 360 |
| aaggcgctct | ggggaataat | atttcttttt | aggtcactgt | gtataaaagc | agagagggga | 420 |
| atttactaaa | tcaaacaaat | aggcagccca | attgggtacc | aatattacaa | gctgttcatg | 480 |
| gaactgatta | cattatcttg | | | | | 500 |

<210> SEQ ID NO 49
<211> LENGTH: 500
<212> TYPE: DNA
<213> ORGANISM: homo sapiens

<400> SEQUENCE: 49

| | | | | | |
|---|---|---|---|---|---|
| agtctctgga | gccctaggt | gcatcccagc | ccctcccacc | tctcctctat | ccaagaaggg | 60 |
| caccaggttc | tttactttgc | tttattgttt | gtggggtgaa | gataaggcct | tgggcttgag | 120 |
| aaactcattg | tcataaagtt | ataaactggg | aaactgggtc | agaaggcata | gaaacaactg | 180 |
| tcatcgccca | tcctcccttt | ctgtggatga | ggcgggacaa | ggccggcccc | ctggctgggg | 240 |
| cctgggacgc | gagggctctc | agagcttgga | gaaggtgacg | gttttcagtt | ccttgttctc | 300 |
| agtcgtggcc | tggaccgact | tcacgaggtc | ttgggtctgc | agcatgctca | tgttccagga | 360 |
| cgcctggtac | cgagggtgtt | gagagagaac | gaggagagag | attagcaggg | gccaatcagg | 420 |
| ataaagcatg | agagcaccct | gcaccctggt | tggtcgcctg | ggttagagg | agggctgtga | 480 |
| ttggtcggag | cgtgcacctt | | | | | 500 |

<210> SEQ ID NO 50
<211> LENGTH: 500
<212> TYPE: DNA
<213> ORGANISM: homo sapiens

<400> SEQUENCE: 50

| | | | | | |
|---|---|---|---|---|---|
| agtctctgga | gccctaggt | gcatcccagc | ccctcccacc | tctcctctat | ccaagaaggg | 60 |
| caccaggttc | tttactttgc | tttattgttt | gtggggtgaa | gataaggcct | tgggcttgag | 120 |
| aaactcattg | tcataaagtt | ataaactggg | aaactgggtc | agaaggcata | gaaacaactg | 180 |
| tcatcgccca | tcctcccttt | ctgtggatga | ggcgggacaa | ggccggcccc | ctggctgggg | 240 |
| cctgggacgc | gagggctctc | agagcttgga | gaaggtgacg | gttttcagtt | ccttgttctc | 300 |
| agtcgtggcc | tggaccgact | tcacgaggtc | ttgggtctgc | agcatgctca | tgttccagga | 360 |
| cgcctggtac | cgagggtgtt | gagagagaac | gaggagagag | attagcaggg | gccaatcagg | 420 |
| ataaagcatg | agagcaccct | gcaccctggt | tggtcgcctg | ggttagagg | agggctgtga | 480 |
| ttggtcggag | cgtgcacctt | | | | | 500 |

<210> SEQ ID NO 51
<211> LENGTH: 500
<212> TYPE: DNA
<213> ORGANISM: homo sapiens

<400> SEQUENCE: 51

```
tgctcgtagc cacaaacgct gggccctgcg gggcaggtcc acgggacaga cagacatacc      60
aatactctgc tgctcggact caaccctgtg tcccagagga ctgaagtggc aggagcaaca     120
cagaaggggg ccggggtggg ggggcactcc ctaaaaacct ggcacggaga cacccaggga     180
aggacgcgag gggagcaggg agcgcgggag cctcatgcag gtgtgcgttt cacacggggg     240
ggccaaggtc gcccttcccg aggcagccct gccttctccc ccggccctcg cacccagcg      300
cgagtggagg gcatgcggtg cgcagggcag ctgtggaggg cagagacagc caagacctcc     360
cctgcgaggc aggcccgtgg gcacagtttt aggacacagc ctggtccgtt ctgacagcca     420
caggcattta gtctggagac tgcccaggca tcccacgatg ggtcagaggc ccactttacc     480
caaaaaagcc tacctgcctc                                                 500
```

<210> SEQ ID NO 52
<211> LENGTH: 500
<212> TYPE: DNA
<213> ORGANISM: homo sapiens

<400> SEQUENCE: 52

```
catcctctcc ctccacatcc tggcacaggc ctgcctcccc ctgccccagc ccagggccag      60
gccacactct gcctccaaag ccaccgtccc cccgaggcac cactgcatcc ccaaggggc      120
gggttcggag gaaggaggag gcaaaggaga gccccagcgc cgcagggccc gaggacaaga     180
gccagagcaa gcgcagggcc agtaacgaga aggagtcagc agcccagcc tcaccggcac      240
cttcgccggc gccctcgccc accccagccc cgccccagaa ggagcagccc ccgcggaga      300
cccctacagg taggaatgaa gagagggag gggtgggccg agcgagagaa gccagcttct     360
cctgtgtggg ggtgtgggcc gccagagatg cctgaggact gggagtggga catggaaaga     420
ggagactcct gccctcagca gtcccaggcc cagaacacag gccgctggga gatgacggcg     480
gtgtctgcgt gggtgtgctg                                                 500
```

<210> SEQ ID NO 53
<211> LENGTH: 500
<212> TYPE: DNA
<213> ORGANISM: homo sapiens

<400> SEQUENCE: 53

```
aggagaccca catattattg caccctttggg attccccttc ctaattcgga ggcaatcacc     60
attattcaca ttttatgaaa taagaagcac aagctcagag ggggttcaga gaagtttaaa    120
catgtacaca gtggttaaat ggttaggtta agatgaccat tgaacattta agtttaatga    180
tttataaaac catatagaca gcgtgggcat gtgatctgtg agccgtggtc cccacggaag    240
cggtgagaac gcacctggcc ggctcagcca cacggcacgg tggcctaggc cctgctgcgg    300
gctctggatc cagcggtcac ggtttcactg agagggcgcc tcccaggggc tgctccggcc    360
cagggcaggg cattgcaggg gtgatgggac agccctgctt ttgagaggcg cggcactctg    420
ccaagggcca cccctggtag ccctgcccag cctccctggg agcacacagc tgtctaggat    480
gcttctgggc atccttcccc                                                500
```

<210> SEQ ID NO 54
<211> LENGTH: 500
<212> TYPE: DNA
<213> ORGANISM: homo sapiens

<400> SEQUENCE: 54

```
ccatccagcc ccatataaac gtcaggggtg actgttatca ctagtaatat cactgtcatc    60
tcctacgaaa cttacataag aggtagaagt aaaacacggc tagtggaaaa ccagcctacg   120
tgccagcagc tttgagagtt gaggggattc tgaaacaagg aatgggaata tgtgtccagt   180
ttcttacccg gtgttcggcc aggaactcgg gtgtcagcgt ccagggcgca ttcctcacca   240
cctcatccac gtagcggcag tgctggactg cgtcatagcg ctcattctcg ttcatcaccg   300
tgaagccttt gaagttgtgt gtgagctcat cactgcaaac tggttcacca catcataaat   360
tgtgtgttgg agtcctcttt gcttagcacc tcctcagcca ccgacctctc ccatcttctc   420
ccactgctta ggactgcaac catcttcccc aactggaaaa aagtcttcta aaggtggttg   480
aacctgggtg ataacgcttt                                               500
```

<210> SEQ ID NO 55
<211> LENGTH: 500
<212> TYPE: DNA
<213> ORGANISM: homo sapiens

<400> SEQUENCE: 55

```
aaagcgttat cacccaggtt caaccacctt tagaagactt ttttccagtt ggggaagatg    60
gttgcagtcc taagcagtgg gagaagatgg gagaggtcgg tggctgagga ggtgctaagc   120
aaagaggact ccaacacaca atttatgatg tggtgaacca gtttgcagtg atgagctcac   180
acacaacttc aaaggcttca cggtgatgaa cgagaatgag cgctatgacg cagtccagca   240
ctgccgctac gtggatgagg tggtgaggaa tgcgccctgg acgctgacac ccgagttcct   300
ggccgaacac cgggtaagaa actggacaca tattcccatt ccttgtttca gaatcccctc   360
aactctcaaa gctgctggca cgtaggctgg ttttccacta gccgtgtttt acttctacct   420
cttatgtaag tttcgtagga gatgacagtg atattactag tgataacagt caccccctgac  480
gtttatatgg ggctggatgg                                               500
```

<210> SEQ ID NO 56
<211> LENGTH: 500
<212> TYPE: DNA
<213> ORGANISM: homo sapiens

<400> SEQUENCE: 56

```
gcacttacgt gctgggggct caatacacgt tcctggaagg aacagaggga aggaggagct    60
tttcatttct ctgctatctt gactttctca acacttcaac gcgttgatct cattcgattc   120
ttacaagtgg agggagaaag gatggtttgt catcaccctt actttatgga taaggaaacc   180
aagatagcat ggcttggcaa tttatccaga gaagcaaaat gaccgacaac aacgcacggt   240
gaaacgcagt gttgggaatc gcagatggaa gccgagcatt tcctctacct gtgggacctg   300
cacttttcct aatgctcttt cccatgtgtt ctctgcaggt cctcaggcaa atcctgtgga   360
ggagaaaggg caaagtcatc ccagtgtctc gttttgagg gaacttgtgg ctgccatgtg   420
gacagtacca ggggatatgt ctcagcagcc ggccgggaac tcttggctgc agacagttgc   480
acagctcgtt atcttgatgc                                               500
```

<210> SEQ ID NO 57
<211> LENGTH: 500
<212> TYPE: DNA
<213> ORGANISM: homo sapiens

<400> SEQUENCE: 57

```
gcatcaagat aacgagctgt gcaactgtct gcagccaaga gttcccggcc ggctgctgag    60
acatatcccc tggtactgtc cacatggcag ccacaagttc cctcaaaaac gagacactgg   120
gatgactttg ccctttctcc tccacaggat ttgcctgagg acctgcagag aacacatggg   180
aaagagcatt aggaaaagtg caggtcccac aggtagagga aatgctcggc ttccatctgc   240
gattcccaac actgcgtttc accgtgcgtt gttgtcggtc attttgcttc tctggataaa   300
ttgccaagcc atgctatctt ggtttcctta tccataaagt aagggtgatg acaaaccatc   360
ctttctccct ccacttgtaa gaatcgaatg agatcaacgc gttgaagtgt tgagaaagtc   420
aagatagcag agaaatgaaa agctcctcct tccctctgtt ccttccagga acgtgtattg   480
agcccccagc acgtaagtgc                                              500

<210> SEQ ID NO 58
<211> LENGTH: 500
<212> TYPE: DNA
<213> ORGANISM: homo sapiens

<400> SEQUENCE: 58
agacaagtcc gccgagtgag tgtctgagga tggagacgcg aagggaatgg ggaggggcgg    60
gctctgttgc cgcttaccct ggagctgggg ctccagtttt ccagtcgaag ttctcctctc   120
tgcctacatc tcggattctg ggtctcagat gcaatcgcgc acccaaattg catcctgtga   180
acagaaaaag tctcaaacat gcgtacaaag aatattcaga agcagaagca atttctgaag   240
agcgaggccc gggactgagt tggcgagact cccagttcga gtgagcgaag ccagggtgga   300
gggctccgga ccgagattcc tgaaagcctc cctgacaccg atcctgagc gcaggacggg    360
cccagccact tgggggcgcc gctggcccca aagtaccggg agcttaccct ccgctgacca   420
ggattcaccc tggctggcag agactaccct acgctccgct cacccggcca cccgccccg    480
ctctgcgctg accctccgtt                                              500

<210> SEQ ID NO 59
<211> LENGTH: 500
<212> TYPE: DNA
<213> ORGANISM: homo sapiens

<400> SEQUENCE: 59
cagaaacaaa gtcaataaag tgaaaataaa taaaaatcct tgaacaaatc cgaaaaggct    60
tggagtcctc gcccagatct ctctcccctg cgagccctt ttatttgaga aggaaaaga    120
gaaaagagaa tcgtttaagg gaacccggcg cccagccagg ctccagtggc ccgaacgggg   180
cggcgagggc ggcgagggcg ccgaggtccg gcccatccca gtcctgtggg gctggccggg   240
cagagacccc ggaccaggc ccaggcctaa cctgctaaat gtccccggac ggttctggtc    300
tcctcggcca ctttcagtgc gtcggttcgt tttgattctt tttcttttgt gcacataaga   360
aataaataat aataataaat aaagaataaa attttgtatg tcactcccca tggctccaag   420
tttgtctctc cctgtctctg agatgggcct cccctccatt ggtcgatccc caaaagcccc   480
ttcaatgatc ctcccaacta                                              500

<210> SEQ ID NO 60
<211> LENGTH: 500
<212> TYPE: DNA
<213> ORGANISM: homo sapiens

<400> SEQUENCE: 60
```

```
ctctactagc cgcgcgcgtg ccagggccg ggttggatct gcccttttgg acagaggcct      60
tgtttgggga gggggatctg gggctaaggc taaggctttt ccttcggttc cttctctgct    120
ggccccagaa gccaccaaga gatttacaga ccaggccagt tgggcctcct tgctttcctc    180
agtccctgag aagcccgtga gaaacgtgcg gaagtaccag tgcaactctg ctggccttta   240
aggcttccac gttgggggac tgaggccaac tctccttgct cctggctggg gcatttgcac    300
ccaccgctca ttcttgctcc ccggtacctg gattttttctg tttccaccca attcgttctc   360
ccttttcccc tctctccagc cccttcagcg tatagcagtc gcctagttag ggctcagagt    420
ggaaggcctc ctgagggaat ggaaaggact gtgggtacaa ttaggtctct gcagcagaag    480
ccctttgtgg caaggccagg                                                500

<210> SEQ ID NO 61
<211> LENGTH: 500
<212> TYPE: DNA
<213> ORGANISM: homo sapiens

<400> SEQUENCE: 61
cctccgccgc gccccctccg cactcgcacg gccccacccg caggcgcccc ccgtgcggag     60
gaagcggatc tgccaggatc atttttgttg tgtcggagga tgaggttttg gctgaggact   120
gaagagatgg ccttggaaga aatggtgcag agattaaatg cggtttccaa gcacacgggt    180
aggaggagct gctggccgtc agtgatctgt gcttaagctt gacatcatgg gctgaaatgt   240
ggggaaatgc gtctgatttt tgtaagccgc cctcgtgttc cttttctagcc gtggtagctg   300 tgacatgggg ggcactggtt ggcagctggt gtgttttcag aggctgtcgg cgatcgtatg    360
ctgcccggga tagtcaaaat gactgcacgt tggtgacact ggctctctca gggttgctgg    420
gtctgcatgc ggagccattt gtgtgtctga agtctgccca tcaacctgcc tgtccgcagc    480
cctcgcaatg gagaatgcat                                                500

<210> SEQ ID NO 62
<211> LENGTH: 500
<212> TYPE: DNA
<213> ORGANISM: homo sapiens

<400> SEQUENCE: 62
aatgacgtca gaatcatttg catcccgctg cctctacctg cctggtccag ctgggaccct    60
gcctcgccgg ccgcatggcc agagggttgg gtgagtgtgt atggggaaga ggggctggac    120
tctggtatcc ttggatgggg ggcactccag gctctccagc ctcctcggct cagcctgggc    180
ccctccccat ccaacatcca ctccagtcct cattcaactt cctcttcctg cgaaagaggg   240
gcgctgcccc gtgacctaca cagactgaga cacgatcgcc atgaatggag acctctggaa    300
aagctcagga gccgaggccc acggggccca gcagaggcct gaggggagac cctgggcggg    360
ggctgaatca ctgcctcccg acagtccccc aatgcccggg ctttggaggg gagccgggag    420
cttcccatct ccttttgcag gggagggttg tcagtctggc gggatgtgca ctgggggcac    480
tccaacctct gctagctaac                                                500

<210> SEQ ID NO 63
<211> LENGTH: 500
<212> TYPE: DNA
<213> ORGANISM: homo sapiens

<400> SEQUENCE: 63
tctgagctgc tgcggggtgg aagtgggggg ctgcccactc cactcctccc atcccctccc    60
```

| | | |
|---|---|---|
| agcctcctcc tccggcagga actgaacaga accacaaaaa gtctacattt atttaatatg | 120 | |
| atggtctttg caaaaaggaa caaaacaaca caaaagccca ccaggctgct gctttgtgga | 180 | |
| aagacggtgt gtgtcgtgtg aaggcgaaac ccggtgtaca taacccctcc ccctccgccc | 240 | |
| cgccccgccc ggcccgtag agtccctgtc gcccgccggc cctgcctgta gatacgcccc | 300 | |
| gctgtctgtg ctgtgagagt cgccgctcgc tgggggggaa gggggggaca cagctacacg | 360 | |
| cccattaaag cacagcacgt cctggggag ggggcatttt tttatgttac aaaaaaaaat | 420 | |
| tacgaaagaa aagaaatctc tatgcaaaat gacgaacatg gtcctgtgga ctcctctggc | 480 | |
| ctgttttgtt ggctctttct | 500 | |

<210> SEQ ID NO 64
<211> LENGTH: 500
<212> TYPE: DNA
<213> ORGANISM: homo sapiens

<400> SEQUENCE: 64

| | | |
|---|---|---|
| tcgtggctcc agtgtctgcc aggaggcttc tgaactcgac agcaagtggg gaatggatta | 60 | |
| gtaacttgtt tgctgcccca cccacatggg ggcaggttct gggaaattgg gatctacaag | 120 | |
| ccaaaaacca cagtgacctc agataagcaa atgacgaacg tcccatggac cttggctggg | 180 | |
| ggcaggaatg tataccaaag aaaggtaggc tcagtttgga gtgggggtac atgcccttc | 240 | |
| tgaaaagtgc gaaaccttca ccaggaccct tcacaccagg cattccacca agctccacag | 300 | |
| ggctgggagg gaattgacag tgaagatgtc agtctgctct ccctaagtcc agcccgggga | 360 | |
| gaaacagcgg gggatggtgg ggaagactag ggctacaggg ctaccctagc ggcttcccgg | 420 | |
| aagaagggg cttggccacc aggtaagtgt gtctggctga tgggagggcc caaaggcatg | 480 | |
| gagtgactct gggaggtgtc | 500 | |

<210> SEQ ID NO 65
<211> LENGTH: 500
<212> TYPE: DNA
<213> ORGANISM: homo sapiens

<400> SEQUENCE: 65

| | | |
|---|---|---|
| ggcagccgtt cccaggtcca ggttcactgc ccaggacctg gagtcttggg gctgccctgt | 60 | |
| gctcacagag ctcccaccag gtcctgcagg gccctgggtc cagcttccct gtccaccctg | 120 | |
| tccctgggag caatagctct caaaccctcc ctagatgctt tctaccctgg cccacagccc | 180 | |
| ctggcacctt gaagaggtag gtcttcccct gacagttgat gcgggtgaag gcggcatcga | 240 | |
| tggggccctc gatgccccag acatctcgga tgagcttggg gtacccaggc ctcactgcct | 300 | |
| tttcgtccag ttcatagcag tactgcccta gagtggagga gatggtgtga gagcagggac | 360 | |
| gctcctgggg cagacccgca tccccagtac ctgccctgga ttcacctcgg aaggcaaaga | 420 | |
| gggaaccgtt cttgaggtcg gtgaaggcgt cgaagggctt cccactgcac agctcctcct | 480 | |
| ctgctgggg ctgaggtctc | 500 | |

<210> SEQ ID NO 66
<211> LENGTH: 500
<212> TYPE: DNA
<213> ORGANISM: homo sapiens

<400> SEQUENCE: 66

| | | |
|---|---|---|
| ggcatccttt ggacggctgc aatcaatgaa actggattac aggcaccagg atgaagcggt | 60 | |

| | |
|---|---:|
| cgttttaagt tacgtgaatg gtgatcgttg ccctccaggt aaatatttgc aatgaggtaa | 120 |
| ataaacttca agctcatagt aaactagaaa ttagacatag cagcagaaag aagctgcgga | 180 |
| gtggagctcc acggtcctat gagtgctgta accttgggcg tgaatgtgag ctgttcctct | 240 |
| gtacacccc ggtgtgaatg ctggtgtgtg aatcacgctg tgttctctca gttgcctggt | 300 |
| gagttttggc aggtgaatgc cggttgtcac gtaggtgctt taggatgggc agcttcctta | 360 |
| gggactgctg ctgcattctg aggtgattgt gcctggcgag gcacagctgc cacactgata | 420 |
| atgttcttct tctttccaga aaccgatgac ggcgtcccct gtgtcttccc cttcatattc | 480 |
| aatgggaaga gctacgagga | 500 |

<210> SEQ ID NO 67
<211> LENGTH: 500
<212> TYPE: DNA
<213> ORGANISM: homo sapiens

<400> SEQUENCE: 67

| | |
|---|---:|
| cagggcaggt tttctgcaga gcacggaaga ttcagctgaa gtcagagagg tgaagccagt | 60 |
| ttcccagggt aacatagtga ggcactgaaa gaaaggagac tgcactggag cccaggtccc | 120 |
| cgggctcccc agagctcctt actcttcctc tcctcagca gcctggagac ccacaaacct | 180 |
| ccagccggag gcctgaagca tgaggccatg ccaggtgcca ggtgatgctg gaattttcc | 240 |
| cgggagcttc gggtcttccc agcactctgg tctcgcccgc cctgcctctc gggctctgcc | 300 |
| cagcttcctg agtcctgaca gagcacagtg ggggagatgt tggcagaggt ggcagatggg | 360 |
| ctcacggcca tccctcctgc aggagcagcg actggaccca gagccatgtg gctgtgccct | 420 |
| ctggccctca acctcatctt gatggcagcc tctggtgctg tgtgcgaagt gaaggacgtt | 480 |
| tgtgttggaa gccctggtat | 500 |

<210> SEQ ID NO 68
<211> LENGTH: 500
<212> TYPE: DNA
<213> ORGANISM: homo sapiens

<400> SEQUENCE: 68

| | |
|---|---:|
| ctccccagat gccttgtagg cctgtgacac tggtgttgag ggagacattg tccatccctg | 60 |
| gaaccctctg ctcaacaggg ggacagtcag agacttgagc atccaacccc cacttcctgc | 120 |
| cagctctgtg ctcagggacc cacagagtca agcaagttat tgaattcagc ataccgaatt | 180 |
| ttatttattg ccgctcagga gggtgggggc ctgctgaaag acagggtcgg ggcctgcctc | 240 |
| ctgcatcccc ggcccaaaag cccgggccaa gaaggacaca ggcttcaatg gctgtcatgt | 300 |
| gttgcagaca acatggtgtt gagatcttgc atggtggagg gtgacgctgg tccctgaagg | 360 |
| gagatggagg aggaggcaga gctgggaaca aagggttaaa gggcgccatg taagagagct | 420 |
| ctccattccc accacggaga catccagacc ccagcagagg cccaaactga ctcacaaaca | 480 |
| cacagcccca tctttcccct | 500 |

<210> SEQ ID NO 69
<211> LENGTH: 500
<212> TYPE: DNA
<213> ORGANISM: homo sapiens

<400> SEQUENCE: 69

| | |
|---|---:|
| gcagggcggg cggccaggat catgtccacc accacatgcc aagtggtggc gttcctcctg | 60 |
| tccatcctgg ggctggccgg ctgcatcgcg gccaccggga tggacatgtg gagcacccag | 120 |

```
gacctgtacg acaaccccgt cacctccgtg ttccagtacg aagggctctg gaggagctgc    180
gtgaggcaga gttcaggctt caccgaatgc aggccctatt tcaccatcct gggacttcca    240
ggtaggcacc gtgcacccg gggtagagcc aggtgaacca ggtgagcagg aaggggggcg     300
tttgcgttaa gccccactcc cacctctggg tgaggaccct ggcagctctg gctcagaatg    360
aaaggtgtga ataaaaggag aagctggctc gtgtctaata gggcaacagt catgcaggag    420
aaaatgggag ggttaatact caaggcgaag gaatcgctag tgaggaggca ggcctcaaga    480
agaatgggtc tattgtaagg                                               500

<210> SEQ ID NO 70
<211> LENGTH: 500
<212> TYPE: DNA
<213> ORGANISM: homo sapiens

<400> SEQUENCE: 70
ccgtgcccat ggagaggctg gcctgctagg ctgtggggcc cgatggcctg acactgtatg     60
gaccacgctc ctgccctgcc ctgccccgcc ctgccgtgg cccgtgtgca gaagtgggca    120
ggcctgggtt gctgggccag agccccgaga tttccccctg ccccactggc tgagtgtggg    180
ggagctgctt ctccacttcc gcgtgggtct tggccctggg aggccagtgg ccgaggctgg    240
tctcgcgggc gctcgctcca ggagtggcgc gtccctcag cgccctgtgc ttcctcgcag     300
ggatcgacta caagaccacc accatcctgc tggacggccg gcgcgtgaag ctggagctct    360
ggtgagttgg ggctgcggca cttcagttcc tgggtgagga cacaaatgcc gaagggagaa    420
cagaaccctt agagaaacag gaaggcgtcc tgtttgcatt tcacttggaa gagccactta    480
cacagcccct gtttaaacat                                               500

<210> SEQ ID NO 71
<211> LENGTH: 500
<212> TYPE: DNA
<213> ORGANISM: homo sapiens

<400> SEQUENCE: 71
tacgacttcg tggggaagct ggagactctg gacgaggacg ccgcgcagct gctgcagcta     60
ctccaggtgg accggcagct ccgcttcccc ccgagctacc ggaacaggac cgccagcagc    120
tgggaggagg actggttcgc caagatcccc ctggcctgga ggcagcagct gtataaactc    180
tacgaggccg actttgttct cttcggctac cccaagcccg aaaacctcct ccgagactga    240
aagctttcgc gttgcttttt ctcgcgtgcc tggaacctga cgcacgcgca ctccagtttt    300
tttatgacct acgattttgc aatctgggct tcttgttcac tccactgcct ctatccattg    360
agtactgtat cgatattgtt ttttaagatt aatatattc aggtatttaa tacgaaatgt    420
ggaagggaat gctggagtaa aatatcccct ctcccctccg cccgcccacc cgcccgcccg    480
ctcgcccgct cgcccgctcc                                               500

<210> SEQ ID NO 72
<211> LENGTH: 650
<212> TYPE: DNA
<213> ORGANISM: homo sapiens

<400> SEQUENCE: 72
ctacggacac atataagacc ctggtcacac ctgggagagg aggagaggag agcatagcac     60
ctgcagcaag atggatgtgg gcagcaaaga ggtcctgatg gagagcccgc cggtgagtgt    120
```

```
ggttgcgtgt gtgtatgtat gtgtgcgcgc gcacatgtgt gtgatgggcc ctgcctcctc        180
tatcctccct ggcctgtttc cttatccaga tccattcact caactaacct aggactgtga        240
taagtcagga tggggacacc aagaccacta agccagggac ccttggggag ctgtttgtgg        300
gccaagagcc actataqggg tccgtagaaa gggctgtccg tagacagccc tgagtcagaa        360
gccatgagaa acttcagaag tcaggggaca cttctcagag aaaaaccaca tacgagctgg        420
agccagaata aggaggagct cgcccggtgg agaaggagga aggcattcca ggaaggaggg        480
agactctgta tcaccgcatg gcacatgtgt gtgatgggcc ctgcctcctc tatcctccct        540
ggcctgtttc cttatccaga tccattcact caactaacct aggactgtga taagtcagga        600
tggggacacc aagaccacta agccagggac ccttggggag ctgtttgtgg                   650
```

<210> SEQ ID NO 73
<211> LENGTH: 500
<212> TYPE: DNA
<213> ORGANISM: homo sapiens

<400> SEQUENCE: 73

```
ccgctgggcc tcccgcgttg cctggagagg cagaaccgag gctcggcttc cacttggagt        60
ctcccaggtg agctccagcc tgcgacgtcg gcaggggcga ggccccactt ccgcgcctgc        120
gcgccagcct cccgccccgc cccagcccta cctgagcgct ccaggtgaga accttggatc        180
gcgcgcgcag ggtgggggcg ccgtccgggc caagcctggc tgtcgcgcgg cttctctctg        240
agtggtcggc gaggctgctg ctccgcgcaa gttgtggctc ccggcccatc tacattggag        300
gaatcctgca ctgacctggt ggcagtgatc accttgtagc cagaacacag tctgctgggt        360
ccttggggaa ccagaagttc tagatttccc ccacacggtt cctcccttcc tcctcggttc        420
gccaaaatga agggtgcgc tgcctccgag gaccacttcg ggagggcagc aactgctggc         480
tcatgtggtt tcttcgggca                                                    500
```

<210> SEQ ID NO 74
<211> LENGTH: 500
<212> TYPE: DNA
<213> ORGANISM: homo sapiens

<400> SEQUENCE: 74

```
ggagggaggg aagggagaag agaatacgaa ttaattacga aggaaaccca ggtgtgaaag        60
gcacccgccg cggagctggg cgtgcagcgg ggcgcgcggt gggacctctg ctcccgtccc        120
cgtcccgcgg ctactcagtt gcccgctcat gggaggctcg cgacggaaaa taaatcccct        180
cagagtgaac ctgggaggcc gagaggaccc agcctgggat ctctggggga aatagggca         240 agtttaccac ggtttaatta agccacagcc ctagcacgag gaccccggcg acccatccgg        300
gctgggggat ggactggagt gccccccacc ccaggccgcg aaccggcagc gagaagcaca        360
ctctccgcca tccccggccc cgccgcttcc gcctctgcgg actccgcgtt tgccatgctc        420
cttcccgggg tccagggacc ggagctgcgg tgcacgtctt attgaagggg agagctttgg        480 ttctttttcct ccctgcatcc                                                   500
```

<210> SEQ ID NO 75
<211> LENGTH: 500
<212> TYPE: DNA
<213> ORGANISM: homo sapiens

<400> SEQUENCE: 75

```
ggatgcaggg aggaaaagaa ccaaagctct ccccttcaat aagacgtgca ccgcagctcc        60
```

```
ggtccctgga ccccgggaag gagcatggca aacgcggagt ccgcagaggc ggaagcggcg    120
gggccgggga tggcggagag tgtgcttctc gctgccggtt cgcggcctgg ggtgggggc    180 actccagtcc atccccagc ccggatgggt cgccggggtc ctcgtgctag ggctgtggct    240
taattaaacc gtggtaaact tgcccctatt tcccccagag atcccaggct gggtcctctc    300
ggcctcccag gttcactctg aggggattta ttttccgtcg cgagcctccc atgagcgggc    360
aactgagtag ccgcgggacg gggacgggag cagaggtccc accgcgcgcc ccgctgcacg    420
cccagctccg cggcgggtgc ctttcacacc tgggtttcct tcgtaattaa ttcgtattct    480
cttctccctt ccctccctcc                                               500
```

<210> SEQ ID NO 76
<211> LENGTH: 500
<212> TYPE: DNA
<213> ORGANISM: homo sapiens

<400> SEQUENCE: 76

```
gtctggctct gtagcccagg ctggagtgca gtggcgcgat ctcggctcac tgcaacctcc    60
gcctcccggg ttcaagcagt tctgcctcag cctcccgaag ggcgccacca tgcctggcta    120
atttttgcat ttttagtaga cagggtttt cgccatgttg gccaggctgg tctcgaactc    180
ctgacctcaa gctatctgcc cgcctcggcc tcccagagtg ccgagattac aggcgtgagc    240
caccgcgccc ggcctaccct tgaagacccc gcagccaagg tcctccggcc ccgctctgcg    300
cggcgctctg gtcttggggc tccggactct gtcatgccgg cagggggcca gtccgatcct    360
tgcacccttg cctggcaccg tccctggagc cttggcgtcc tggcctctcc tccccgcggg    420
ctggaggtgg agtggccggg ccggaaccag tgcgcaaagc agatggcgag cgcggaggtc    480
ggttcggccc cgccgcgcct                                               500
```

<210> SEQ ID NO 77
<211> LENGTH: 500
<212> TYPE: DNA
<213> ORGANISM: homo sapiens

<400> SEQUENCE: 77

```
aggcgcggcg gggccgaacc gacctccgcg ctcgccatct gctttgcgca ctggttccgg    60
cccggccact ccacctccag cccgcgggga ggagaggcca ggacgccaag gctccaggga    120
cggtgccagg caagggtgca aggatcggac tggcccctgc ccggcatgac agagtccgga    180
gccccaagac cagagcgccg cgcagagcgg ggccggagga ccttggctgc ggggtcttca    240
agggtaggcc gggcgcggtg gctcacgcct gtaatctcgg cactctggga ggccgaggcg    300
ggcagatagc ttgaggtcag gagttcgaga ccagcctggc caacatggcg aaaccctgtc    360
tctactaaaa atgcaaaaat tagccaggca tggtggcgcc cttcgggagg ctgaggcaga    420
actgcttgaa cccggggagc ggaggttgca gtgagccgag atcgcgccac tgcactccag    480
cctgggctac agagccagac                                               500
```

<210> SEQ ID NO 78
<211> LENGTH: 500
<212> TYPE: DNA
<213> ORGANISM: homo sapiens

<400> SEQUENCE: 78

```
agattacagg cgtgagccac cgcgcccggc ctacccttga agaccccgca gccaaggtcc    60
```

| | |
|---|---|
| tccggccccg ctctgcgcgg cgctctggtc ttggggctcc ggactctgtc atgccgggca | 120 |
| ggggccagtc cgatccttgc acccttgcct ggcaccgtcc ctggagcctt ggcgtcctgg | 180 |
| cctctcctcc ccgcgggctg aggtggagt ggccgggccg aaccagtgc gcaaagcaga | 240 |
| tggcgagcgc ggaggtcggt tcggccccgc cgcgcctcaa ggcagcagcc accctgggga | 300 |
| aggtggatgc cggaagaggc gtcgcctgcg ggtcacccag aggacacccg gcggggaatt | 360 |
| ccgagggtgg gagtgaggag aggtaggaga ggccacggca gagggaggcc ccgcgcagag | 420 |
| tgggaaccat cgcccggtgc gggcctgaac ttccagggcc ggctactcct cggcagagcg | 480 |
| accgcgcggt gtctcagagc | 500 |

<210> SEQ ID NO 79
<211> LENGTH: 500
<212> TYPE: DNA
<213> ORGANISM: homo sapiens

<400> SEQUENCE: 79

| | |
|---|---|
| gctctgagac accgcgcggt cgctctgccg aggagtagcc ggccctggaa gttcaggccc | 60 |
| gcaccgggcg atggttccca ctctgcgcgg ggcctccctc tgccgtggcc tctcctacct | 120 |
| ctcctcactc ccaccctcgg aattcccgc cgggtgtcct ctgggtgacc cgcaggcgac | 180 |
| gcctcttccg gcatccacct tccccagggt ggctgctgcc ttgaggcgcg gcggggccga | 240 |
| accgacctcc gcgctcgcca tctgctttgc gcactggttc cggcccggcc actccacctc | 300 |
| cagcccgcgg ggaggagagg ccaggacgcc aaggctccag ggacggtgcc aggcaagggt | 360 |
| gcaaggatcg gactggcccc tgcccggcat gacagagtcc ggagccccaa gaccagagcg | 420 |
| ccgcgcagag cggggccgga ggaccttggc tgcggggtct tcaagggtag gccgggcgcg | 480 |
| gtggctcacg cctgtaatct | 500 |

<210> SEQ ID NO 80
<211> LENGTH: 500
<212> TYPE: DNA
<213> ORGANISM: homo sapiens

<400> SEQUENCE: 80

| | |
|---|---|
| caaggagata cgttccctgc catggaggaa gttggaccac gaccttgttt attgggttgc | 60 |
| gtctgttttg tctatctcca gaaagcatca ggactccaaa aaggaagaag aaaagaagaa | 120 |
| gccccacata aagaaacctc ttaatgcatt catgttgtat atgaaggaaa tgagagcaaa | 180 |
| ggtcgtagct gagtgcacgt tgaaagaaag cgcggccatc aaccagatcc ttgggcggag | 240 |
| ggtaggtgac gcccttctca gggagaagcg gggggcgggt ggtgagggac cagagtgcag | 300 |
| caggtcaggt ggcagaatgt ctctgtcccc atttctttgg agaattcttg cccttcagcc | 360 |
| acattctgaa tccttgaatg gccttcactg agtcaggact agttattctg cactcagcgt | 420 |
| tcagaacagc cacagccatg ctcttcccct acccgagcga gtgagcaaat gacagaatga | 480 |
| catagataac aaatcaagtt | 500 |

<210> SEQ ID NO 81
<211> LENGTH: 500
<212> TYPE: DNA
<213> ORGANISM: homo sapiens

<400> SEQUENCE: 81

| | |
|---|---|
| atatctctta gaatcaccaa tggccaacat ccttgtctca gttcaaattc ctggaagagg | 60 |
| taatctggtt gtctgagtgc ttcactcttt agaaactaac aaatcatggg ttactggcta | 120 |

```
gctgggcctt tggacagggc aagcaacaat tgacacattt aagatggcag ataaaaaatt    180
atgatcttta tttgagaggt aaggaaacta aatcttgcca ggttaagcaa tctgcaaacg    240
ttcgcatgac gtttatgcag ccgagtcaca tccacattct ctccctgtca gttcctttcc    300
cgggagctag aaatattgaa gtcatttaag taggagatga ttattagaca tatacgtaca    360
actataggtt tttgtattta tgttttatta attgacaaga gtacaaatct aattaaagga    420
gaaattgcat tggcttaaaa taagagaata aattatttct ttttggtagt taatacaact    480
aaagctctca tttgtaccct                                                500

<210> SEQ ID NO 82
<211> LENGTH: 500
<212> TYPE: DNA
<213> ORGANISM: homo sapiens

<400> SEQUENCE: 82
agatgtctag gaggctctga atgagcgact gtgacggcca cctgtaagtt tcacggcaac     60
agagttgtga ggtggcgact tcagtacctt tctgtcctcc ctctggatag tctcagtccc    120
cacaggaggc ccttctactc ttgcttagtg gacaacgctc caccagccca gactcaatgc    180
tgagtgggga caaagctggt catctcggcg gtcacacaga gttcacttac cgtagtccat    240
aaggcacccc gtcccgaaaa gcgccaagtg cacgaccatc ggctttaccg cctgctcagc    300
acgcctaatg cccgccccgg ctgcactggg ctgagcaagg accagggcct ctgagcagcc    360
ggctcacaac acactcttat gtcctcgtgt ggccactctg gaagtaagca gtcacagctc    420
ccaagcgtgg tcaaaactct gcagcacaga tcaagctagc tctcagcttt ccccactccc    480
aaattagcat ttggtttct                                                 500

<210> SEQ ID NO 83
<211> LENGTH: 500
<212> TYPE: DNA
<213> ORGANISM: homo sapiens

<400> SEQUENCE: 83
agcccgcgtc ccttgcatga ttgttgtaag aaagccccag ctcagctgcg tggagacagg     60
gtcctcttgg ctgcaaattc taaaatcatt tttcctatga agagagcagt gctaattttt    120
tccaaaatat atcagattat gatcgacttg actgaagtgt gaaatgaaag tgggttggag    180
tgttcctgcc aaagacaagc acggctgcct tgccgtcgct cgtgccgtgc tctctaccct    240
ccacagtcac ggtgccggac cctctcccga taactggaca cgtgtctccc acaggacacg    300
cactggcact aaatccacac tgcccatctc ggagacaggc ggaggaactc ccgagctgag    360
atgcggaaag caccaggccg tagggacctc accgcagcgg gccgcagctc aggactcgga    420
gcaggtgggc cacaccatgc cgcatgtttc cagctgccac cgcagtggtt ggacaggatc    480
tgggtgtcgg agcagctctg                                                500

<210> SEQ ID NO 84
<211> LENGTH: 500
<212> TYPE: DNA
<213> ORGANISM: homo sapiens

<400> SEQUENCE: 84
atactcgcag ctaccctca gctgacccga gctgtgtgcc cggctgaggc cacaggcaaa      60
gccagggaca ctgtcctcag gctccttacg agaacgacag aggcatctcc agcgcgtcac    120
```

```
cgagccctaa atagagtagc ccagccacgg caccccccac caagacttct tggactgggc    180
ggcagcacgc ggccaggcca ggcggccgga caggtgggga ggtctctgtg gctcgacagg    240
tggggaggtc tctgtggctc tccacgcccc cattggtctg aggaggactc tatgcccttt    300
ctgagcaggg gcccagcctg ggggaggcca tttataccac tcccctggg cccaccagcc    360 caactcgccg ctgccggcct gacctcgctc ccagccctgc tgcccagatt ctaggtgagg    420
cccagcccgg cccgccgagg ccggggggaca gggcgtggct cgagctggtt tgagggagga    480
cttcctgggg cggggtctg                                                 500

<210> SEQ ID NO 85
<211> LENGTH: 500
<212> TYPE: DNA
<213> ORGANISM: homo sapiens

<400> SEQUENCE: 85
tgcgaagaaa gcacagaacc catgaaacgg aacagggccc aggcagccca ggagcctgga     60
agggggcagt ggggcgagat gcagcccacc agggttcgcg gcagcccagc ccttcgcccc    120
cgggaggggc tggccggagg tctgagggag acccccagga gggaccctga aggaggggaa    180
caggaaggct ctgggcggga cctgacgcgt gggtccttgg cgaggaagcg gggttgggtc    240
ccgagatcac gtaccagctc agagtggccc tcacgcagcc cgctgcagcc gtgcggcctc    300
ctccaacatg cgcatgtcgc gcagcacggc cacgacgagc tcggctgcgt agtcctcgta    360
gtaggaggcg accagcttgt cggtgaggtc cacgatatct agctgcccga gcgcgccccg    420
cgggatgcgc tcaaagccct cgcgcagcgg caccgtcccc agcttcatct tgaacttctt    480
gagctcctcc ggtgtcaggt                                                500

<210> SEQ ID NO 86
<211> LENGTH: 500
<212> TYPE: DNA
<213> ORGANISM: homo sapiens

<400> SEQUENCE: 86
atcctggtaa acttgccaag ccccagatgc agcagacaca gcctcaggcc tatgcttact     60
cggatgtgga caccccagcc ggtggcgaac cactgcaggc cgatggcatg ccatgatcc     120 gttcctctct ggctgctttg dacaaccacg gcggtgaccc cctgggcagt cgagcatctt    180
ccaccactta taggaactca gagggtcagt ttttctccag catgactctc tgggggctag    240
cgatgaagac gctgcagaat gaaaacgagt tagaccagtg atgtaccgcg cttctccacg    300
gtagaggcgt gttctcagtt tagcaggctg gtgttaaggc tgtaggagga cccagtttcc    360
ccatgacagt gccttctaac tagccagaga ataggtagct tccctcctga tgatggctca    420
taatctgaag catcttgagc tgggggtgtg aggggaggg cctgctggct caccgtgagg    480
cagccgcggg agggagcgct                                                500

<210> SEQ ID NO 87
<211> LENGTH: 500
<212> TYPE: DNA
<213> ORGANISM: homo sapiens

<400> SEQUENCE: 87
ctcggctgcc ttcagctgca ctgtgtctgt tacctcccgt tacaccttgc tggtgggctg     60
taacacacag gggcagtccg atgtcacctg ccatgggga gcagagagga ggagcggctt    120
ggcccccggc tgctcctggg gtgtcagtgg tggcagtgcc cagggcgagc ccagaacatg    180
```

```
aaccagcact cggcccgtca ggggagatcg gggcctgtca gtgcccctaa gcctgaaggt    240
gcaggtctcc gagcccagc ggagccggcc tcgtggaagg acgagggaaa gaatgcgtgg    300
tgcacggggc catgtgtgtg tgtgggctcc ttgcacctca tcgcggtctg gaagatttct    360
gtgcctagat ttggtgaatg ttcatatttc ccttacaagc tgtcatttta aggatatgga    420
ggagaataaa gagcaggctg aaaatatttt aagaatcaag gaatctgtct ttaaaaaaag    480
gtttggatga gattgtatgt                                                500
```

<210> SEQ ID NO 88
<211> LENGTH: 500
<212> TYPE: DNA
<213> ORGANISM: homo sapiens

<400> SEQUENCE: 88

```
ctcctgctgc tgccccgaca cccaggtccc caaacagggt gtccgcatgg atccgcactc     60
caacatcctt ctgcaccagg aaaacagggc aggggagggg gaaaataagg cagggacgag    120
ggccaacacc cccgtgtcct caccagccca cgacctgtat gagtggacag aagcgtgca    180 gcacaaagct ggatacccc tcagctcatc cgcgagatcc gcaacagcac cgtcacctga    240
cgaggaaccc gacacacatg gctcccacct gggctcctgt tttctgctaa gaaaatggta    300
caactgccaa attccacaag attccttctg tttcagtaca ctcttctggc ccctacttga    360
ggtctgagcg cacaaccctg tggggcctgg aagtcctggt ctcatgcccc aggcggtcgc    420
ccacacacag tgaggaacac cccaacttca cttttcagggg tgctggcagg atggttatcg    480
gagagagtgc ctgattataa                                                500
```

<210> SEQ ID NO 89
<211> LENGTH: 500
<212> TYPE: DNA
<213> ORGANISM: homo sapiens

<400> SEQUENCE: 89

```
agtttacgat tggctcaatg catgcccact aacgctacag gggccgctct gccagccccc     60
cgcatgccga tggtctttc ccgtctgcgc cggatttacg cctctctttt cagccggtta    120
ccatgttcca accgggcacg aatcactcgc tcttgtcatt ttggtggaga aggtaatgct    180
gctggaatta tggaagagcc cgatccacat ttacagagcc ctgcgtgcca gagagaaagc    240
aggctcgcgc gcacatgcag gcctccaaat gcatccagca gccgtctgaa gtcaatgttt    300
gtgccatttc cttttaaata ttctcagaac agctaaattc tggcgaagcg ctcgactctg    360
tgcagtcaga tggctgggtt gctgctgcat cccccacagc caatgctctg cttgtgggga    420
tctggcaaac cagggactct caccagctag tcccaaacat gtcccaggaa tgaagccgat    480
ttacctcccg attaaaatat                                                500
```

<210> SEQ ID NO 90
<211> LENGTH: 500
<212> TYPE: DNA
<213> ORGANISM: homo sapiens

<400> SEQUENCE: 90

```
cgtatgtctg agtttgcacg tgctgtttta ctcatggtgt tttcaagacg tatctgtgtt     60
gctccacatc cgttgggttc attcacttca accactgcct gtgctgtatg tagtgtgtgg    120
gcaccatttg tccacctgtt tcaccatcag tggtgtcgca cctgtttcct ggagtatgtg    180
```

| | |
|---|---|
| tgggtcagtt cctctgagat gtgtacccaa ggcctgcttt gagatgtgag aaccgtcagt | 240 |
| cgggcttggc gggggccgcg cctccatgct cccaggcagc acacattcct cagtctcgac | 300 |
| tctcgcccgt tgtgagcctg caaggatgcc acactgacgt cacaaacagt gcacgtgctt | 360 |
| ggaagcagtt ctggtttctt ttctgtgagc tgtgttgtca tggtctttgc ccatttttat | 420 |
| cttgggctgc ttgtcctttc cttagggatg tgtagggctc ttcaggccct tgggaaaagc | 480 |
| tgtcctggtg acagaggccc | 500 |

<210> SEQ ID NO 91
<211> LENGTH: 500
<212> TYPE: DNA
<213> ORGANISM: homo sapiens

<400> SEQUENCE: 91

| | |
|---|---|
| tttcttgctt gtaaatggct tttttatggt ataaataaag tcaatggaca ttgctgtttg | 60 |
| taaataaaaa tgctgctaga gcaaatgtgc tgtggtctcc ctctgcgtgg gcccctgag | 120 |
| cttcggtgag tgtcagtggc tctgacaaac atctgcagtg tcatagtttc tgtaatcact | 180 |
| gttttttgaaa ggtgagggtt tcctaagaag ctcttgtgcc accatcgtgc tgaaaagaag | 240 |
| agaaagaagc gagtatattt ctgacctctt gtgtggcgac tgaattgtcg gcctcggtct | 300 |
| gcacccaggc accccagaa caaatcgtga atccctgccc ctcgcgcctg cagagaatat | 360 |
| ctcttgctca gtcgtccaca aagggtgggg ttgcccagge tcttctgtct ccactcagcc | 420 |
| agttaactcc ccctcctcct ccaggttcca gcccagggac ccctcttccc accagcagcc | 480 |
| ctccaggtca ggcccctcta | 500 |

<210> SEQ ID NO 92
<211> LENGTH: 500
<212> TYPE: DNA
<213> ORGANISM: homo sapiens

<400> SEQUENCE: 92

| | |
|---|---|
| aagaaccgag atgagcttgt gggtctacta tctaatcgcc ttttctactt gtaggctgcc | 60 |
| aaggcccgta gagacaggaa gctggttttt ctcgaggctt cacatggtca ccttattgcc | 120 |
| aacaaacact gcaaggcttt attagctaaa atgtcaaccc acacacagat cagagaccgc | 180 |
| cctcagcttc tctgcgcctt tccgccccgt caccgcatca atggggtgga ggccaaactc | 240 |
| aaacacttgc ggggcacaga cgtcccagaa gcaaacatgc aagtcacggg agtttattta | 300 |
| tttaatttttt ttccccagat ggagactctg tcgcccaggc tggagtgcaa tggtgtgatc | 360 |
| ttggctcact gcaacctcca cctcctgggt tcaagcgatt ctcctgccac agcctcccga | 420 |
| gtagctggga ttacaggtgc ccgccaccac acccagctaa ttttttatatt tttagtaaag | 480 |
| acagggtttc cccatgttgg | 500 |

<210> SEQ ID NO 93
<211> LENGTH: 500
<212> TYPE: DNA
<213> ORGANISM: homo sapiens

<400> SEQUENCE: 93

| | |
|---|---|
| atttgagcta ggttttttact tcctttcaac cctctgcttg atagaattgc ttatcttgtc | 60 |
| cttttttattt tctttaatgc atatagatgg gcaccagttg cgtcttgaag tgccatcagc | 120 |
| tgtaaccaaa gttccacatc ccaagacgac agccaggcgt tcctgcccte aagaactgaa | 180 |
| gacaatggag ctctctgata gtgaccgacc cgtcagcttc ggttccacat catcctcggc | 240 |

```
ctcttcccgc gacagccatg gttccttcgg cagcagaatg accttagttt caaatagcca      300
catgggcttg tttaaccagg ataaggaggt aggggccata aaactggagc tgattcctgc      360
caggccgttt tccagcagcg agctgcagag ggacaacccc gccacggggc aacagaacgc      420
ggatgagggc agcgaaaggc cacccagagc gcagtggaga gtggactcaa acggggcacc      480
caagacgatc gcagactcgg                                                  500
```

<210> SEQ ID NO 94
<211> LENGTH: 500
<212> TYPE: DNA
<213> ORGANISM: homo sapiens

<400> SEQUENCE: 94

```
actccagcct gggtgacaga gggagaccct gtctctgaaa aaggggta aaaaaggat          60 tggggaccat gagttctgtg ccatgcttga ggcctggatg agccacgcct gaggagctgg      120
gctgggtggc cacggggagg ctgcgctggg accgagtcca gccccgctt cccgctcccg       180 tggccaggag ctgatccgca agggcatccc ccaccacttc cgggccatcg tgtggcagct      240
tctgtgcagc gccacggaca tgcccgtcaa gaaccagtac tccgagctgc tcaagatgtc      300
ctcgccgtgc gagaagctga tccgcaggga catcgcccgc acctaccgg aacatgagtt      360 cttcaagggc caggacagcc tgggccagga ggtcctcttc aacgtcatga aggtgaggcc      420
cagggctccc cgctccctcg gtcccaaagg aaggagaagt tccccagttc accggctgtg    480
ctggacggcg ggaccctgct                                                  500
```

<210> SEQ ID NO 95
<211> LENGTH: 500
<212> TYPE: DNA
<213> ORGANISM: homo sapiens

<400> SEQUENCE: 95

```
gcttggttct taagtacaga tgcctggttc tgggccatag gaccctcagt tctaaatatg       60
ggttcctggg acctggccac tggtgcatgg ttcacatcca aaagccctg gatggacctc      120 tggcttctgg cgatgggtgt ctggaattca gcctgggtgc ctggaatcct caaagtacac     180
tcctggtttc catccactgg ctcctggttt tggtgtatct tctggtggcg tttgagctca      240
gactggtccc ggaagctctt cccacacaca gagcatgaat ggggccggta acccagatgg     300
acgcggcggt gacgacttag tccagaagca tcacagtagg tcttgtcaca gagcgtgcaa     360
cagaagggcc tctccccaag atgcatgcgt ctgtgatagc tgagggactt ggggctccga    420
aacaacttcc cacactgact gcagctgtta gtcagcttgg gattgtgaac aaactggtgg     480
ctatagaggt aggagcgcct                                                  500
```

<210> SEQ ID NO 96
<211> LENGTH: 500
<212> TYPE: DNA
<213> ORGANISM: homo sapiens

<400> SEQUENCE: 96

```
aggcccttct ggccctgatc tgacagagga caggccccca ggagcctcct ggccatgctc       60
ctgcaggctc tagggtgtgg ggtgtgccga gctctgggca ctcggtcccc gagtcttagg     120
aagcctctca gagaaaacgg cacttaccct gatgcggagc agcaggtctg cgtaccaggc    180
cgccaggccc atcatggagg ggtaggcccg ggccacccac gtatcaggca cggtgtcata    240
```

| | |
|---|---|
| gaagagagcc gtggacagat cttccacgtc ggtcgtgatg gtcagttctc cctaggagac | 300 |
| acacagatgg gtgtggggag ccctgagctg gggcctggga gagcaccagc cccagtgcgt | 360 |
| gtcatgagtt gtcaacacag tgtggctttg tgctgcgcct ctggagacgc cctgcatcag | 420 |
| ggccacgcaa gcgcttcctg ctaaggaacg gtctagatga gctcccgggg cttgttctgg | 480 |
| aactgccaga gctctggaga | 500 |

<210> SEQ ID NO 97
<211> LENGTH: 500
<212> TYPE: DNA
<213> ORGANISM: homo sapiens

<400> SEQUENCE: 97

| | |
|---|---|
| ctgaaacctc ctgggtgtaa ggccatgaat ctgctcgact tgctcacggg cgggaaggaa | 60 |
| acaaggaaac aacgaaaagt ttcctgcgaa gtgaccaaca tcccctattt tttaaaaatt | 120 |
| ccgtgtgaga cctgagaaca cactgtgaag cggggttcgg agaacgaccc ctcccgcgtt | 180 |
| ccgcgcccag cggggtcgca gggctgcgag cccggctgta gcaaagctttt tcggccgcg | 240 |
| tcctccctcc ggattcggta ggccaggctc gggcgcgccc ttcccacacc aacaaaccat | 300 |
| ctttcccgac tcagcagagg cccacagggg cgcagccgct gtccctccgc ccttggccca | 360 |
| gcggcgccgc cctggtacgc caggcctgaa ggcagggccg gcccgcgcca cgcagggtct | 420 |
| cccttaggcg gcgccttagg gtgaaatgcg gggccaagcc tgacctgccg gggtgccccg | 480 |
| tggcatctct ggtgcggacc | 500 |

<210> SEQ ID NO 98
<211> LENGTH: 500
<212> TYPE: DNA
<213> ORGANISM: homo sapiens

<400> SEQUENCE: 98

| | |
|---|---|
| aacggcaccg tggacttccc cgagttcctg ggcatgatgg ccaggaagat gaaggacacg | 60 |
| gacaacgagg aggagatccg cgaggccttc cgcgtgttcg acaaggacgg caacggcttc | 120 |
| gtcagcgccg ccgagctgcg cacgtcatg acccggctgg gggagaagct gagtgacgag | 180 |
| gaggtggacg agatgatccg ggccgcggac acggacggag acggacaggt gaactacgag | 240 |
| gagtttgtcc gtgtgctggt gtccaagtga ggccggcgcc caccatgctc ctgggcgccc | 300 |
| acgcggccca cagggcaaga acccggggcc tcccgcctcc tcccccatcc ccctgcctcc | 360 |
| cctgggcact gtggcttcct cctgcgcctg gttgattcag cccacctctc tgcatcccgc | 420 |
| ttcccgcgtc tcttctctgc actcctgccg accttccac ctgctcgtct gaatgacacg | 480 |
| gaacgctccc actgcaggca | 500 |

<210> SEQ ID NO 99
<211> LENGTH: 500
<212> TYPE: DNA
<213> ORGANISM: homo sapiens

<400> SEQUENCE: 99

| | |
|---|---|
| acccacacgc caagcagaaa cccctcgaag cgggctggga gcacggaccc ctgatttata | 60 |
| gaggaggccc cggggggccct gtcggggggag ctgtggggac cggcccccca gagctcagca | 120 |
| cagcccggcc ctccttccag acaccagcac tcgcatgtcc cagcaggtga gggtgggtca | 180 |
| aacctgctgg atctgaagtt aattgttcga ctggaaggaa acctgtgcgc tccccggagc | 240 |
| atgacgccac gccgcctcct ggcgctgca gagccaaagc cactggcgtc tgccgggatg | 300 |

```
gaccttccct ggaaggagag acctcagccc cgcgtgggta ggacgcgcct gctgaacgcc    360
ctctcagggc cgacactgga aaacaccttc ctctaaagga acatccgagt cagaaaacag    420
gtgctcgcag caggcaccaa agcgcctttg cgaacgctta gggctgtttc aggaaaccgc    480
tcagtagcaa aggcagaaga                                                500

<210> SEQ ID NO 100
<211> LENGTH: 500
<212> TYPE: DNA
<213> ORGANISM: homo sapiens

<400> SEQUENCE: 100
gttaagtagt tatttgcagt tgttccgggt atttctcatt agaaataaca tcatctaaag    60
aacgatattg actgattttt ttaatcttgg agtcatggac gtgaaccaca tatttatatg    120
acattccctt taactagaat tctcgcgctt tatttttata ttattgatct ttttgacacg    180
aattgctttt tggccttgtg cgaatgttgt aagctttccg cctgcagagg aatgggctgg    240
cgtctgggcc gggctgggaa gagtgatcgc tccagccgcg tggcagtaac attcccgcac    300
atttaacaac aattagtctg tgccgacgcc atggtaggct ttcgtgtatg aaaatttaca    360
aggcttttaa tggactgcat tatggaaggc cgtgcgggc cagtcggtgg ggagataagg     420
ccgctgggcg tgcatccatc tcatggctca gtcggcccag tgtctctcag tgctcacgtc    480
tgcctcctgg gaggtgggag                                                500

<210> SEQ ID NO 101
<211> LENGTH: 500
<212> TYPE: DNA
<213> ORGANISM: homo sapiens

<400> SEQUENCE: 101
ccgctctggc tcctaagcaa ggagtacccg gaggtactct ttttgacagt aatgcgttaa    60
aggcaaagaa gaaagtatgg cttttcacagt tttactggga ggcctagaat gatttgaaac    120
ggacttttgt ttcattaatg ggaaaagcaa agcaaaacaa aaagcctatc atctaacact    180 cttccctgg atccaggaaa ttcttgtctg ctctacctca cacccaagct caggtgaccg     240
gtctgggtgc ggcgtggaga tggcgagagc taagtgctat ggccgcgaaa gggtgaaggg    300
cagggaggga aaaggccgag gggaggcgaa cgctcaggtt cacacatatg caagtgggct    360
ctacagcgga cttcgaagca tacactcaac tccccaccat gcgccggccc gctgctctac    420
ccctgaaaag ctctccctg gcccgcgatc cttgctggcc tacccttgg tcgttcccat      480 cccctctcc gccccgccc                                                  500

<210> SEQ ID NO 102
<211> LENGTH: 500
<212> TYPE: DNA
<213> ORGANISM: homo sapiens

<400> SEQUENCE: 102
aagaggagcc tctaaattta cagggaatac aaggaagtct actgttctct gctcctctct    60
gggttattag ggcacatggg agccctcagt tgttttctgc tgagcaagag caaagtccac    120
cttggactta gacagcttgc caaattttt gccagaaggg gacctgagtt gtgaccactc     180
ccagtgtgtg ccgggaaaag gctcgtactg gtgccagaat ctcttactgt caatgctccc    240
aaaactcacc gcttgccccc acccctttg cttaaatgac gtggttctta tctcagatcc     300
```

```
tgatataaag ctcctacagc tacctggcct gagaagccaa ctcagactca gccaacaggt        360
aagtgggcat tacaggagaa gggcgtctct aacatgcact gtagatctaa aatcttcggg        420
aagatacagc atgagtttct gtccaagagg ttttagctgt aatgaagcct cagtgggatc        480
caaagttgtt tttcagttac                                                    500

<210> SEQ ID NO 103
<211> LENGTH: 500
<212> TYPE: DNA
<213> ORGANISM: homo sapiens

<400> SEQUENCE: 103
aaagcagcgc ggccgccgcc tccgagggct gcagggagat cagcgtccag caaataagaa         60
gcaagtcctg gacccggagg aggaggagcg gccgagcatc tctctctgct ccgccgtgtc        120
ctttagatga gcactcccgg ccggagccgg aggtggatcc gcagagctgc ctctgggcgc        180
ctgaccccgc gctgacatca aacctgtga caggcgcatc acgcccggta cctgctcccg         240
gccgctgccc gtcctcccag cctctttgta tgccgcagac atggccagcc agcaggattc        300
gggcttcttt gagatcagta tcaaatattt actgaaatcc tggagtaata gtgagtaata        360
gaaaataacc ttttgtttg tttgtttgct ggatgttgca taaggctgga gacagaaaat        420
ctcaactgga cacatatgtt tgtgagccgc ggaagttttt cttttttct tttcttttct        480 tttctctttc tttctttctt                                                   500

<210> SEQ ID NO 104
<211> LENGTH: 500
<212> TYPE: DNA
<213> ORGANISM: homo sapiens

<400> SEQUENCE: 104
agggctgcag gcccagggcc agatcctgac ttgcccaccc gccggctgtg tgaccttcag         60
cgcgcgacta acctctctgt gcctatttcc tcgaggaaaa tgccgggaaa tagcagcgcc        120 tgccccctgta aagccctcag agcagagtgg accgcgctct ctgcaagcgc tggctgctgg        180
cgtccgtagc aagctaaatc gcgaagcatc tgaacgaacg aggaagccca acgaccatcc        240
cacaggccgc ggccagaggc agactccgga atgcaaatgg ccaaacaagc aggtccacct        300
gcgttcctaa ccaaaagatc gctaactgaa gaacgggcgc aagcacctgc gcatggcact        360
gcgggtctgg gggcggccgc ctgccagcgc cgggagccgc cttccacggc tacctctgca        420
cagcgcgcgg ctcgcgccgg ttgctgggca gaagctcgag cagcttcgag gatgtcgggc        480
ctgggggcgg ggccgcgagg                                                   500

<210> SEQ ID NO 105
<211> LENGTH: 500
<212> TYPE: DNA
<213> ORGANISM: homo sapiens

<400> SEQUENCE: 105
taagcagacg gcaggaatgt gtagggagct gcagtcataa tttatgacaa gccctgcagg         60
aaggggtctg cagtcacagta aatgcgcaat ttgtgacgct ctcgagccag gagcggcgc        120 aggctgggtc cgcagacgcc cggttcccac cgcggccggc ccggtctttg tcccgggaag        180
tcgcctgacc ccgccggcca ggaacagtgg cgttctcggc gcgtctggct gataaggcct        240
ttgtgacacc ggggacaggc tgtaaaaacg cagccagctt ttgtctgcac ctccgcgccg        300
ctggcaaggg cggggccggc gagtgtggaa aagtttgcgc ggattccgt tcacctctga        360
```

```
cccccgaagc agttggaggc aggtcgggga ccccccgcccc cgcccccgccc cgcctcgggc    420 cctgcgatca gcagtaatag cgattaattc cgactgtggc tccaagtccc atggccaagg    480
cgccctcctc ctgcaggtcc                                                500
```

<210> SEQ ID NO 106
<211> LENGTH: 500
<212> TYPE: DNA
<213> ORGANISM: homo sapiens

<400> SEQUENCE: 106

```
taagcagacg gcaggaatgt gtagggagct gcagtcataa tttatgacaa gccctgcagg     60
aaggggtctg cagtacagta aatgcgcaat ttgtgacgct ctcgagccag gagccggcgc    120
aggctgggtc cgcagacgcc cggttcccac cgcggccggc ccgtctttg tcccgggaag    180 tcgcctgacc ccgccggcca ggaacagtgg cgttctcggc gcgtctggct gataaggcct    240
ttgtgacacc ggggacaggc tgtaaaaacg cagccagctt ttgtctgcac ctccgcgccg    300
ctggcaaggg cggggccggc gagtgtggaa aagtttgcgc ggattcccgt tcacctctga    360
cccccgaagc agttggaggc aggtcgggga ccccccgcccc cgcccccgccc cgcctcgggc    420 cctgcgatca gcagtaatag cgattaattc cgactgtggc tccaagtccc atggccaagg    480
cgccctcctc ctgcaggtcc                                                500
```

<210> SEQ ID NO 107
<211> LENGTH: 500
<212> TYPE: DNA
<213> ORGANISM: homo sapiens

<400> SEQUENCE: 107

```
ttctccagcc ggtagaaaga gtcccggaca gggagcgcct ctccctcctc ctcagtctct     60
gggtaggaac actcggagaa ggtcctgctc atcctccgga ggcccttgaa atcaaaggtc    120
ttttcagagc tgcaggggga cggcaccacg ctggacagcc caggctggg gcagccctca    180 ctggccgccc actcgctccc agagccctcc cgcttctctc cacacatgct catcctgggc    240
gacgcctctc ggcgaccttc ccatgctgat atcttctccc ggatgccag gctgtgggcg    300 cgggtaccgg tacgggtcag caagacgccc cggggccag ctgctggccc cgggaatggc    360
gtgctctggg caaggggag gcaggcagcg acccctgcta catcctgggc tgcgccttgg    420
acactttcct tttgggcgtc tctcttgcac gccgaagggc ttctgtccaa ataaccgaag    480
ctggcggtct tgaagggaca                                                500
```

<210> SEQ ID NO 108
<211> LENGTH: 500
<212> TYPE: DNA
<213> ORGANISM: homo sapiens

<400> SEQUENCE: 108

```
taagtttttcc aagttaaaga aatgaccaga gccacgagaa cggtgccatc tggagggtgc     60
gtggaggcac gtggaggtgg cctctttctg tggggagcga gaggctcttc tcaccgtcag    120
ctctgggctg gcatctcagc ccctcgaggt gtgaaattgg atggcagccc ggccgggctc    180
cccgacctgc ccttctccct ttcctgggga cacctgagca gcgccacggt gatggcaggc    240
ttgtgcacgc gtcatgcaga tacatcctta ttttcttccc actcttcgtc gtccctgcc    300 cgcccaccct ccctctcacc atccagaagc cagaggcctg tggtccatgg gggagcgcca    360
```

```
caggcctcgg ggtgactttg gttgtgttct taaacgtccc ccaccctgcc ccagtgagtc    420
agaagacccc aagacacaca catggttaag gtcactccca ggagcgccgc cctgctggaa    480 ggggggggtgg gcggcaagca                                                500
```

```
<210> SEQ ID NO 109
<211> LENGTH: 500
<212> TYPE: DNA
<213> ORGANISM: homo sapiens

<400> SEQUENCE: 109
tggggcggca aagcgagact ccatctccaa aaaaaaaaaa ggaacatcat tggctgtcac     60
agaaactgaa aggacctcac tttatggctg tccacaccgt ccacacctcc tggagtcccg    120
agcgcggctg cgtgtcgtg tgcatttctc aggccctcgc caggtggtga ccagcgtgtc    180
ccaggagtgg acgacagggt ggtgtggccg gggcctgtgg gactcatctt ccctgggcag    240
tgctggggcc gccttggctg cgtcctcgtg tggatcactg tgtttttatg tgacacggct    300
ttgagcgtcg ttcacatgtt cctcgtggct cattgtgtcc acatcttgct ccttctgagg    360
aagcagaggg tgtgccgtgg cctcttgttt cacacacaga tgcgccatgc tgcccggcac    420
cttctcacgg gcacccgca gaatgccaga ggattcttag agaaagaaaa gagctgggca    480
cggtggctca cgcctgtaat                                                500
```

```
<210> SEQ ID NO 110
<211> LENGTH: 525
<212> TYPE: DNA
<213> ORGANISM: homo sapiens

<400> SEQUENCE: 110
accttgtgcc tgagcctgtt ctaggtgtta caggtagggc agagaacgca agacccagca     60
tctcggctct ccagcactgc cgccctagca cagggaggtg gataacaagc aggcaaacgc    120
acgatgaaga aaatgacaaa tgctgggtag gtaccaagta gagaatcaaa gcagggtgac    180
ttgattcagt gtgacaaggt ggctgcttta tctggagtgg tcactgtctg cgaaggacag    240
gtaaagcact gtgcagcaga cttgctgcac agagcgggtg acaattcagc tgaggcctga    300
ctgacaagaa gcacacagcc ctgtgaagat tagagaaaga gcattccaag cagaggcaac    360
aaaggcccta ccgtgagaac aagcttggca ggtggaaaaa cagtggaggg tggcagaaag    420
agagtcggct tggtgtcaga aagctcgggg cattgtccca gatctgttgc ttcctaggag    480
tgtgaacgat gagcaagtcc ctccatctct gatgattagt ttttt                    525
```

```
<210> SEQ ID NO 111
<211> LENGTH: 500
<212> TYPE: DNA
<213> ORGANISM: homo sapiens

<400> SEQUENCE: 111
actcgtggca ggattggaga aaccatttca cgtctgtgag tggcttcgag gtgagagcgc     60
tatgcgtgtg aggtgcttgc aagagctgcc acttcctggt acctcctcac agattttgct    120 ttcttttgc agccggcttc caggccgccc atgcctgctc accaggtgcc acctacaag    180 gctgtgtcgg cccggttccg gcccttcaca ttctcccaga gcacccccat tgggttggac    240
cgtgtgggac gccggcggca gatgagagca tccaacggtg agtctcagag tccctttcct    300
ttcagagctg ctatgggccc atctgaccgt ttccagctaa cctgaggcag caggttctgc    360
accttcgcgc ctcccttggg ccagggcgcg tttgtctggg agtgaggacg gctcatctca    420
```

```
ggagaatggt gcatcatttg ctgtctgggg tagatgctct gtgtgccagg ctggtggctc    480
taagtttgag aagtttgccc                                                500
```

<210> SEQ ID NO 112
<211> LENGTH: 500
<212> TYPE: DNA
<213> ORGANISM: homo sapiens

<400> SEQUENCE: 112

```
ttcccacaga ctaggcactt gtaaggccgc tcgcccgtgt gtgtgcgctg gtgcttggtc     60
aagtgggacg tcttgctgaa gcctttgcca cattcgggc aggtgtacgg cttgtcagcc    120
ccatgggaag cccgtcttcc tggtgggggg ccgcctcttg gctgatcagg cctgaccaag    180
cccctgactg gggctggcct ctgacctggg agcgggtggc caggcccctg gcatcgtgcc    240
gagagcactc ggtaccactc cattctcaac ggggcatcct ccctgccatc accgccgtcc    300
tccaactgga tcccaggtcc tgagacagag aaagcacgat ctctaggaac tcacagcaag    360
agggcaaggg aaatccttct aataggaaaa tgaaggcctc acagggctcc taaggttccc    420
ctacaaaaca tttagcaggg gctgggcact gtggctcacg cctataatcc cagcactttg    480
gaaggctgaa gtgggaggat                                                500
```

<210> SEQ ID NO 113
<211> LENGTH: 500
<212> TYPE: DNA
<213> ORGANISM: homo sapiens

<400> SEQUENCE: 113

```
ccctgccctg aagcttttcc tccagccgct gctcccacct gggctggcca gaggcctcca     60
ctgccatccc cctggtgccg cgaagcacgt ctgtctcccg ggtcctctgc tggcctctcg    120
catcccaaag ccatgctctg tctctgccgt cccagtggct cccacaaggc cctgaaggtc    180
gctgaccccc aggcgtgcag gaggaggcat tgtatagatg ggtgcaccca cgtgctggct    240
gaaggcctgc gctggacctt cgttccccgt cagtgactca agggcttgg tgtgggggta    300 acagcctctc agggtccctc tccctctggc atcgtgttct ccgctcaaca acaacaaagt    360
ccacgaatca atgagcaaaa gtgtcatcga agcaaggatt gcaggccatg tgcctgccat    420
gctcttctgg agaacaatac tgacaagaat gtgcctcact gctgtgtgcc aaggagggtt    480
gggttgggta gaaattctct                                                500
```

<210> SEQ ID NO 114
<211> LENGTH: 500
<212> TYPE: DNA
<213> ORGANISM: homo sapiens

<400> SEQUENCE: 114

```
acctatggag tccggggcct cacctagccc agctcttgtg aggctgggcc ccacactgtg     60
atcgtggatc gtccaacctg tgggaagttg gggtccaacg tgtgagaagg cagaagggg    120 aatggtagcc caggttcccc ttccccttc tgggtgctga ggggtaaact gaggccttca    180
gttggggaga gagccagaac cagggtccca cctagagtcc tgagatctag gcttggattt    240
caactctgcc gctgcatttc ggtgaggccc tgagatctct ggtcttcaat ttgcccttct    300
acactgagca cggagaggcg tggagtagac aagggccagg gcccttctac gctgtctggt    360
taagtcatta ggtgtctgca gggcttcaag ttgacaattg ccctctatc cagggactg    420
```

```
gctgagagat agggatacat agagacaaag agacacacac aaagagcgag caagagagaa    480
caagagatag tgagagacat                                                500

<210> SEQ ID NO 115
<211> LENGTH: 500
<212> TYPE: DNA
<213> ORGANISM: homo sapiens

<400> SEQUENCE: 115
atgtctctca ctatctcttg ttctctcttg ctcgctcttt gtgtgtgtct ctttgtctct    60
atgtatccct atctctcagc cagtcccctg gatagagggg caattgtcaa cttgaagccc    120
tgcagacacc taatgactta accagacagc gtagaagggc cctggccctt gtctactcca    180
cgcctctccg tgctcagtgt agaagggcaa attgaagacc agagatctca gggcctcacc    240
gaaatgcagc ggcagagttg aaatccaagc ctagatctca ggactctagg tgggaccctg    300
gttctggctc tctccccaac tgaaggcctc agtttacccc tcagcaccca gaaggggggaa   360 ggggaacctg ggctaccatt ccccttctg ccttctcaca cgttggaccc caacttccca    420
caggttggac gatccacgat cacagtgtgg ggcccagcct cacaagagct gggctaggtg    480
aggccccgga ctccataggt                                                500

<210> SEQ ID NO 116
<211> LENGTH: 281
<212> TYPE: DNA
<213> ORGANISM: homo sapiens

<400> SEQUENCE: 116
tgtctggggg tagaggacct agagggccgg gctgggcagc cggcttcctg cactgtctgt    60
tgggacgtcc ctttctgact gggtttctca gaagctgaat gggggatgtt tctgggacac    120
agattatgtt ttcatatcgg ggtctgcatc tgggccctgt tgtcacagcc cccgacttgc    180
ccagattttt ccgccattga cgtcatggcg gccggatgcg ccgggcttca tcgacaccac    240
ggaggaagag aagagggcag ataccccacc ccacaggttt c                        281

<210> SEQ ID NO 117
<211> LENGTH: 281
<212> TYPE: DNA
<213> ORGANISM: homo sapiens

<400> SEQUENCE: 117
gaaacctgtg gggtggggta tctgccctct tctcttcctc cgtggtgtcg atgaagcccg    60
gcgcatccgg ccgccatgac gtcaatggcg gaaaaatctg gcaagtcgg gggctgtgac    120 aacagggccc agatgcagac cccgatatga aaacataatc tgtgtcccag aaacatcccc    180
cattcagctt ctgagaaacc cagtcagaaa gggacgtccc aacagacagt gcaggaagcc    240
ggctgcccag cccggccctc taggtcctct acccccagac a                        281

<210> SEQ ID NO 118
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' FAM

<400> SEQUENCE: 118
```

```
aatgtatggt gaaatgtagt gttggg                                          26

<210> SEQ ID NO 119
<211> LENGTH: 27
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' HEX

<400> SEQUENCE: 119
aaaaatactc aacttccatc tacaatt                                         27

<210> SEQ ID NO 120
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 120
aaatacaaat cccacaaata aa                                              22

<210> SEQ ID NO 121
<211> LENGTH: 87
<212> TYPE: DNA
<213> ORGANISM: Artificial sequence
<220> FEATURE:
<223> OTHER INFORMATION: Exemplary Nucleic acid sequence for
      illustrating of a method of analyzing methylation status -
      bisulfite-conversion

<400> SEQUENCE: 121
cggaaccttg cctatgtagt gtgcggcgaa cgaggcttct tctctatagg gaagacccgc     60
cgggaggtag ggcgagccaa ttgccta                                         87

<210> SEQ ID NO 122
<211> LENGTH: 87
<212> TYPE: DNA
<213> ORGANISM: Artificial sequence
<220> FEATURE:
<223> OTHER INFORMATION: Exemplary Nucleic acid sequence for
      illustrating of a method of analyzing methylation status -
      bisulfite-conversion

<400> SEQUENCE: 122
tggaagtttg tttatgtagt gtgcggcgaa cgaggttttt tttatatagg gaagattcgt     60
cgggaggtag ggtgagttaa ttgttta                                         87

<210> SEQ ID NO 123
<211> LENGTH: 87
<212> TYPE: DNA
<213> ORGANISM: Artificial sequence
<220> FEATURE:
<223> OTHER INFORMATION: Exemplary Nucleic acid sequence for
      illustrating of a method of analyzing methylation status -
      bisulfite-conversion

<400> SEQUENCE: 123
accttcaaac aaatacatca cacgccgctt gctccaaaaa aaatatatcc cttctaagca     60
gccctccatc ccactcaatt aacaaat                                         87
```

<210> SEQ ID NO 124
<211> LENGTH: 26
<212> TYPE: DNA
<213> ORGANISM: Artificial sequence
<220> FEATURE:
<223> OTHER INFORMATION: Single strand DNA oligonucleotide

<400> SEQUENCE: 124
ggttagaagg tatagaaata attgtt                                    26

<210> SEQ ID NO 125
<211> LENGTH: 20
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' HEX

<400> SEQUENCE: 125
ttggggtttg ggatgtgagg                                           20

<210> SEQ ID NO 126
<211> LENGTH: 23
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' FAM

<400> SEQUENCE: 126
aaaaccaacc ttatcccacc tca                                       23

<210> SEQ ID NO 127
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 127
tcaccttctc caaactctaa aa                                        22

<210> SEQ ID NO 128
<211> LENGTH: 26
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' HEX

<400> SEQUENCE: 128
tattgatggg gttttttgatg ttttag                                   26

<210> SEQ ID NO 129
<211> LENGTH: 22
<212> TYPE: DNA
<213> ORGANISM: Artificial sequence
<220> FEATURE:
<223> OTHER INFORMATION: Single strand DNA oligonucleotide

```
<220> FEATURE:
<221> NAME/KEY: misc_feature
<222> LOCATION: (1)..(1)
<223> OTHER INFORMATION: 5' FAM

<400> SEQUENCE: 129
ataccacctt cacccacatc aa                                              22

<210> SEQ ID NO 130
<211> LENGTH: 30
<212> TYPE: DNA
<213> ORGANISM: Artificial sequence
<220> FEATURE:
<223> OTHER INFORMATION: Single strand DNA oligonucleotide
<220> FEATURE:
<221> NAME/KEY: misc_feature
<222> LOCATION: (1)..(1)
<223> OTHER INFORMATION: 5' HEX

<400> SEQUENCE: 130
ttaggtgatt tgtgatttgt gtatttatag                                      30

<210> SEQ ID NO 131
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 131
ggtattttga agaggtaggt tt                                              22

<210> SEQ ID NO 132
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 132
acctaaatac cccaaactca t                                               21

<210> SEQ ID NO 133
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 133
tgggtgttgt tattttgttg a                                               21

<210> SEQ ID NO 134
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 134
ctacaaaaat acacacccca a                                               21

<210> SEQ ID NO 135
<211> LENGTH: 500
<212> TYPE: DNA
<213> ORGANISM: homo sapiens
```

<400> SEQUENCE: 135

```
ctttctattt tgattttttc tctagtgaca agaaaaggaa gttagaggcc aaacaagaac      60
ccaaacagag caagaagttg aagaacagag agacaaagaa caaaaaagat atgaaactga     120
agcggaagaa atagtgaaga gaaactcggg catctgtgtt tgatcatggg aagatactct     180
cactaactga accctctctg gctggactgt aaaagcaac gagaggcccc ggcacacctg      240
gaagctggcc gcgaattcgg cctctgggcc tgtgtgtctg tgagctcaac ctggctaaag     300
gcagagtcac tcccaaatgg gtctctttag aacttgatgg ctgggcactg ccatctctag     360
aattgccacg agtctctctc ttcctgccca gtccagggcc ctcctttcct ataagttcat     420
attttgcttt gagccagctt tttagtctca ttcccacaca tgtggaagcc acgttgcctc     480
tcgaccgcct gaggccctta                                                 500
```

<210> SEQ ID NO 136
<211> LENGTH: 500
<212> TYPE: DNA
<213> ORGANISM: homo sapiens

<400> SEQUENCE: 136

```
tccaatggtg ctaatttaaa gattaaaagt gtgtttattc ctttccaagt gaaaagtggc      60
ttgtcttctt cagatcagaa gattaactgg cttttctctg aagccattta gggccattga     120
aacacaaatg ctatgtcaac acattttaaa ggagagatta tttatgagga tgcaatggtt     180
gtcaaaccta gctgatcatc cacatcacat cacatgggaa gctaaaaatt aaataaagac     240
agatgtcacc gtccgcacct ccatggagaa tctggagtgg gggctcagga ctcagatggt     300
cctgctgatg aatgatggtg agcctggctt gggcagctgg gatcccggag agctccgggc     360
agcattgctg cgtgtattcc tctgtcttga agatcactcc agacaagctt tcaaaccctg     420
ggcagtttac aaatgccttc cccgaggttc attcttatgt ctgctacact aacagctgc      480
acttctgtcc agctcatgta                                                 500
```

<210> SEQ ID NO 137
<211> LENGTH: 500
<212> TYPE: DNA
<213> ORGANISM: homo sapiens

<400> SEQUENCE: 137

```
cctgtctagt tcccgtggcc cagcgcagcc cagcacacag caagtgctcc atgaagccta      60
tgaacagttg tttctgctcc cttctcttcc accaggcgat gcccaggccc ccggccactg     120
tctccgccct cttggtaggc cctgtgggat caagtgtctc cgaggcggcg ggctgagacg     180
gatgggcctc ctggccgcac acctgagaac atgctggcaa aagcgtttgc ttaattaatt     240
gactttgagc gagggagccc gtccccgtgt aaacctagca gcaggctcgg tgcttgccgc     300
cgggatgctg cgaatgcaag gctagacttt aaataagggt gtgattattg tgtgaataat     360
tgaagaatgt tggggagctt gcagtcctcg gtgtaccgtc cctgccagc aggcctctgg      420
gccctgcccg tcacgggtac aactctgctg ccatcctctc agctgggaca gtggggggact    480
ttcagaccta agcgttggag                                                 500
```

<210> SEQ ID NO 138
<211> LENGTH: 500
<212> TYPE: DNA
<213> ORGANISM: homo sapiens

<400> SEQUENCE: 138

```
aggctggttg tggcccatgc tcctgaggtc aggggctagt taatgtggta gaaaatccag    60
ttaggctgtc aggggaagt ttgaaaacaa tgtttatatt taatttccag aggaggctga    120
cggaacgccc aaatggaatg gcgctgttca cccatctggc tccctgagtg ttatgatgtt   180
tttcacagta cgttaacggg gagatgaatt cgccgactct gtcttgcaga gggcgtgtgc   240
gtcatcccac gttgcctggg aaaacaagca ttaacaagtg tgagcgcggg tctccgtgga   300
aatggtacag aagggggccc acggcgggat cattagtgtt actttgcccc tggaggaaga   360
aggccctgcg tcatttccca tccagagtgg gaagggaga gagactgaga gataaaaagg    420
aaaataaaca gccctttttt atttatttat ttttttttga cggagtttt tgctcttgtt     480 gcccaggctg gagtgcagtg                                                500

<210> SEQ ID NO 139
<211> LENGTH: 500
<212> TYPE: DNA
<213> ORGANISM: homo sapiens

<400> SEQUENCE: 139
acgctcactc atgatgagct tgtactcgct gtacacagcg tcccgctcct ccctgtattt    60
ctccgactcc tttgctgtct tcacctgcgt ggttctcagc tcggtcagct ctgactgcag   120
cagctccatc tcccactgca ggtccttgtt ctgcgccgtg gccttgttca gctcatggtg   180
gatcgcctca aacctggcaa gagaggtggc gagatgtggg aagggcgggg gccctgcccg   240
gtcagtggcc ggctgcgctg ctgcctcccg ccagctctac tgtgctggac agtcaagcgt   300
gaagtttcaa gtgaagtcac tctctccacc cccaggagag aaaagtcatg gagtaccagt   360
gcccccggac ctggaatttt tctcagcccct ttacaaatgc caggagttga actgaggact   420
tcatgccctc cactccacta gaaacaacag catatttctc ccacagtcaa gccacattaa   480 tttttttaaaa taataaaaac                                              500

<210> SEQ ID NO 140
<211> LENGTH: 500
<212> TYPE: DNA
<213> ORGANISM: homo sapiens

<400> SEQUENCE: 140
cctcccgagt agctgggact acaggcgccc gccactgcgc ccggctaatt ttttttgtatt   60 tttagtagag acggggtttc accatggtct cgatctcctg acctcgtgat ccgcctgcct   120
cggcctccca agtgctggc gtgagccacc gcgcccggcc tcatttttttt gttttattta   180 tcagggagca acggctccat tctcccctaa ggctgacatt tttgttgaag gctgagcacg   240
catgtcttcc gtgcttgtgg caaaaggccc tttcctggct ggctccagaa tcctcaccag   300
ttaattggga aaaatttga gttaggcatc acaatttcag ccgagctggg caaacaacga   360
gtacacctgt cactcgagcc agtgtccaaa actcagcccc atggatcaca gctgtagcgt   420
tatttcagca tgagcaattc agtatttaat gttccttaga aaaaaagtaa atcattccaa   480
gctgctactg ttcacctatt                                               500

<210> SEQ ID NO 141
<211> LENGTH: 500
<212> TYPE: DNA
<213> ORGANISM: homo sapiens

<400> SEQUENCE: 141
```

```
cttggctctc ttattgccta attacacgtg cagcgttgac aaatggcatg cccctccgtg    60
ccgtcagcac actgacgttg tcaccattac taacggctgg ctggcgctgc ttccagcaag   120
gtgagcagct gtggccagtg gctatgcgtt tgggtcatgg attccaccat gccttgcatg   180
tgtgtttggt cacatgttct gccgtgtctt gcagagctgc agaaactgga gggcagcagt   240
ggacctgtgc ggacgtctcc tcacagccca cggccagggc tacggcaaga gcgggctgct   300
caccagccac acgacagatt cactgcaggt gagaacacct ttcaggtgct ggagtttaac   360
ctggcttatc acagtctggg gacatggaca ggaccatggc ctttcatgcc aataacaaaa   420
agtatgtttt catatcctgc ttctttctct cctaattata ttgtatatac tatactgggg   480
cactggaatt ctcacttcgg                                               500
```

<210> SEQ ID NO 142
<211> LENGTH: 500
<212> TYPE: DNA
<213> ORGANISM: homo sapiens

<400> SEQUENCE: 142

```
atgcaattct actattaata atttccgtat agcagctcga acaaagcact gacaaagtgt    60
caccaaatgc atttcttgct tcacttcttt catgaacaga taaggctaat tcacttgctt   120
acgctaatta gagcctgtta cacgcgggcc cctgaacagc cttgatgtgc agaggcccct   180
gggtaagcca gggcgccagt gacaggtggc cggaccccgc aggagtggaa cctgcccatc   240
tgcgcttgac gaaaatgcct ccaaaacaaa ccagacgccg ccccggcaga ggaaactgag   300
aatgaggaga aacggtctct tttcccgatg aaagggttct ctgtaatggg caccaatgac   360
caggttttga agggcaatac tgtgggtcag cgagggtttc cggggccccg tgggaggcgc   420
cctgctgtca gacgcgtttc tgtcctcctc agcccccaac ctgcgcctgg tgctctcggc   480
caaccttgct cagagcttga                                               500
```

<210> SEQ ID NO 143
<211> LENGTH: 500
<212> TYPE: DNA
<213> ORGANISM: homo sapiens

<400> SEQUENCE: 143

```
caccctgagg cccctcgttg tgtggggtag tgggcaatgc ccaggtctgg tgtcagacag    60
gcaaggttca cacctcaatg ctgccatttc cagttatgtg accttgggaa ggttacctgc   120
ttttcctgag cctttattat taaaaattta ttatgaaatt tcatttcaaa atgcactaac   180
atggtagcca ctaagcacac gtggctattg aacgcttgaa acgtgatgag tctgcattga   240
gatgtgccgc gagtataaca cacctggatt tcctccctcc ccaggtgcaa cagtgacccg   300
tgacgcagta gggagggctg ttttccatgc ccagtgaggc ctgctcagct cccattaggc   360
ctttatggat ggcctgcctc ccagctggta cctggtcccg tcacagtccc aggactctag   420
acctcgaggc agccaggtgg gtgctacaga tggtgacctc tcggtggcac agcctggcgc   480
tgcagcagaa tgcagggttg                                               500
```

<210> SEQ ID NO 144
<211> LENGTH: 500
<212> TYPE: DNA
<213> ORGANISM: homo sapiens

<400> SEQUENCE: 144

```
ctgaagaagc tgtgaaaata gcagattgct tatccaagca caacattatg aggcgtggcg    60
```

| | | |
|---|---|---|
| tgtctaatca cgaacccact agaacatgag aaagaagaaa ttgaacaaga ctgtaatgag | 120 | |
| ttgtttggaa tggaagccca taagaaacta aaaccaaaaa atagtcagca tttaaatgca | 180 | |
| gagtgcagaa ggacatttcg gggagcccag gtcctcagag cgtgggggtg ttagctgccc | 240 | |
| tgtgcaaggc ggtcctttat tggaaatcgc ctcagagagc attgctgagt gtggcttctt | 300 | |
| gcaactacac ctgagaacga cattcactct gcttcattga aaacaatcta tcccgtgtgt | 360 | |
| ggaagaagca tgccttgctg gggtcagggc cagggacaaa gctcagaggc catgctgagt | 420 | |
| tttcatcaaa cacctgctga gcagctggca cgtgccagga cacggtctag gctgaaggct | 480 | |
| gccatcgtag tgcagaatag | 500 | |

<210> SEQ ID NO 145
<211> LENGTH: 500
<212> TYPE: DNA
<213> ORGANISM: homo sapiens

<400> SEQUENCE: 145

| | | |
|---|---|---|
| tgtggctctt taacaagcca tcgctttatg aagcaaggtt aacaatttca cttgattcag | 60 | |
| tggaatatta taaactctct ggggcccatt tgaggacttc tacttcaggc gcaaggtgac | 120 | |
| gattcagcac ttttcacatt atttagagaa taaaattaac cctcgcaggc ccgggctgcc | 180 | |
| gcctgtcccc gctggatctg gccggctcag cgctttccca tatataatta caagctgcta | 240 | |
| tccatcatgc gggcgccgcg gcgcggacac acggaaaggc agcagtaagc acttccacta | 300 | |
| atagaagcag gacctaaata tcactttgat atttcattt aaatcgaaac attttacaat | 360 | |
| aatcagccat ggcctccatg gggatcctgc cactgccccc acagggtctg ggctgcccc | 420 | |
| agccaggccc tacctcccg gaggggattg cctgccaggt ttcaggttgg ggagcccggc | 480 | |
| ctggccaacc cttggcccgg | 500 | |

<210> SEQ ID NO 146
<211> LENGTH: 500
<212> TYPE: DNA
<213> ORGANISM: homo sapiens

<400> SEQUENCE: 146

| | | |
|---|---|---|
| tttggccggg tgggccatga atacgagata tgggtagata aggaaatgga cacactgatg | 60 | |
| tcttccagag tcccccactg caacagggcg gtgcttcaa tgcagctctg ggtggtagtg | 120 | |
| gggggctcct ctgagatcct ctctagggaa gagagaggag ttgaggcaga ggaaaaagtt | 180 | |
| cattgctctt ctcctcttag tcagccaagg tgttctctgc ctacttagcg gtcgctccag | 240 | |
| aatcaagctc ggatgatccc gccttccatg tcgttgtgtc ccctcacagt atttatttta | 300 | |
| aacattcatt tcctgagcaa atgggatcat tagcacttat ggtccattgc tgcggcaatt | 360 | |
| agatatcctt gcttaatagc ccttgagcag aatgcatcgt caatgcgtgc tgggagggag | 420 | |
| tagagttaca tctagattga gttttcagtg tccgttgttc aacccaccat gcaccctggt | 480 | |
| agcattagct tcgtcaagcc | 500 | |

<210> SEQ ID NO 147
<211> LENGTH: 500
<212> TYPE: DNA
<213> ORGANISM: homo sapiens

<400> SEQUENCE: 147

| | | |
|---|---|---|
| ggcctctaat tctgtaaaat cgcggtaata gcatccgctt ctctgagctg ttagaggtgt | 60 | |

| | |
|---|---|
| aacaggtaaa cccatgtaag gtgcttagga cagggctggt gctggctaag tgccgttaat | 120 |
| atcgtcagca tcattacctg cgttattgta gcactgatcg ccatgtcagc tgccttcagg | 180 |
| gtctggcagg taaagtagag gggccaggta gagatcctgc tgacctggca agcacatgtt | 240 |
| ccctccagtc ggggcgttga ccgctcagca gcaggtctag tgtcacccag tctttctagt | 300 |
| tctcaggaga agttgagggt ctggattttt agaggatagc tcttgtttcc tttactttttt | 360 |
| tttttgagac agagtctcac tgtgtcactc aggctggagt gcagtggcac aatctcggct | 420 |
| cactgcacct cctcctcctg ggttcaagtg attctcccgc cgcagcctcc caagtagctg | 480 |
| ggattacagg catgcgccac | 500 |

<210> SEQ ID NO 148
<211> LENGTH: 500
<212> TYPE: DNA
<213> ORGANISM: homo sapiens

<400> SEQUENCE: 148

| | |
|---|---|
| taatccttt ggaccgggat aagagaatat ttgaaatttc ttattaaagc aataacttcc | 60 |
| ttaatagggc tttagtcttt ttgctttttt ttttcttta agagctgatc atctgaattc | 120 |
| ctagtacttg caagtaaatt ttttttttt tccttttctg tccacctacc attaggtggt | 180 |
| tcctagatcc tggcaaattg tctatggtta aatgatgctt ttaatttctg tgtcaacaca | 240 |
| gaccctcttc gttggtgtct ccaaattagt attctcttcc tctagtgtgt cattacagtc | 300 |
| ccttttggct tttgtttctt cctcatggaa taaatgtggg tgctcaattc gtcccctacg | 360 |
| tacaaaatgc tggatccggg attccagtcc ttggcattta ggacggtcca tgagggggctt | 420 |
| atatgtgcgc atcttcactc cttctacaaa ggcactggtc tgctttatga cagagggctt | 480 |
| aacatttccc cattctgtca | 500 |

<210> SEQ ID NO 149
<211> LENGTH: 500
<212> TYPE: DNA
<213> ORGANISM: homo sapiens

<400> SEQUENCE: 149

| | |
|---|---|
| ttcccaggcc ccgcccaagg tgcacacagg accctcagc accctgccca cctccactgg | 60 |
| ctctggaact ggctgctagg ttcctgatct taaaaaaaaa aaaaaataca agtcgctgcc | 120 |
| tcggggcccc atctgctccc cgaccccaga gaggcccacc cagatggagg gagcgggtgc | 180 |
| ccaggtctcg tggggcggag ggtctggcca cggctccacg cccctgacgt ggaggctgtg | 240 |
| aacaggaggc ggcccctccg aggcaggcat ttgagtgtgc tcagcggagc tgttgcagaa | 300 |
| ggctgcagca agcatcttcc attaacgtta cgaccgtgaa atatgacaat aaaatgatag | 360 |
| ccgtatggtc gcaaatttgc agcccgccga gctgcgtggg gtttatcgtc actcaaacgc | 420 |
| gcggagagct gtaaaatgtt tacagaaagg gtcgtttgca gccataaaat cctctttcct | 480 |
| ctcctaaaca aggctgagtg | 500 |

<210> SEQ ID NO 150
<211> LENGTH: 500
<212> TYPE: DNA
<213> ORGANISM: homo sapiens

<400> SEQUENCE: 150

| | |
|---|---|
| catgatatta aatagaaatc aggagaaatt aaacttaacc ctttccctgg ccagcccctc | 60 |
| ctgccacacg gattctggca taagccggcg ggcacagggg acagccaggg atggctggac | 120 |

```
acagctgagg atggccgagg ccggcctgca gctccccaac ggcctcctcc gggtcaggat    180
gagaggagag gttgccagct ttgatgccag ccgctcctgc ctcccccacc tgcctctgtg    240
cctacagccc gcttctgcct caagatcaca cagcgggctt gtgaggccag gggtctccgc    300
tgctgctcaa ggagatggca aaggtctgtt tcaggtaact cctctgacgg ccacaacgat    360
gtcttcagac gtcaaaggtc tgtctcaggt aactcctctg acggccacaa cgatgtcttc    420
agacgtcaaa ggtctgtctc aggtaactcc tctgacggcc acaatgatct ctgcagatgc    480
tctgactcca cgtgccctcg                                                500
```

<210> SEQ ID NO 151
<211> LENGTH: 500
<212> TYPE: DNA
<213> ORGANISM: homo sapiens

<400> SEQUENCE: 151

```
cgtcagcatg aatagtgcta aggagtcaag ccaagacttg cttcagaaga gagctgatgt     60
gcggaccttc tgcatttcca cgcggggatc cagtgcttgg gtctaaaccc cagcgccctg    120
ccacctcggc caggaagctg cgggaggatg gtggcaggca tagcccgtcc tagccttgaa    180 actgggggc ctatgtctct ggcttcgtta caaacgaaac gtttctcgcc ttcggacact     240
ccaccctggc ggtggtaccc aaccttcagt ctccactctg cgcctggccc tccagcgacc    300
tcctcacatc ctccaggaca ctgcattctc aaggactagg taggaattgg gaggaaaaga    360
ggccagtcat ccccaaagat tccaatgtta aagagtgatc cccttttat ctcatgtaaa     420 tattatgact cggaagagag ttgaatattt ccctattgag aatgttagta tctactattg    480
gaggcggggt tgccaaagag                                                500
```

<210> SEQ ID NO 152
<211> LENGTH: 500
<212> TYPE: DNA
<213> ORGANISM: homo sapiens

<400> SEQUENCE: 152

```
agaaagggag ggaggaaagg aaagagagct tgaggtatgt ctttgagttg cttttgggct     60
gcctggtggc accttgttct agttggggac ctgatcaggt ctgtggcctg atggcatggc    120
tcctcagtga aagcaatgat agggagctca tgtgaacttg tctatttcca ctaaaccctt    180
ttcatgtact tcatgtgctt tcatgtatag accaacagca aagcctttac tgccaagact    240
tcctgtgtgc ggcgccgcta ccgtgagttc gtgtggctga gaaagcagct acagagaaat    300
gctggtttgg tgtgagtttg ctcttgcttc cttcttgggt ctgtgactgg cttttgggt     360 gcttatgtag gaactggagt tgacaatgaa gagaacttgc aacataccag gcactaagga    420
aattgggaaa tatgttgttt cttttttgt ttttgggtt tttttttttt tttgatgtag      480
ggtcttgctt tgttacagag                                                500
```

<210> SEQ ID NO 153
<211> LENGTH: 501
<212> TYPE: DNA
<213> ORGANISM: homo sapiens

<400> SEQUENCE: 153

```
ttggcgagta atccaggac ccccttaagc ctcaggctta tctcctggaa acttatcaaa      60
ttggccagag tggccggaga actgtggaag tggttccttc agtgctgttt tccaagaagc    120
```

```
agagcgtggg ctctggaatc gcagagatgt gtgagcaaac cccaaccctc cacttcctgc    180
cccacgtgga gggcagcctc cctgtgtgtt ccttatctag aacacaggaa tcttgatgtc    240
ccctccagag cacgtgagga ttaaatgcag ttacatatga cgcacccagc gcagcacctg    300
gcaccaagta cgcatccgtt agtcctcttc ctacatttcc tcaccttca ctttaagaaa     360 acagggctgc ccatgaccct ggagatcagg ctcggattaa gcttccagag tggctcctgc    420
tgctgctgat gatcccagca gggtgaggag atgctggatg gagagcagtt atctgttgca    480
cttaggcaag atcggaggaa a                                              501
```

<210> SEQ ID NO 154
<211> LENGTH: 501
<212> TYPE: DNA
<213> ORGANISM: homo sapiens

<400> SEQUENCE: 154

```
tctgctctca gaggtggagg gttagaagac cgaattgcct tgtttaagag cattaggttg    60
atgacgagcc ccaggcctca taaaggaaga gagagatcca cttagggctc ttagcatcat    120
tctatgtatt tggacatatt tcctaattta ggtctgaagt acttggcatt tgatggcaga    180
ttgtattaag cggcacacgg cgtgcatcct aatcagggag ctgtgagtga agtaatccag    240
gaggctggaa tgcgtgtgac aaggacgctt gcttggcgct gctgcctcag cttacatcac    300
gctgaaaaat cattgctaac gtctcttatg ataattattc cccatacacg gacgtgaaga   360
gactctggat tggttgctca cactcatcac gagttgaaat atctgtctgg gagagcctta    420
ggaatcagaa atgcagtgcg catagattgt ggccacattc tcccatacct ccacccgaac    480
aggaaatcca tctttccttt t                                              501
```

<210> SEQ ID NO 155
<211> LENGTH: 501
<212> TYPE: DNA
<213> ORGANISM: homo sapiens

<400> SEQUENCE: 155

```
ggagataagc tggagggga aggcagaggc tagagctggt ctctagtttt ttagacctta     60
tcttctgaag gacagataag tgcctctgcc tccatcagct tccaccgaga cgaagtgatg    120
caaaccagac cgtgcagcca actcctgcgt caggttccat aggaatcctt tccccgccag    180
tggaggaggc tctcccgtct tttggaaatg atgtgcagga gacagagctg attctcattt    240
cttccatgga cacggctaag tgcgggctgg tgtgtgagaa agggttcggg gcgcgtggtt    300
ggtggaagtt agctcctggc tgttctgcct tgcagtccca ggcaactcag accttccctg    360
gctgctactc acacctacgc tttcctacgc aggctctgat cttcttttc agccctagaa     420 tcccagaata gcagctaatg tgtattgagc ccttttttct ttttcttttt aagacagggt    480
ctcactttgt cacccaagct g                                              501
```

<210> SEQ ID NO 156
<211> LENGTH: 501
<212> TYPE: DNA
<213> ORGANISM: homo sapiens

<400> SEQUENCE: 156

```
caaccaggca gctattaaat agtgaagtta tatgtcaggg agcagcacct cctcacctga    60
ggatggggct ggggtgtgtg tgcatgtggc agttcctgga tcacacagtg tggctttcaa    120
aggagctgcc aaaactgtttt ccagagtggc tgtgccattc cctgtcctca ccagcaccgg   180
```

| | |
|---|---|
| atgagtgacc cggtttctct gtgtccttgc cgccttcaat gttgtcacca gtttttattg | 240 |
| tagtcattct gacgggtgtg cagtgatatc ttatcgtggc ttcagtttgc gtttctgtga | 300 |
| tggccggttg tgttgaacgt tgttttgtgt gcttgtttgc catctgcttg tcctctttgg | 360 |
| tgatgtgtcc tgttgacagt ctcggagcaa aagcattccg ccttgatgta taatgctagc | 420 |
| tgcagcttgt tcagggagtc tctgtcaggg tgaggaagtt cttctagtc ttagtttgct | 480 |
| gagaggtttt atcatgaatg g | 501 |

<210> SEQ ID NO 157
<211> LENGTH: 501
<212> TYPE: DNA
<213> ORGANISM: homo sapiens

<400> SEQUENCE: 157

| | |
|---|---|
| acgaggtctt tctcacctcg gtatcgctgg cacttacgtg ctgggggctc aatacacgtt | 60 |
| cctggaagga acagagggaa ggaggagctt ttcatttctc tgctatcttg actttctcaa | 120 |
| cacttcaacg cgttgatctc attcgattct tacaagtgga gggagaaagg atggtttgtc | 180 |
| atcacccctta ctttatggat aaggaaacca agatagcatg gcttggcaat ttatccagag | 240 |
| aagcaaaatg accgacaaca acgcacggtg aaacgcagtg ttgggaatcg cagatggaag | 300 |
| ccgagcattt cctctacctg tgggacctgc acttttccta atgctctttc ccatgtgttc | 360 |
| tctgcaggtc ctcaggcaaa tcctgtggag gagaaagggc aaagtcatcc cagtgtctcg | 420 |
| tttttgaggg aacttgtggc tgccatgtgg acagtaccag gggatatgtc tcagcagccg | 480 |
| gccgggaact cttggctgca g | 501 |

<210> SEQ ID NO 158
<211> LENGTH: 500
<212> TYPE: DNA
<213> ORGANISM: homo sapiens

<400> SEQUENCE: 158

| | |
|---|---|
| cttcaaccag gatgctgaac atcagcgcca ccgcaaaaat ggtgttccca aatgctccca | 60 |
| caacatctgc ccgaagaaag ccgtaagtgc tcttcttgtg ctgttttatg ttactggccc | 120 |
| ttacaccaaa aaaacctatg atcatggaca caaagtggga aaggacggca aaagcatcgg | 180 |
| aggccaagga gagggagttg ccaacgtaag cgatcactag ttccatcaca aagaggagga | 240 |
| tgctaacgac gcacatgagg attaaacgga agcttcttcc ggagtatcgc cccatggcgt | 300 |
| ctcggtgccc tggcagttcc tctccctttc ttgggaaggc tgagctgcta gggaagcagc | 360 |
| tatagattca gtgattacaa ctcctgggta actcttccct tcagccctcc ggcgcttgtc | 420 |
| atatttggaa atcacctttt ataggttgct ataaagccat aaaacagttt aaagggcaat | 480 |
| taagcaagag atgtcacatg | 500 |

<210> SEQ ID NO 159
<211> LENGTH: 500
<212> TYPE: DNA
<213> ORGANISM: homo sapiens

<400> SEQUENCE: 159

| | |
|---|---|
| tgctcgtagc cacaaacgct gggccctgcg gggcaggtcc acgggacaga cagacatacc | 60 |
| aatactctgc tgctcggact caaccctgtg tcccagagga ctgaagtggc aggagcaaca | 120 |
| cagaaggggg ccggggtggg gggcactcc ctaaaaacct ggcacggaga cacccaggga | 180 |

| | |
|---|---|
| aggacgcgag gggagcaggg agcgcgggag cctcatgcag gtgtgcgttt cacacggggg | 240 |
| ggccaaggtc gcccttcccg aggcagccct gccttctccc ccggccctcg cacccagcg | 300 |
| cgagtggagg gcatgcggtg cgcagggcag ctgtggaggg cagagacagc caagacctcc | 360 |
| cctgcgaggc aggcccgtgg gcacagtttt aggacacagc ctggtccgtt ctgacagcca | 420 |
| caggcattta gtctggagac tgcccaggca tcccacgatg ggtcagaggc ccacttacc | 480 |
| caaaaaagcc tacctgcctc | 500 |

<210> SEQ ID NO 160
<211> LENGTH: 500
<212> TYPE: DNA
<213> ORGANISM: homo sapiens

<400> SEQUENCE: 160

| | |
|---|---|
| aggagaccca catattattg cacctttggg attcccctc ctaattcgga ggcaatcacc | 60 |
| attattcaca ttttatgaaa taagaagcac aagctcagag ggggttcaga gaagtttaaa | 120 |
| catgtacaca gtggttaaat ggttaggtta agatgaccat tgaacattta agtttaatga | 180 |
| tttataaaac catatagaca gcgtgggcat gtgatctgtg agccgtggtc cccacggaag | 240 |
| cggtgagaac gcacctggcc ggctcagcca cacggcacgg tggcctaggc cctgctgcgg | 300 |
| gctctggatc cagcggtcac ggtttcactg agagggcgcc tcccaggggc tgctccggcc | 360 |
| cagggcaggg cattgcaggg gtgatggac agccctgctt ttgagaggcg cggcactctg | 420 |
| ccaagggcca cccctggtag ccctgcccag cctccctggg agcacacagc tgtctaggat | 480 |
| gcttctgggc atcctttccc | 500 |

<210> SEQ ID NO 161
<211> LENGTH: 500
<212> TYPE: DNA
<213> ORGANISM: homo sapiens

<400> SEQUENCE: 161

| | |
|---|---|
| acaacaaaaa agtgaagctt aggatgcatt ttataaactc tgaccagaac acctgtgttt | 60 |
| ctctgtttct aggtttatga actgacgtta catcatacac agcaccaaga ccacaatgtt | 120 |
| gtgaccggag ccctggagct gttgcagcag ctcttcagaa cgcctccacc cgagcttctg | 180 |
| caaaccctga ccgcagtcgg gggcattggg cagctcaccg ctgctaagga ggagtctggt | 240 |
| ggccgaagcc gtagtgggag tattgtggaa cttataggca agttattagc aaggtctact | 300 |
| cttacaatta actttgcagt aatactagtt acactctatt gattatgggc ctgccctgtg | 360 |
| ctaagcagtc tgcattccat cttccttgcc aaaacttata atacaaattt catctttatt | 420 |
| ttataaatag gggagttggg ctgggtgtgg tggctcacgc ctgtaatttc agcactttgg | 480 |
| aaggatcgct tcagcccagg | 500 |

<210> SEQ ID NO 162
<211> LENGTH: 500
<212> TYPE: DNA
<213> ORGANISM: homo sapiens

<400> SEQUENCE: 162

| | |
|---|---|
| acagattccc cctggaggcc caaacacagg gaccctaggg ctgcctggca gggagggcc | 60 |
| gccgttccaa ggatgcgcac tcaccaccag ctggggcaca ggcagcgacc tgccttcctg | 120 |
| gctcagcgac acgtaggtga agaaggcact ggcggcccgg tagcgcttct gagagctgtc | 180 |
| cacaacaggg tcggcgtcca ccaacacctc gatctccatg gacttattgc tcgtgaaggt | 240 |

| | |
|---|---|
| catgcgtccc gagatggtga tgacgcagcc tgtggagaag ggagggcggg ggtcagggcg | 300 |
| gcctccaccc cacggctggg cggggacac tggcgtttct gtggtcagca ggcagacact | 360 |
| tggttagggg aagcagtggc ttggctgact accagatgtt caaataacag aatattagaa | 420 |
| tgtgtcgtta gttgcccatg aatgtttatc tttctagtga gcaggtttat ctacgctaaa | 480 |
| attcagcact gaaggatttt | 500 |

<210> SEQ ID NO 163
<211> LENGTH: 500
<212> TYPE: DNA
<213> ORGANISM: homo sapiens

<400> SEQUENCE: 163

| | |
|---|---|
| gtggtactca gcgctccctt cactgaccat ttaaatgtaa agcaatgttt gtcctcgctg | 60 |
| tcagtcgcaa cacttgatta ctgtagatgt cagagcatta agaattcctg ccgatggaca | 120 |
| ggagcccttt cgctcgcgag cccgtgcgtg cagcagccag agcctgtgaa cttcgtggaa | 180 |
| tgctgtcgac gtgcggatca tcatctttac gttgctatta aacagctcc tggcactaca | 240 |
| aagtagctgc gttggagcca acaggaatcc ataaatcagc agcaggttaa agattgttga | 300 |
| acttctctgt gagggatctg gaaaatacat cactgacttc caccagccac agagctgcag | 360 |
| ggtgggagcc gagcgggttc ctctgagcag cacaagcgtc ctgcgcttcg acacacaatg | 420 |
| agcctcagta caggggcgtg tgggggctcc tgaggggca gctccatctg cagctcgctt | 480 |
| tccaatagcg cgaggctgtg | 500 |

<210> SEQ ID NO 164
<211> LENGTH: 500
<212> TYPE: DNA
<213> ORGANISM: homo sapiens

<400> SEQUENCE: 164

| | |
|---|---|
| ggcccgccgc ccccagcccc gcctgccgcc cctccccgcc tgcctggact gcgcggcgcc | 60 |
| gtgaggggga ttcggcccag ctcgtcccgg cctccaccaa gccagcccg aagcccgcca | 120 |
| gccaccctgc cggactcggg cgcgacctgc tggcgcgcgc cggatgtttc tgtgacacac | 180 |
| aatcagcgcg gaccgcagcg cggcccagcc ccgggcaccc gcctcggacg ctcgggcgcc | 240 |
| aggaggcttc gctggagggg ctgggccaag gagattaaga agaaaacgac tttctgcagg | 300 |
| aggaagagcc cgctgccgaa tccctgggaa aaattctttt ccccagtgc cagccggact | 360 |
| gccctcgcct tccgggtgtg ccctgtccca gaagatggaa tggggggtgtg ggggtccggc | 420 |
| tctaggaacg ggctttgggg gcgtcaggtc tttccaaggt tgggacccaa ggatcggggg | 480 |
| gcccagcagc ccgcaccgat | 500 |

<210> SEQ ID NO 165
<211> LENGTH: 500
<212> TYPE: DNA
<213> ORGANISM: homo sapiens

<400> SEQUENCE: 165

| | |
|---|---|
| agacaagtcc gccgagtgag tgtctgagga tggagacgcg aagggaatgg ggaggggcgg | 60 |
| gctctgttgc cgcttaccct ggagctgggg ctccagtttt ccagtcgaag ttctcctctc | 120 |
| tgcctacatc tcggattctg ggtctcagat gcaatcgcgc acccaaattg catcctgtga | 180 |
| acagaaaaag tctcaaacat gcgtacaaag aatattcaga agcagaagca atttctgaag | 240 |

| | |
|---|---|
| agcgaggccc gggactgagt tggcgagact cccagttcga gtgagcgaag ccagggtgga | 300 |
| gggctccgga ccgagattcc tgaaagcctc cctgacaccg gatcctgagc gcaggacggg | 360 |
| cccagccact tgggggcgcc gctggcccca aagtaccggg agcttaccct ccgctgacca | 420 |
| ggattcaccc tggctggcag agactaccct acgctccgct cacccggcca ccccgccccg | 480 |
| ctctgcgctg accctccgtt | 500 |

<210> SEQ ID NO 166
<211> LENGTH: 500
<212> TYPE: DNA
<213> ORGANISM: homo sapiens

<400> SEQUENCE: 166

| | |
|---|---|
| cagaaacaaa gtcaataaag tgaaaataaa taaaaatcct tgaacaaatc cgaaaaggct | 60 |
| tggagtcctc gcccagatct ctctcccctg cgagcccttt ttatttgaga aggaaaaaga | 120 |
| gaaaagagaa tcgtttaagg aacccggcg cccagccagg ctccagtggc ccgaacgggg | 180 |
| cggcgagggc ggcgagggcg ccgaggtccg gcccatccca gtcctgtggg gctggccggg | 240 |
| cagagacccc ggacccaggc ccaggcctaa cctgctaaat gtccccggac ggttctggtc | 300 |
| tcctcggcca ctttcagtgc gtcggttcgt tttgattctt tttcttttgt gcacataaga | 360 |
| aataaataat aataaataat aaagaataaa attttgtatg tcactcccca tggctccaag | 420 |
| tttgtctctc cctgtctctg agatgggcct cccctccatt ggtcgatccc caaaagcccc | 480 |
| ttcaatgatc ctcccaacta | 500 |

<210> SEQ ID NO 167
<211> LENGTH: 500
<212> TYPE: DNA
<213> ORGANISM: homo sapiens

<400> SEQUENCE: 167

| | |
|---|---|
| cctccgccgc gcccctccg cactcgcacg gccccacccg caggcgcccc ccgtgcggag | 60 |
| gaagcggatc tgccaggatc attttttgttg tgtcggagga tgaggttttg gctgaggact | 120 |
| gaagagatgg ccttggaaga aatggtgcag agattaaatg cggtttccaa gcacacgggt | 180 |
| aggaggagct gctggccgtc agtgatctgt gcttaagctt gacatcatgg gctgaaatgt | 240 |
| ggggaaatgc gtctgatttt tgtaagccgc cctcgtgttc cttttctagcc gtggtagctg | 300 |
| tgacatgggg ggcactggtt ggcagctggt gtgttttcag aggctgtcgg cgatcgtatg | 360 |
| ctgcccggga tagtcaaaat gactgcacgt tggtgacact ggctctctca gggttgctgg | 420 |
| gtctgcatgc ggagccatttt gtgtgtctga agtctgccca tcaacctgcc tgtccgcagc | 480 |
| cctcgcaatg gagaatgcat | 500 |

<210> SEQ ID NO 168
<211> LENGTH: 500
<212> TYPE: DNA
<213> ORGANISM: homo sapiens

<400> SEQUENCE: 168

| | |
|---|---|
| ttcatactct cgagcatggt cagaaagggt caaggtctga aaacagcgtc ttgcgcgtgt | 60 |
| tgactcaccc tgtccccaga cagcaggcag tttccactgg ggctccaacg gagcacggtg | 120 |
| atgtcggctg tgtgtgtcag gggcatcgtg tgctgctcct tgtcctgctt gttaaacacc | 180 |
| gtcacttctc cagtctccca gcccacagcc agcaccagcc gcgtcgggtg ccagcacagg | 240 |
| gaagcaaccc ggaacggcct ctcgacgtgt gtatctggca cgcactcccc ctgcattgga | 300 |

```
tgagaggcaa attcccacag ttcagagagg gacagctact tttaagaact tctgtctagg      360
ccgggcacgg cggctcactc ctgtaattac agcactttgg gaggctgagg tgggtggatc      420
acaaagtcag gagttcgaga ccagctgggc caatttggtg aaactccgtc tctactaaaa      480
atacaaaaat tagccaggtg                                                  500

<210> SEQ ID NO 169
<211> LENGTH: 500
<212> TYPE: DNA
<213> ORGANISM: homo sapiens

<400> SEQUENCE: 169
ggatccttct cacttataaa tgtgtataaa agaaatttct ttttcctccc cctccactcc       60
ttctatttct gccctatttt tttccaggaa gaaaaaatgc tgggcatctt ggtgcagcac      120
aaagtccgga gtggcgtctc gggcatcgtg ggcatggagg tggatgggct gcccttccac      180
aacacccacg ccgagatgat ccagaagctg gtggacgtca ccacggcaca ggtgtaaccg      240
tccatgttcc gtgtgagcag agtccctacc aacgggcagg tctgcatccg gggagaatgc      300
agctgcttct ggcgacaatc ctgctagtaa acactggtct tcggtgagca acgaacactc      360
gcctggcctg ggaaactgca tgcccacttt ctgggagggg ttagtgcagg tgctgtggac      420
aaaggacaac atttctctgg ggcttttaa cttttattcc taagactcta aaggcgttga      480 tttcaacccct ccttcactct                                                 500

<210> SEQ ID NO 170
<211> LENGTH: 500
<212> TYPE: DNA
<213> ORGANISM: homo sapiens

<400> SEQUENCE: 170
gtgtgcgagg tggggcccaa ggagccagca gcagccgtcg cggccacggc caccaccacc       60
ccagccactg ccaccaccgc ctctgcctcc gcctcttcca ctggagagcc cgaggtcaaa      120
aggtcccggg tggaggagcc cagtggtgct gtaaccacac cggctggagt gatcgcagct      180
gccggccccc aggggccagg caccggggag tgaggtcacc tgcaacgcgg gggagtggga      240
ctcacccagc ggcgacccccg aagctggacc cggcagctca gcggccgca cccacagacg      300 gaggagaaca gcccgcggcg gcctgtgggc atcggcggca cctggacaca cccagccctt      360
tccatttgat cgcctgcctt cccgtggttt aagacaaaaa cacataaaca agttcagaca      420
actgattgta tgattctggg aattctttgc tttcctttcc ttctccctcg gcaccacctc      480
ctctccccag gcctccctgt                                                  500

<210> SEQ ID NO 171
<211> LENGTH: 500
<212> TYPE: DNA
<213> ORGANISM: homo sapiens

<400> SEQUENCE: 171
gccaatgagg aagagagcgc acgggcagaa accagagctg ggagggcaag taacgcagtc       60
tttatttaca ccacaagata acacgttgcg tgatgtggta cagaatactg gactccagtg      120
aagtggaaag aaggtgaccg tcagaagagg atatcattgg tcggtgaaaa tccacccaca      180
caaaacaaga caagaatgag aaaaccaaac acaaaacctc caactccact gagcaaaaga      240
aagaaccatc gggcacgtcc agacaatcca agagaaacgg attaaattac agaggtgaat      300
```

```
ggtggccacg gccagtgcgc agctcacggc gggcgcgaac aggcatcagg taggttacag    360
tgtcgttaca acttggtttt ctaccacatt ccgtaagaag ctcttgggtg agtaaggttc    420 aagcccctg tatagataga tagatagata gatagataga tagattatat atgtttgtca     480
ttctcatcaa ttggaaaata                                                500

<210> SEQ ID NO 172
<211> LENGTH: 500
<212> TYPE: DNA
<213> ORGANISM: homo sapiens

<400> SEQUENCE: 172
acttcctgca ggcttcagaa tgtttgagca tgaaaacaaa tggaagcagg cttactttcg     60
atgtcttatt aaggtcttta ccatgatcaa tgttaccttt atgacaagct tcatatgcct    120
tgttaggcag aatgttttgg atggtaaaaa tcctgactcc caaagcatca acattccaag    180
taactacttc agtttcagtt ccgctcacca gtgctacagg agcagcgtgc agcgggtcct    240
gcttccattc gactggctgt gcaggacggc cacaaacaca cgcaggtgca ccctgcgctt    300
ctgagcagaa ctctcggaat gaagtaatgc agacgtccac aaatgagatg tgatttcact    360
gagggaggct gattttttagc agttgttcct tttttaacag atagtctata agtggaaact    420
gacctgaaac attcagctct aaagaaataa tcacaaagca cctcggtgcc tgattttgc     480 aaggcagtcc ttgccggagg                                                500

<210> SEQ ID NO 173
<211> LENGTH: 500
<212> TYPE: DNA
<213> ORGANISM: homo sapiens

<400> SEQUENCE: 173
gccggggctt ctgccgtggc tgcagcaacg gacccagtgc ccactccggg gtctaaagag     60
tggcctttca ttatggaatt atttaatccc cgccacttca ccgctggcac cgtcgaggtc    120
tgggggcagg tctgactggt ttcctttacc ttagtgaagc cggcggcctg caccgacccg    180
gctcgcgccc atcccggggt cacccacatt tgggtgaact tgaacgagtg cccgaccagg    240
taacgttgcc ggacctccca caagagggca ctttctttc tcccatttg tcctcattct      300 ttccagccag gtaggtcgcg cttttttctc tgtgcaagga agttgatggt ggtcattttt    360
tttttttttt ttttaatacg gagtctctct ctgtcgccca ggctggactg cagtggcgcg    420
atctcggctc gctgcaagct ccgctcccg ggttcacgcc attctcttgc ctcagcctcc     480
cgagtagctg ggactacagg                                                500

<210> SEQ ID NO 174
<211> LENGTH: 500
<212> TYPE: DNA
<213> ORGANISM: homo sapiens

<400> SEQUENCE: 174
tgtaatctgt tttgttatct gatttcccac ctgtcctagg taggaaaggt gtactcctga     60
ggatgacacg tgggacccag gcagtccttg ctgctcttac agatgcgcgc ttttggggtc    120
atcaggcggt tgcaaaggtg ggagcagccg tgctccccag aatgctgaca gcacagagca    180
ctggtctgaa gatctgtgtg tggctgtgat ccgtgcgtgg ctgtgacccg tgcgtggctt    240
tggcccgtgc gtggctccgg cccgtgtgtg gcggttgccc atgtgtggct gtgacatgtg    300
gaggcgaact tccacggcag aagtgccatg cttccgtaag ctcttccgac tggttggtag    360
```

| | | |
|---|---|---|
| gcgcttttat cggcacatga gcaccttaca gacaaatatc tgaagtacac ttcaaaggag | 420 | |
| gcaaagaaaa agcaaaactg ccagttcctt gagcatggct gtgtgtcgtt ggtgctctga | 480 | |
| agggcttgag aatctctctc | 500 | |

<210> SEQ ID NO 175
<211> LENGTH: 500
<212> TYPE: DNA
<213> ORGANISM: homo sapiens

<400> SEQUENCE: 175

| | |
|---|---|
| gcggtcacaa gtcccctctc ctccgcatgg acaccaggaa tgcggggtct ggcggtgctg | 60 |
| ggcgcagggc gagaagattt gatgtgcagg gtaagtaaag gacaagttat ttaaaacctc | 120 |
| aacacaggaa aagatggtaa gagtgctgtg tagccctttg cttgcttgtg actacgagtc | 180 |
| gctaggtggc ccgcgtttag agtatgccta cggcgcctac taacgtctag acctaggaga | 240 |
| ggcgtctccc gccctcgac ccacagccag ccgccacttg atagctaacg cgtcttccgg | 300 |
| ccggtacaca cccacaatta atctttctta ttaaagcctc cattctgtac ccatggggcg | 360 |
| actcaaacct atttagattt ccgtggttgg ctgcacaaat ttaagtgggc aacgagttat | 420 |
| aaacctaata acagaggacg agagagggtg atttgagtag agaagacgca agattcacta | 480 |
| gggtcgtgaa gatgctgcgg | 500 |

<210> SEQ ID NO 176
<211> LENGTH: 500
<212> TYPE: DNA
<213> ORGANISM: homo sapiens

<400> SEQUENCE: 176

| | |
|---|---|
| atggtaggtg tgagggggggc gatctcagaa cagggaggtg ttgattaacg taggagtggg | 60 |
| ctcgttctag acagtgtaga gtgacgccct ttcagttgtt gaggagcagc aatatagaag | 120 |
| agagggcaga tgagtctgag ggagacatcg tgttaggttt aactttatac atctcagatt | 180 |
| tgccagtctg aagtagttta gaaagccagg ttcgcgcagg cgcaggaggt ctgtcgttgc | 240 |
| cgagaactgc gacgtccacg tgcacacagt gctggctgcg gcctgaagag ctggctgctt | 300 |
| cccgcacgtg cgtgcaggtg cttcaggtg tgtgttggtg tcgatgtgat ggaagaaatt | 360 |
| catttaaaag ctttgctgag tcacggcagt agtgtcttga gttttctcaa gtggtaccaa | 420 |
| aagttcaaca actcgtttga gagtctgtga aattgaatgg cacagaaagg gagaactgat | 480 |
| ggaaaaggtt gaaagtcatt | 500 |

<210> SEQ ID NO 177
<211> LENGTH: 500
<212> TYPE: DNA
<213> ORGANISM: homo sapiens

<400> SEQUENCE: 177

| | |
|---|---|
| tcgcccaggc tggagcgcag tggcgcgatc tcggctcact gcaacctctg ccttccaggt | 60 |
| tcaagcgatt ctcctgcctc agccccgagt agctgggact actagcgcat gcagcacgcc | 120 |
| cggctaattt tttgtatttt tagcagagac ggagtttcac cgtgttagcc aggatggtct | 180 |
| cggatctcct gacctcctga tccgcccacc tcggcctccc aaagtgctgg gattacaggt | 240 |
| gtgagccacc gcgcccggcc gcacacaaac tcttaagcag aaggctttga acattccaat | 300 |
| atcaggccac tatactctta ataagtattt gtggattaat tcatctgtgg actctttaga | 360 |

| | |
|---|---|
| acaggagagg ccgtgggaag ggcagacact gccactgcta aatcaattac cgtatattac | 420 |
| tcaactttt aggctgagcc agggaggccc ctatagggca gagtgctctg aatcttggga | 480 |
| tgtcaggaca gactgggcag | 500 |

<210> SEQ ID NO 178
<211> LENGTH: 500
<212> TYPE: DNA
<213> ORGANISM: homo sapiens

<400> SEQUENCE: 178

| | |
|---|---|
| agggacaaag agcaagcaaa aggaagggaa atcagtcttg gggcaaagag tcctggatgt | 60 |
| cacgactgca gatgttctta cgtgtgcttt cctgtgactg catctgcatg gcttgttctt | 120 |
| ttaacctta gttcaacaca tatttattga gcacctacta tgtgcttggg atacatcagt | 180 |
| gaaaaaaacc cttccctggt ggaacctcta ccgacatctc agaaggatgt ctccagaata | 240 |
| gacgttgcac ggatgggggc ttgagtaatt cagtcctgag ctggacaagt cggagcggtg | 300 |
| ccacttctgg gctctgtggt ctcaggtatg tggcttaacc tctctgatct cagcatcatt | 360 |
| cattcaaatg acaagactca tactaatctt gcaaggtaca ggtagtaaaa atagagctta | 420 |
| agaatgtagg ctctcaggtt cactggcagg gaccgatccc ttacagactg ccagcacagg | 480 |
| tgggttactc agtgtctctg | 500 |

<210> SEQ ID NO 179
<211> LENGTH: 500
<212> TYPE: DNA
<213> ORGANISM: homo sapiens

<400> SEQUENCE: 179

| | |
|---|---|
| gcagaagcga tgggagatca tggggagggc agcccggcgg gaggcgcgga cgaacaggac | 60 |
| cgcccagccg cgagaaggct cagcccaggc aggggtcggg gcgcgctggg cgcgtgtggg | 120 |
| gacgcacctg ggtctcctcc tcggaaaggc ctgcctcggc cgcgatgagg cacagcgtgg | 180 |
| tggaatccgg gtgcttgtcg accttgttga agttgtactc caggatttcc acctggtcct | 240 |
| ctgtggggcc gctcgcggtc tccgccgaca tggtccctgc gcgctgcggg gcagggagaa | 300 |
| gcggcggcgg tgagcgaggc gtggagcggg cgggacgcag cgaaggaagg cggtcgcggc | 360 |
| gccgccgggg agccccagcc ccaggccgcc cctccagcg gtgccacggc cgcgcaagtc | 420 |
| cccggtggct gcacgctgag cgggggctta cggctgcccc ccacccgggc ctccctccct | 480 |
| ggactgagcg ctgttgcggg | 500 |

<210> SEQ ID NO 180
<211> LENGTH: 500
<212> TYPE: DNA
<213> ORGANISM: homo sapiens

<400> SEQUENCE: 180

| | |
|---|---|
| gtctggctct gtagcccagg ctggagtgca gtggcgcgat ctcggctcac tgcaacctcc | 60 |
| gcctcccggg ttcaagcagt tctgcctcag cctcccgaag ggcgccacca tgcctggcta | 120 |
| attttgcat ttttagtaga cagggtt cgccatgttg gccaggctgg tctcgaactc | 180 |
| ctgacctcaa gctatctgcc cgcctcggcc tcccagagtg ccgagattac aggcgtgagc | 240 |
| caccgcgccc ggcctaccct tgaagacccc gcagccaagg tcctccggcc ccgtctgcg | 300 |
| cggcgctctg gtcttggggc tccggactct gtcatgccgg gcaggggcca gtccgatcct | 360 |
| tgcaccttg cctggcaccg tccctggagc cttggcgtcc tggcctctcc tccccgcggg | 420 |

```
ctggaggtgg agtggccggg ccggaaccag tgcgcaaagc agatggcgag cgcggaggtc    480
ggttcggccc cgccgcgcct                                                500

<210> SEQ ID NO 181
<211> LENGTH: 500
<212> TYPE: DNA
<213> ORGANISM: homo sapiens

<400> SEQUENCE: 181
agattacagg cgtgagccac cgcgcccggc ctacccttga agaccccgca gccaaggtcc     60
tccggccccg ctctgcgcgg cgctctggtc ttggggctcc ggactctgtc atgccgggca    120
ggggccagtc cgatccttgc acccttgcct ggcaccgtcc ctggagcctt ggcgtcctgg    180
cctctcctcc ccgcgggctg gaggtggagt ggccgggccg gaaccagtgc gcaaagcaga    240
tggcgagcgc ggaggtcggt tcggccccgc cgcgcctcaa ggcagcagcc accctgggga    300
aggtggatgc cggaagaggc gtcgcctgcg ggtcacccag aggacacccg gcggggaatt    360
ccgagggtgg gagtgaggag aggtaggaga ggccacggca gagggaggcc ccgcgcagag    420
tgggaaccat cgcccggtgc gggcctgaac ttccagggcc ggctactcct cggcagagcg    480
accgcgcggt gtctcagagc                                                500

<210> SEQ ID NO 182
<211> LENGTH: 500
<212> TYPE: DNA
<213> ORGANISM: homo sapiens

<400> SEQUENCE: 182
ggagggaggg aagggagaag agaatacgaa ttaattacga aggaaaccca ggtgtgaaag     60
gcacccgccg cggagctggg cgtgcagcgg ggcgcgcggt gggacctctg ctcccgtccc    120
cgtcccgcgg ctactcagtt gcccgctcat gggaggctcg cgacggaaaa taaatcccct    180
cagagtgaac ctgggaggcc gagaggaccc agcctgggat ctctggggga aatagggggca    240 agtttaccac ggtttaatta agccacagcc ctagcacgag gaccccggcg acccatccgg    300
gctgggggat ggactggagt gccccccacc ccaggccgcg aaccggcagc gagaagcaca    360
ctctccgcca tccccggccc cgccgcttcc gcctctgcgg actccgcgtt tgccatgctc    420
cttcccgggg tccagggacc ggagctgcgg tgcacgtctt attgaagggg agagctttgg    480
ttcttttcct ccctgcatcc                                                500

<210> SEQ ID NO 183
<211> LENGTH: 500
<212> TYPE: DNA
<213> ORGANISM: homo sapiens

<400> SEQUENCE: 183
aatggtagaa actttggaaa ttctcatcct cccactaagg gtagtgcttt tcagacaaag     60
ataccattta atagacctcg aggacacaac ttttcattgc agacaagtgc tgttgttttg    120
aaaaacactg caggtgctac aaaggtcata gcagctcagg cacagcaagc tcacgtgcag    180
gcacctcaga ttggggcgtg gcgaaacaga ttgcatttcc tagaaggccc ccagcgatgt    240
ggattgaagc gcaagagtga ggagttggat aatcatagca gcgcaatgca gattgtcgat    300
gaattgtcca tacttcctgc aatgttgcaa accaacatgg gaaatccagt gacagttgtg    360
acagctacca caggatcaaa acagaattgt accactggag aaggtgacta tcagttagta    420
```

```
cagcatgaag tcttatgctc catgaaaaat acttacgaag tccttgattt tcttggtcga    480
ggcacgtttg gccaggtagt                                                500
```

<210> SEQ ID NO 184
<211> LENGTH: 500
<212> TYPE: DNA
<213> ORGANISM: homo sapiens

<400> SEQUENCE: 184

```
cagtgagccg agattgggcc actgcactcc agcctgggtg acacagtgag actctgtctc     60
aaaacaaaag aaaaaaccat attcagatct tgatgggatt tgaattcttc ctgaagtaga    120
atataaagcc atattcagat acacaaccat attcagatct gctcaaaaac gagacaaaga    180
aaaatagtta acagaaagga atacaaaaac ttattcagat ctcgatggag cttgagtcac    240
acaggcatgc gcatcggtca gatgtacccct taagattttg cgcgttgcag ctgggcccag    300
gggctcatgc ctgtaatcca gcactttggg gaggctgagg cacgcagatc tcttgagctc    360
aggagtttga ccagcctg gcaacatgg tgaaaccata tctctacaaa aaaaaaccaa    420
aaattagctg ggcgtggtgg catgtgcctg tagtcccagc taccagggag gctgaggctg    480
gaggaaagcc tgaacccagg                                                500
```

<210> SEQ ID NO 185
<211> LENGTH: 500
<212> TYPE: DNA
<213> ORGANISM: homo sapiens

<400> SEQUENCE: 185

```
ttgactcaca atttgtggca ccactttctc atcccagaac ttcattctta tttctctcct     60
catctggcct cccaagtgct ccgttgagct gatgaaaagt tctttgtact ccctcaacgt    120
gtcggaaaca ggaggccaca cagcacagct ttgtttgggg tgggcaggag tcaggagtct    180
tgagcagatg catcactgtg aagaagaacg acatgtcggg gctgcacctg tcctcccgtc    240
ggcatttgac gaaagctccc tgaagcgggg cagcactctc ctcctgagag atttaccatt    300
tattgcccct gtgaggaatg tgtgcttggg aactgccaag tcttacccct tctggaagaa    360
gaggttttct ctgacaagag cctagagcgt cggctctatt atgctgggac ttgacagagg    420
agccatgggg tttaaacagt aggaaagagg ggctacgcgc agtggctcac gcctgtaatc    480
ccagcacttc gggaggcgaa                                                500
```

<210> SEQ ID NO 186
<211> LENGTH: 500
<212> TYPE: DNA
<213> ORGANISM: homo sapiens

<400> SEQUENCE: 186

```
tttctcacct ctggactttt gcacatgctg ttcccatcag cttgatgctc ttcctgcagt     60
tttttgcctg gcgaattcct gggtaccgtt tacatttcag cgtaaacatc agaccttcct    120
ggtccagcgc ccactcccaa tccaaaatca gttcctcccc attaccaaaa atccctcatt    180
gataccctct acttttcctt cctgggaaac ttgtaattac agctgtaatg cagtcacagt    240
ttgtaattac gcttgtgtgc gtgcgtgcgt gtctgtgagc cctactggat ccaagcccca    300
gcaggcaagg attgcacctg cttgctcgcc atgctgtgtc tcccctggca cagcgcctgg    360
cacagtgcct ggcacgtcgt ccacgctcca tggatatttg tttcgatgca tgcacaggtg    420
cacccccata gctttgtgac tctctgatag gcggtgggt gtggacacag gcgtccccc    480
```

| | |
|---|---|
| atccagggtg gtaggtgtag | 500 |

<210> SEQ ID NO 187
<211> LENGTH: 500
<212> TYPE: DNA
<213> ORGANISM: homo sapiens

<400> SEQUENCE: 187

| | |
|---|---|
| gtgccgattg tcacacttgc ctgtgtccag ccactgaccg cgtcaaccat gctgccattt | 60 |
| tcatcagggt cccatcttat ttttaatgtg attttgtgta gcagggtgac ttttaggaac | 120 |
| acacatcacc ttagaataga actaaccata tgtttgttga gtgagttgat gatgaactac | 180 |
| ctcacacata tatttgaaca ttacaattta aaaatatttt caaagcattc cctcatgtaa | 240 |
| tctgtgaatc ggctccccgt gcagatgggg tgaggcgtgc atgcttcatt cttccagaga | 300 |
| ggaagcaaag gcaaagagag ggaaagggag ctggcgccag gcacaagtga gagagtgaca | 360 |
| gagctcaggt tctaacaggt tttctgattc cagctcctag gcttcctccc cctagaagag | 420 |
| aggaattcca gcagggctgg cctcaggcct ccacctccct tcccggtgcc ccgcccaggg | 480 |
| tcagaccctc tccctgcaca | 500 |

<210> SEQ ID NO 188
<211> LENGTH: 500
<212> TYPE: DNA
<213> ORGANISM: homo sapiens

<400> SEQUENCE: 188

| | |
|---|---|
| gagttccccg cgcagggggc aggtgcgccc cacctgggtg ccaagggagg cgacaccatc | 60 |
| tctccccctt ggggtggccc agccttgcct accatgatct ccaggccggg ggctcagccc | 120 |
| tcatgcctgg gaacagaggc tgctttacgg ggtgagggcc tggggccccc cgagccttcc | 180 |
| ccaggcaggc agcatctcgg aaggagccct ggtgggttta attatggagc cggcgctgac | 240 |
| cggcgtcccc gccctcccca cgcagcctcc ttggtgcggt ccaacacatc accgggcaag | 300 |
| ctgaggcctg ccccggactt ggatgaatac tcatgaggaa taaggggtg ggccgcgggt | 360 |
| tttgttgttg gattcagcca gttgacagaa ctaagggaga tgggaaaagc gaaaatgcca | 420 |
| acaaacggcc cgcatgttcc ccagcatcct cggctcctgc ctcactagct gcggagcctc | 480 |
| tcccgctcgg tccacgctgc | 500 |

<210> SEQ ID NO 189
<211> LENGTH: 500
<212> TYPE: DNA
<213> ORGANISM: homo sapiens

<400> SEQUENCE: 189

| | |
|---|---|
| gggatggtcg gctcacctgt ggggctctgt cctgctcttg cagcctccca gggtcactga | 60 |
| aaggttcttg gctgaaggag cagaaaccta aatggagtcc tcccctctgt tctcccatc | 120 |
| cctgcccggg agtccggtcc cagtttgttc ctctaagcgg tcgtggcctc cgcctgcagg | 180 |
| gctggccact cgagggaagg tggtacttca ggttcctcga gggagcggct tcggtgttgt | 240 |
| ttctctcacc gtcccgccgg cgtcaccggt gctgcgtgct gagtgggctg ggacgtagga | 300 |
| aggcctggcc gatgacaggc acggcctgat gtgtgtacac cagaacctgg atggtggctg | 360 |
| acacaggcca gacccagaaa cccctcgccc acttgctggg gtcatagtga tacagaagag | 420 |
| aaagaaacac aaaacaagat gcccagtcgt gtgtaaagga aacatcagga aaccccctgg | 480 |

```
ccagtcaccc aggtagaagc                                             500

<210> SEQ ID NO 190
<211> LENGTH: 500
<212> TYPE: DNA
<213> ORGANISM: homo sapiens

<400> SEQUENCE: 190
cactgcgggg gtggggtggg gtggggtccg gtggacgtct ggttgctcag tgttctgtga     60
tcgtttctgc aggggggtaaa ggaagtggta tctttgacga atcaacccc gtgcagactc    120 gacagcacct gaacccacct ggagggaaga ccagcgacat ttttgggtct ccggtcactg    180
ccacttcacg cttggcacac ccaaacaaac ccaaggtatg gactgcattc agacgtgaca    240
gcgcagcagc gggtatgcca ggtgctcttt ccaaaaaggc tccaaggcag atgcgacatg    300
tttttaggga gaatcatggt gggtgccgta gattatcctg gatgcaagca ttagtcatcg    360
agtttggaag ttcccctgag tcacccagga aacagtccag ccttgtgctg actgaagccg    420
tgggggaagc tcttctgtgc tggtggcgga cgcccactgc agacgggctg tggcggctcc    480
tcactgcagt gctgcggggc                                             500

<210> SEQ ID NO 191
<211> LENGTH: 281
<212> TYPE: DNA
<213> ORGANISM: homo sapiens

<400> SEQUENCE: 191
tgtctggggg tagaggacct agagggccgg gctgggcagc cggcttcctg cactgtctgt     60
tgggacgtcc ctttctgact gggtttctca gaagctgaat gggggatgtt tctgggacac    120
agattatgtt ttcatatcgg ggtctgcatc tgggccctgt tgtcacagcc cccgacttgc    180 ccagatttttt ccgccattga cgtcatggcg gccggatgcg ccgggcttca tcgacaccac    240
ggaggaagag aagagggcag ataccccacc ccacaggttt c                        281
```